(12) United States Patent
Watt et al.

(10) Patent No.: US 12,208,107 B2
(45) Date of Patent: Jan. 28, 2025

(54) METHOD AND COMPOSITIONS FOR THE TREATMENT OF ANEMIA THROUGH THE INHIBITION OF FURIN

(71) Applicant: Brigham Young University, Provo, UT (US)

(72) Inventors: Richard K. Watt, Provo, UT (US); Chad Hancock, Provo, UT (US)

(73) Assignee: Brigham Young University, Provo, UT (US)

( * ) Notice: Subject to any disclaimer, the term of this patent is extended or adjusted under 35 U.S.C. 154(b) by 181 days.

(21) Appl. No.: 17/934,333

(22) Filed: Sep. 22, 2022

(65) Prior Publication Data

US 2023/0038724 A1    Feb. 9, 2023

Related U.S. Application Data

(62) Division of application No. 16/078,591, filed as application No. PCT/US2017/018735 on Feb. 21, 2017, now Pat. No. 11,458,148.

(60) Provisional application No. 62/298,259, filed on Feb. 22, 2016.

(51) Int. Cl.
| | |
|---|---|
| *A61K 31/635* | (2006.01) |
| *A61K 31/427* | (2006.01) |
| *A61K 33/26* | (2006.01) |
| *A61K 38/18* | (2006.01) |
| *A61K 45/06* | (2006.01) |
| *A61P 7/06* | (2006.01) |

(52) U.S. Cl.
CPC .......... *A61K 31/635* (2013.01); *A61K 31/427* (2013.01); *A61K 33/26* (2013.01); *A61K 38/1816* (2013.01); *A61K 45/06* (2013.01); *A61P 7/06* (2018.01)

(58) Field of Classification Search
CPC .................................................. A61K 31/635
See application file for complete search history.

(56) References Cited

U.S. PATENT DOCUMENTS 11,458,148 B2 * 10/2022 Watt ....................... A61K 33/26
2008/0260736 A1    10/2008 Lin et al.

FOREIGN PATENT DOCUMENTS

WO    2017147078 A1    8/2017

OTHER PUBLICATIONS

Mylonakis et al., Combination antiretroviral therapy including a protease inhibitor eliminated the transfusion requirements of HIV-infected individuals with anemia of chronic disease, Journal of Acquired Immune Deficiency Syndromes and Human Retrovirology, vol. 19(3), pp. 306-307, Nov. 1, 1998.*
Andrew J. Gross, Ph.D. dissertation, Discovery of an Allosteric Site on Furin contributing to Potent Inhibition: A Promising Therapeutic for the Anemia of Chronic Inflammation, Brigham Young University, Department of Chemistry and Biochemistry, Jul. 2014, 218 pages.*
Agarwal et al, Anemia of chronic disease (anemia of inflammation), Acta Haematol 2009;122:103.*
Vanommeslaeghe, K., Raman, E. P. & Mackerell, A. D. Automation of the CHARMM General Force Field (CGenFF) II: Assignment of Bonded Parameters and Partial Atomic Charges. J. Chem. Inf Model. 52, 3155-3168 (2012).
Laskowski, R. A. & Swindells, M. B. LigPlot+: Multiple Ligand-Protein Interaction Diagrams for Drug Discovery. J. Chem. Inf Model. 51, 2778-2786 (2011) ; https://doi.org/10.1021/ci200227u.
Lineweaver, H. & Burk, D. The Determination of Enzyme Dissociation Constants. J. Am. Chem. Soc. 56, 658-666 (1934).
Nelfinavir. DrugBank (2013). at http://www.drugbank.ca/drugs/DB00220>; CAS Creation date Jun. 13, 2005, Updated Feb. 21, 2023.
Emans, M. E. et al. Red cell distribution width is associated with physical inactivity and heart failure, independent of established risk factors, inflammation or iron metabolism; the EPIC—Norfolk study, Int. J. Cardiol. 168, 3550-3555 (2013) ; DOI: 10.1016/j.ijcard.2013.05.002.
Kurowski, M., Kaeser, B., Sawyer, A., Popescu, M. & Mrozikiewicz, A. Low-dose ritonavir moderately enhances nelfinavir exposure. Clin. Pharmacol Ther. 72, 123-132 (2002); DOI: 10.1067/mcp.2002.126178.
Thomas, C. & Thomas, L. Anemia of Chronic Disease: Pathophysiology and Laboratory Diagnosis. Lab. Hematol. 11, 14-23 (2005) ; DOI: 10.1532/LH96.04049.
Arikawa, E. et al. Cross-platform comparison of SYBR® Green real-time PCR with TaqMan PCR, microarrays and other gene expression measurement technologies evaluated in the MicroArray Quality Control (MAQC) study. BMC Genomics 9, 328 (2008).
Babitt, J. L. et al. Modulation of bone morphogenetic protein signaling in vivo regulates systemic iron balance. J. Clin. Invest. 117, 1933-1939 (2007).
Bikadi, Z. & Hazai, E. Application of the PM6 semi-empirical method to modeling proteins enhances docking accuracy of AutoDock. J. Cheminformatics 1, 15 (2009).
Falzacappa, M. V. V. et al. STAT3 mediates hepatic hepcidin expression and its inflammatory stimulation. Blood 109, 353-358 (2007).
Grosdidier, A., Zoete, V. & Michielin, O. EADock: Docking of small molecules into protein active sites with a multiobjective evolutionary optimization. Proteins Struct. Funct. Bioinforma. 67, 1010-1025 (2007).

(Continued)

*Primary Examiner* — Svetlana M Ivanova
(74) *Attorney, Agent, or Firm* — Barnes & Thornburg LLP; Ryan L. Marshall

(57) ABSTRACT

Methods and compositions that can be used to modulate the activity of furin in a subject are disclosed herein. In some embodiments, the methods include administering a pharmaceutical composition including a protease inhibitor. In some embodiments, the protease inhibitor inhibits furin activity by binding to the catalytic site, the allosteric site, or both.

21 Claims, 76 Drawing Sheets

(56) References Cited

OTHER PUBLICATIONS

Gross Andrew J., Ph.D., "Discovery of an Allosteric Site on Furin, contributing to Potent Inhibition: A Promising Therapeutic for the Anemia of Chronic Inflammation", Brigham Young University, Department of Chemistry and Biochemistry, Jul. 2014, 218.

Hanson, R. M. Jmol—a paradigm shift in crystallographic visualization. J. Appl. Crystallogr. 43, 1250-1260 (2010).

Hanson, R. M., Prilusky, J., Renjian, Z., Nakane, T. & Sussman, J. L. JSmol and the Next-Generation Web-Based Representation of 3D Molecular Structure as Applied to Proteopedia. Isr. J. Chem. 53, 207-216 (2013).

Jankowska, E. A. et al. Iron deficiency: an ominous sign in patients with systolic chronic heart failure. Eur. HeartJ. 31, 1872-1880 (2010).

Kemna, E. H.J. M. et al. Regulation of hepcidin: Insights from biochemical analyses on human serum samples. Blood Cells. Mal. Dis. 40, 339-346 (2008).

Lau, C. D., Levesque, M. J., Chien, S., Date, S. & Haga, J. H. ViewDock TOW: high-throughput visualization of virtual screening results. Bioinformatics 26, 1915-1917 (2010).

Lefebvre T. et al., "LC-MS/MS method for hepcidin-25 measurement in human and mouse serum: clinical and research implications in iron disorders", Clin Chem Lab Med 2015, 53(10), pp. 1-11.

Morris, G. M. et al. Automated docking using a Lamarckian genetic algorithm and an empirical binding free energy function. J. Comput. Chem. 19, 1639-1662 (1998).

Munoz, M., Garcia-Erce, J. A. & Remacha, A. F. Disorders of iron metabolism. Part II: iron deficiency and iron overload. J. Clin. Pathol. 64, 287-296 (2011 ).

Pettersen, E. F. et al. UCSF Chimera—A visualization system for exploratory research and analysis. J. Comput. Chem. 25, 1605-1612 (2004).

Sasu, B. J. et al. Anti-hepcidin antibody treatment modulates iron metabolism and is effective in a mouse model of Inflammation-induced anemia. Blood 115, 3616-3624 (2010).

Solis, F. J. & Wets, R. J.-B. Minimization by Random Search Techniques. Math. Oper. Res. 6, 19-30 (1981).

Song, S.-N. J. et al. Down-regulation of hepcidin resulting from long-term treatment with an anti-IL-6 receptor antibody (tocilizumab) improves anemia of inflammation in multicentric Castleman disease. Blood 116, 3627-3634 (2010).

Thomas, G. Furin at the cutting edge: From protein traffic to embryogenesis and disease. Nat. Rev. Mal. Cell Biol. 3, 753-766 (2002).

Weiss, G. & Goodnough, L. T. Anemia of Chronic Disease. N. Engl. J. Med. 352, 1011-1023 (2005).

Agarwal et al, Anemia of chronic disease (anemia of inflammation), Acta Haematol 2009; 122: 103-108.

U.S. Appl. No. 16/078,591; Office Action mailed Apr. 2, 2021.
U.S. Appl. No. 16/078,591; Office Action mailed Aug. 13, 2021.
U.S. Appl. No. 16/078,591; Office Action mailed Dec. 1, 2021.
U.S. Appl. No. 16/078,591; Advisory Action mailed Mar. 28, 2022.
U.S. Appl. No. 16/078,591; Interview Summary mailed Jan. 24, 2022.
U.S. Appl. No. 16/078,591; Notice of Allowance mailed May 4, 2022.

International Search Report and Written Opinion in corresponding international application No. PCT/US2017/018735, dated May 17, 2017.

PCT; App. No. PCT/US2017/018735; International Preliminary Report on Patentability.

\* cited by examiner

Pre-Pro-Hepcidin:

Target signal for Endoplasmic reticulum

Full Length 84-amino acid expression of hepcidin

Pro-Hepcidin:

Cleaved to activate hepcidin

Prohepcidin - 35-amino acid precursor

Hepcidin:

Hepcidin-25 - active form of hepcidin

| ZINC ID | PI Name | 3D Structure | 2D Structure |
|---|---|---|---|
| CAS: 15011-399-8 | Dec-RVKR-CMK (Chloromethylketone) | | |
| 3809192 | Amprenavir | | |
| 3941496 | Atazanavir | | |
| 3955219 | Darunavir | | |

Figure 14A

Lineweaver-Burk slope values for Nelfinavir and Darunavir

| Substrate Concentration (µM) | Nelfinavir Slope | Darunavir Slope |
| --- | --- | --- |
| 0 | 0.05835 | 0.02260 |
| 37 | 0.05283 | 0.02288 |
| 75 | 0.04833 | 0.02384 |
| 113 | 0.03310 | 0.02550 |
| 150 | 0.02643 | 0.02544 |
| 225 | 0.02492 | 0.02411 |

Values determined with the use of GraphPad Prism5 statistical software.

Figure 16

METHOD AND COMPOSITIONS FOR THE TREATMENT OF ANEMIA THROUGH THE INHIBITION OF FURIN

CROSS-REFERENCE TO RELATED APPLICATION

The present Application is a Divisional of U.S. application Ser. No. 16/078,591, which is a U.S. National Phase Application of PCT International Application Number PCT/US2017/018735, filed on Feb. 21, 2017, designating the United States of America and published in the English language, which claims the benefit of priority to U.S. Provisional Appl. No. 62/298,259 filed Feb. 22, 2016, the disclosures of each of which is hereby incorporated by reference in its entirety.

BACKGROUND

Field

The present disclosure relates generally to the field of modulation of furin activity and the treatment of anemia.

Description of the Related Art

The proprotein convertase (PC) known as furin is a serine protease capable of cleaving peptide precursors into their active state. Furin is a 794 amino acid serine endoprotease, and like other PCs, dependent on calcium and pH for activity. Furin has a substilin-like domain with a catalytic triad (Ser368, His194, Asp 153) typical of other serine proteases, and an oxyanion hole (Asn295). The oxyanion hole contains an asparagine that is interconnected to Ser368 through a water molecule, allowing for stabilization of serine's deprotonated oxygen during catalysis of a peptide bond. Furin is critical for normal activation of proteins and enzymes. Furin is involved in processing a large number of substrates that are important for normal health. Knockout of furin is lethal at the embryonic stage, as formation of the cardiovascular system and gut are severely defective. Recently, however, furin has been implicated in critical roles within cancers, viral and pathogenic infections, and arthritis through activating precursors novel to the disease type.

Anemia is a medical condition where a decrease in the number of red blood cells is usually accompanied with a lower than normal quantity of hemoglobin in the blood. Anemia of chronic inflammation (ACI), also referred to as anemia of chronic disease, is a type of anemia that commonly occurs in patients with chronic immune activation. The severity of ACI is most commonly related to the severity of the underlying disorder. Certain treatments for chronic diseases may also impair red blood cell production and further contribute to ACI.

Treatment of anemia is usually aimed at correcting the underlying issue, by identifying the source of blood loss, providing transfusions, or supplementing mineral deficiency. In cases of chronic inflammation, chronic disease, or genetic abnormalities, successful treatment of the underlying problem is not always an option. Thus, there is a need to provide effective treatment of anemia, including anemia of chronic inflammation.

SUMMARY

The present disclosure provides a method for modulating the activity of furin in a subject. The method includes, in some embodiments, selecting a subject who is suffering from anemia and reducing the anemia of the patient by administering to the patient an effective amount of a protease inhibitor. In some embodiments, the protease inhibitor reduces the activity of furin.

In some embodiments, the method includes administering to a subject in need a pharmaceutical composition. In some embodiments, the pharmaceutical composition includes a protease inhibitor as the sole active ingredient. In some embodiments, the method includes administering to a subject in a need a pharmaceutical composition. In some embodiments, the pharmaceutical composition includes a protease inhibitor. In some embodiments, the pharmaceutical composition optionally does not include an antibody.

In some embodiments, the method further includes administration to the subject an effective amount of pharmaceutical composition including a protease inhibitor. In some embodiments, the protease inhibitor is selected from the group consisting of amprenavir ((3 S)-oxolan-3-yl N-[(2S,3R)-3-hydroxy-4-[N-(2-methylpropyl)(4-aminobenzene)sulfonamido]-1-phenylbutan-2-yl]carbamate), atazanavir (methyl N-[(1S)-1-{[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl] carbanioyl}-2,2-dimethyl propyl]carbamate), darunavir ([(1R,5S,6R)-2,8-dioxabicyclo[3.3.0]oct-6-yl] N-[(2S,3R)-4-[(4-aminophenyl)sulfonyl-(2-methylpropyl)amino]-3-hydroxy-1-phenyl-butan-2-yl] carbamate), fosamprenavir [(2R,3S)-1-[N-(2-methylpropyl)(4-aminobenzenesulfonamido]-3-({[(3S)-oxolan-3-yloxy]carbonyl}amino)-4-phenylbutan-2-yl]oxyphosphonic acid, indinavir ((2S)-1-[(2S,4R)-4-benzyl-2-hydroxy-4-{[(1S,2R)-2-hydroxy-2,3-dihydro-1H-inden-1-yl]carbamoyl]butyl]-N-tert-butyl-4-(pyridin-3-ylmethyl)piperazine-2-carboxamide), lopinavir ((2S)—N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide), nelfinavir ((3S,4aS,8aS)—N-tert-butyl-2-[(2R,3R)-2-hydroxy-3-[(3-hydroxy-2-methylphenyl)formamido]-4-(phenylsulfanyl)butyl]-decahydroisoquinoline-3-carboxamide), ritonavir [(1,3-thiazol-5-ylmethylN-[(2S,3S,5S)-3-hydroxy-5-[(2S)-3-methyl-2-{[methyl({[2-(propan-2-yl)-1,3-thiazol-yl]methyl})carbamoyl]amino)butan-amido]-1,6-diphenylhexan-2-yl]carbamate), saquinavir ((2S)—N-[(2S,3R)-4-[(3S)-3-(tert-butylcarbamoyl)-decahydro-isoquinolin-2-yl]-3-hydroxy-1-phenylbutan-2-yl]-2-(quinolin-2-yl-form-amido)butanediamide), tipranavir (N-{3-[(1R)-1-[(2R)-6-hydroxy-4-oxo-2-(2-phenylethyl)-2-propyl-3,4-dihydro-2H-pyran-5-yl]propyl]phenyl}-5-(trifluoromethyl)pyridine-2-sulfonamide), and combinations thereof.

In some embodiments, the method includes administration to the subject an effective amount of a protease inhibitor. In some embodiments, the protease inhibitor is nelfinavir. In some embodiments, the protease inhibitor is darunavir. In some embodiments, the protease inhibitor is ritonavir. In some embodiments, the method includes administration of a pharmaceutical composition. In some embodiments, the pharmaceutical composition includes at least one protease inhibitor. In some embodiments, the at least one protease inhibitor is nelfinavir, darunavir, ritonavir, or a combination thereof. In some embodiments, the method includes further administering to the subject an effective amount of protease inhibitor in combination with an iron compound. In some embodiments, the iron compound is selected from the group consisting of ferrous sulfate, ferrous fumarate, ferric pyrophosphate, iron gluconate, iron sucrose, iron dextran, intravenous iron treatments, and combinations thereof. In some embodiments, the method includes administering to the subject an effective amount of one or more protease inhibitor in combination with iron, erythropoietin, a chemotherapy drug, or a combination thereof.

In some embodiments, the subject suffers from or is at a risk of developing anemia. In some embodiments, the anemia is an iron deficiency anemia, a $B_{12}$ deficiency anemia, a folate deficiency anemia, a hemolytic anemic, an aplastic anemia, a glucose-6-phosphate dehydrogenase deficiency anemia, a pernicious anemia, or anemia of chronic inflammation, or combinations thereof. In some embodiments, the subject suffers from or is at risk of developing a chronic disease that leads to anemia of chronic inflammation. In some embodiments, the subject suffers from a chronic disease. In some embodiments, the chronic disease is an infectious or inflammatory disease, heart disease, kidney disease, cancer, or a combination thereof. In some embodiments, the patient suffers from a viral disease, bacterial disease, parasitic disease, fungal disease, or combinations thereof. In some embodiments, the subject suffers from a viral disease including Human Immunodeficiency Virus (HIV), Hepatitis-C virus (HCV), cytomegalovirus (CMV), Dengue virus, Ebola virus, Lassa virus, West Nile virus, or combinations thereof. In some embodiments, the subject suffers from a cancer. In some embodiments, the cancer is a hematologic or a solid tumor cancer, or a combination thereof. In some embodiments, the subject suffers from an autoimmune disease. In some embodiments, the autoimmune disease includes rheumatoid arthritis, vasculitis, sarcoid, inflammatory bowel disease, or combinations thereof. In some embodiments, the subject suffers from Alzheimer's disease, Parkinson's disease, multiple sclerosis, atherosclerosis, diabetes, congestive heart failure, or combinations of any of the aforementioned diseases. In some embodiments, the patient suffers from anemia caused by the treatment of a disease. In some embodiments, the treatment increases the expression of hepcidin. In some embodiments, the treatment is chemotherapy.

In some embodiments, the subject suffers from abnormally low blood iron levels. In some embodiments, the level of iron stores in the subject, including ferritin iron levels, is normal.

In some embodiments, administering to the subject a protease inhibitor inhibits furin activity. In some embodiments, inhibiting furin activity inhibits the formation of hepcidin from the precursor prohepcidin. In some embodiments, inhibition of hepcidin increases the activity of ferroportin iron transport, resulting in increased concentration of iron into the bloodstream, thereby ameliorating the effects of anemia. In some embodiments, ameliorating the effects of anemia includes increasing the iron concentrations in the bone marrow, increasing the synthesis of red blood cells in the subject, increasing the formation of hemoglobin in red blood cells, increasing the ability of red blood cells to carry oxygen, or combinations thereof.

Some embodiments provided herein related to a method for inhibiting development or progression of anemia in a subject. In some embodiments, the method includes selecting a subject who suffers from or is at risk of developing anemia. In some embodiments, the subject suffers from anemia of chronic inflammation. In some embodiments, the subject who suffers from anemia of chronic inflammation suffers from or is at risk of developing an underlying chronic disease. In some embodiments, the underlying chronic disease is an infectious disease, an inflammatory disease, heart disease, kidney disease, cancer, Alzheimer's disease, Parkinson's disease, Human Immunodeficiency Virus (HIV), Hepatitis-C virus (HCV), cytomegalovirus (CMV), Dengue virus, Ebola virus, Lassa virus, West Nile virus, rheumatoid arthritis, vasculitis, sarcoid, inflammatory bowel disease, multiple sclerosis, atherosclerosis, diabetes, congestive heart failure, or a combination thereof. In some embodiments, the subject is treated for or has previously undergone a treatment for an underlying chronic disease, and the treatment for the underlying chronic disease causes anemia. In some embodiments, the treatment is chemotherapy. In some embodiments, the subject has elevated serum hepcidin levels, low serum iron levels, low bone marrow iron levels, low red blood cell count, low hemoglobin levels, or combinations thereof. In some embodiments, the subject has elevated serum hepcidin levels greater than about 50 ng/mL. In some embodiments, the subject has hemoglobin levels of less than about 13 g/dL.

In some embodiments, the method further includes reducing anemia of the subject by administering to the subject an effective amount of a pharmaceutical composition. In some embodiments the pharmaceutical composition includes one or more protease inhibitors. In some embodiments, the one or more protease inhibitors reduces the activity of furin. In some embodiments, the one or more protease inhibitors is selected from the group including or consisting of amprenavir, atazanavir, boceprevir, darunavir, fosamprenavir, indinavir, lopinavir, nelfinavir, ritonavir, saquinavir, simeprevir, and tipranavir. In some embodiments, the one or more protease inhibitors binds to an allosteric site of furin, a catalytic site of furin, or both, in some embodiments, the one or more protease inhibitors includes darunavir. In some embodiments, the one or more protease inhibitors includes nelfinavir. In some embodiments, the one or more protease inhibitors includes ritonavir. In some embodiments, the pharmaceutical composition further includes an iron compound, erythropoietin, a chemotherapy drug, or a combination thereof. In some embodiments, the iron compound is selected from the group consisting of ferrous sulfate, ferrous fumarate, ferric pyrophosphate, iron gluconate, iron sucrose, iron dextran, intravenous iron treatments, and combinations thereof. In some embodiments, the pharmaceutical composition includes one or more protease inhibitors as the sole active ingredient. In some embodiments, the pharmaceutical composition optionally does not include an antibody. In some embodiments, the pharmaceutical composition includes nelfinavir, darunavir, or ritonavir, or any combination thereof. In some embodiments, the one or more protease inhibitor is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 mg, or an amount within a range defined by any two of the aforementioned values. In some embodiments, the one or more protease inhibitors is administered twice daily, once daily, once weekly, or once monthly, or a value within a range defined by any two of the aforementioned values. In some embodiments, the composition includes ritonavir, nelfinavir, and/or darunavir. In some embodiments, ritonavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 mg, or an amount within a range defined by any two of the aforementioned values. In some embodiments, ritonavir is present in an amount of 100 mg. In some embodiments, ritonavir is present, in an amount of 50 mg. In some embodiments, ritonavir is present in an amount of 1 mg. In some embodiments, nelfinavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 mg, or an amount within a range defined by any two of the aforementioned values. In some embodiments, nelfinavir is present in an amount of 2500 mg. In some embodiments, nelfinavir is present in an amount of 45 mg. In some embodiments, darunavir is present in an amount of 10 mg. In some embodiments, darunavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, or 800 mg, or an amount within a range defined by any two of the aforementioned values. In some embodiments, darunavir is present in an amount of 800 mg. In some embodiments, darunavir is present in an amount of 20 mg. In some embodiments, darunavir is present in an amount of 5 mg. In some embodiments, the pharmaceutical composition is administered to the subject once daily.

Some embodiments provided herein related to a method for inhibiting development or progression of a disorder that has a propensity to cause anemia. In some embodiments, the method includes inhibiting the protease activity of furin in a subject suffering from a disorder that has a propensity to cause anemia. In some embodiments, the method further includes decreasing the levels of serum hepcidin in the subject. In some embodiments, the anemia is anemia of chronic inflammation. In some embodiments, the disorder is an inflammatory disease, heart disease, kidney disease, cancer, Alzheimer's disease, Parkinson's disease, Human Immunodeficiency Virus (HIV), Hepatitis-C virus (HCV), cytomegalovirus (CMV), Dengue virus, Ebola virus, Lassa virus, West Nile virus, rheumatoid arthritis, vasculitis, sarcoid, inflammatory bowel disease, multiple sclerosis, atherosclerosis, diabetes, congestive heart failure, or a combination thereof. In some embodiments, inhibiting the protease activity of furin includes administering to the subject a composition including one or more protease inhibitors.

In some embodiments, the e composition includes nelfinavir, darunavir, or ritonavir, or any combination thereof. In some embodiments, the one or more protease inhibitor is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 mg, or an amount within a range defined by any two of the aforementioned values. In some embodiments, the one or more protease inhibitors is administered twice daily, once daily, once weekly, or once monthly, or a value within a range defined by any two of the aforementioned values. In some embodiments, the composition includes ritonavir, nelfinavir, and/or darunavir. In some embodiments, ritonavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 mg, or an amount within a range defined by any two of the aforementioned values. In some embodiments, ritonavir is present in an amount of 100 mg. In some embodiments, ritonavir is present in an amount of 50 mg. In some embodiments, ritonavir is present in an amount of 1 mg. In some embodiments, nelfinavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 mg, or an amount within a range defined by any two of the aforementioned values. In some embodiments, nelfinavir is present in an amount of 2500 mg. In some embodiments, nelfinavir is present in an amount of 45 mg. In some embodiments, darunavir is present in an amount of 10 mg. In some embodiments, darunavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, or 800 mg, or an amount within a range defined by any two of the aforementioned values. In some embodiments, darunavir is present in an amount of 800 mg. In some embodiments, darunavir is present in an amount of 20 mg. In some embodiments, darunavir is present in an amount of 5 mg. In some embodiments, the composition is administered to the subject once daily.

Some embodiments provided herein relate to a method for modulating iron metabolism in a subject. In some embodiments, the method includes determining an amount of serum hepcidin in a subject suffering from or at risk of developing anemia. In some embodiments, the method further includes administering to the subject a pharmaceutical composition including one or more protease inhibitors when the amount of serum hepcidin is above normal levels. In some embodiments, the one or more protease inhibitors inhibit furin activity. In some embodiments, the anemia is anemia of chronic inflammation. In some embodiments, the amount of serum hepcidin in a subject is determined to be greater than 50 ng/mL. In some embodiments, modulating iron metabolism in a subject includes increasing serum iron levels, increasing bone marrow iron levels, increasing red blood cell counts, increasing hemoglobin levels, or combinations thereof.

In some embodiments, the pharmaceutical composition includes nelfinavir, darunavir, or ritonavir, or any combination thereof. In some embodiments, the one or more protease inhibitor is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 mg, or an amount within a range defined by any two of the aforementioned values. In some embodiments, the one or more protease inhibitors is administered twice daily, once daily, once weekly, or once monthly, or a value within a range defined by any two of the aforementioned values. In some embodiments, the composition includes ritonavir, nelfinavir, and/or darunavir. In some embodiments, ritonavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 mg, or an amount within a range defined by any two of the aforementioned values. In some embodiments, ritonavir is present in an amount of 100 mg. In some embodiments, ritonavir is present in an amount of 50 mg. In some embodiments, ritonavir is present in an amount of 1 mg. In some embodiments, nelfinavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 mg, or an amount within a range defined by any two of the aforementioned values. In some embodiments, nelfinavir is present in an amount of 2500 mg. In some embodiments, nelfinavir is present in an amount of 45 mg. In some embodiments, darunavir is present in an amount of 10 mg. In some embodiments, darunavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, or 800 mg, or an amount within a range defined by any two of the aforementioned values. In some embodiments, darunavir is present in an amount of 800 mg. In some embodiments, darunavir is present in an amount of 20 mg. In some embodiments, darunavir is present in an amount of 5 mg. In some embodiments, the composition is administered to the subject once daily.

BRIEF DESCRIPTION OF THE DRAWINGS

FIG. 8A illustrates nelfinavir at the catalytic site of furin showing a hydrogen bond with the catalytic residue serine 368. LigPlots were generated via SwissDock prediction modeling.

FIG. 8B illustrates darunavir, which forms a hydrogen bond with Ala 518. LigPlots were generated via SwissDock prediction modeling.

FIG. 11A shows that, nelfinavir exhibits competitive inhibition whereas FIG. 11B shows that darunavir exhibits uncompetitive inhibition of furin.

FIG. 12 shows that preventive treatment with PIs blocks hepcidin-25 secretion in Huh7 cells. Dose dependent quantification of hepcidin-25 from media of Huh7 hepatocyte cells treated with cytokines and protease inhibitors. Treated cells were incubated for 18 hrs with IL-6 (10 ng/mL) and BMP-9 (10 ng/mL) added to media. All groups received IL-6 and BMP-9 cytokines, except healthy group. The PIs darunavir and nelfinavir in media represent physiological serum concentrations as pharmaceutically prescribed (5, 10, 15 µM), as well as in combination where both darunavir and nelfinavir were present at 2.5, 5, 7.5 µM. Healthy and IL-6/BMP-9 group were without PI treatment. Healthy group with PI treatment did not show significant difference from healthy hepcidin levels. No significant difference is seen between the Healthy and PI 15 µM treatment (p>0.05) (n=4).

FIGS. 14A-C show the protease inhibitor molecules, represented in both two and three dimensions with corresponding chemical identification codes.

FIG. 16 shows the specific Lineweaver-Burk slope values for nelfinavir and darunavir.

FIG. 24A provides a Western blot showing dose dependent inhibition of nelfinavir in Huh7 cells. FIG. 24B is a graphical representation of Western blots showing PI inhibition of pSTAT3 in Huh7 cells (n=4). FIG. 24C is a graphical representation of the phosphorylation of STAT3 in HepG2 hepatocytes (n=4).

FIG. 25A is a graphical representation of the phosphorylation of Smad4 in Huh7 cells (n=4). FIG. 25B is a graphical representation of the phosphorylation of Smadl/5 in Huh7 cells (n=4). FIG. 25C is a graphical representation of the phosphorylation of Smad4 in HepG2 hepatocytes (n=4). FIG. 25D is a graphical representation of the phosphorylation of Smadl/5 in HepG2 hepatocytes (n=4). Co-induction of PIs at 60 µM showed no significant inhibition between PIs for both Smad4 and Smadl/5 (p>0.05).

FIG. 26A shows HAMP gene expression in Huh7 hepatocytes. Treatment with combined nelfinavir and darunavir (ND) reduced HAMP in the presence of cytokine (p<0.05). FIG. 26B shows that prohepcidin increased threefold with PI treatment in Huh7 cell media after 18 hr induction of IL-6 (10 ng/mL) and BMP-9 (10 ng/mL), Treatment with ND increases prohepcidin threefold (p<0.0001). CMK treatment of cytokine-induced cells also significantly raised prohepcidin levels (p<0.01). Prohepcidin levels doubled with IL~6/BMP-9 treated cells as compared to healthy (p<0.05). No difference is detected within healthy groups (p>0.05) (n=4). FIG. 26C shows the results of HAMP gene expression in HepG2 hepatocytes. Treatment with ND did not reduce gene expression significantly (p>0.05) (n=4).

FIG. 27A shows furin Western blot of Huh7 cells after 18 hr incubation with and without inflammatory' cytokines IL-6 and BMP-9, co-treated with ND. FIG. 27B shows that furin mRNA is upregulated with IL-6/BMP-9 induction. FIG. 27C is a graphical representation of furin Western blots in Huh7 cells. No significant difference is seen with treatment of PIs (p>0.05) (n=4). Error bars represent Standard Error. FIG. 27D) shows furin Western blot of HepG2 cells after 18 hr incubation with and without inflammatory cytokines IL-6 and BMP-9, co-treated with ND and CMK. FIG. 27E is a graphical representation of furin Western blots in HepG2 cells. No significant difference is seen with treatment of PIs (p>0.05), but a significant difference exists between healthy and cytokine induced groups (p<0.05) (n=4).

FIG. 28A depicts mass spectrometry quantification of hepcidin-25 under inflammatory conditions in Huh7 cell media. Treatment with ND reduces hepcidin-25 concentrations to near basal levels (p<0.0001) (n=4). Error bars represent Standard Error. FIG. 28B depicts mass spectrometry quantification of hepcidin-25 under inflammatory conditions in HepG2 cell media. Treatment with ND reduces hepcidin-25 concentrations to near basal levels (p<0.01) (n=4).

FIG. 29A provides Western blot of ferroportin under inflammatory conditions with treatment of ND in Huh7 hepatocytes. FIG. 29B shows that ferroportin is degraded in presence of IL-6/BMP-9, yet is restored with treatment of ND (p<0.001) in Huh7 hepatocytes. ND treatment also significantly raises ferroportin expression without IL-6/BMP-9 induction (p<0.05) (n=4). Error bars represent Standard Error. FIG. 29C shows Western blot of IL-6 (10 ng/mL) and BMP-9 (10 ng/mL) induced HepG2 cells, co-treated with PIs ND (15 µM), and CMK (25 µM). FIG. 29D shows graphical representation of Western blot data, showing significant increase in ferroportin expression in ND treated healthy cells (p<0.05). Ferroportin expression in cells treated with CMK doubled (109%) when compared to IL-6/BMP-9 control (p<0.01). Prominent expression of ferroportin is most dearly observed with ND treated IL-6/BMP-9 induced cells, where expression increased 174% as compared to control (p<0.001) (n=4).

FIG. 30A shows that serum IL-6 concentrations are significantly higher in PG-LPS groups (p<0.0009) but do not differ significantly between the PG-LPS control and treated (p>0.05). FIG. 30B shows that serum BMP-9 concentrations are significantly higher in PG-LPS groups (p<0.0001) but do not differ significantly with treatment (p>0.05). FIG. 30C shows that serum EPO concentrations do not differ between groups (p>0.05).

FIG. 31A shows that HAMP mRNA is up-regulated by inflammation in the liver (p<0.0001). FIG. 31B shows that serum hepcidin is elevated with inflammation but inhibited by PIs (p<0.01). FIG. 31C shows that serum prohepcidin increased slightly by inflammation but is significantly higher when PIs are used to inhibit furin (p<0.05). FIGS. 31D-E show that ferroportin is rapidly degraded in animals with inflammation (p<0.05) but is stabilized with PIs in both control and PG-LPS animal groups (p<0.00001) and (p<0.001) respectively.

FIG. 32A shows that the total iron content in serum is significantly decreased in inflamed animals compared to healthy and PI treated healthy, but the presence of PIs causes a significant increase in total serum iron (p<0.01). FIG. 32B shows that liver iron content dropped in both the healthy PI treated and PG-LPS PI treated groups (p<0.0001 and p<0.01), consistent with elevated levels of ferroportin. FIG. 32C shows that bone marrow iron content is similar in healthy rats but lowest in inflamed rats. Treatment with protease inhibitors produces an elevation in bone marrow iron similar to healthy rats (P<0.05).

FIG. 34A shows furin mRNA from liver. FIG. 34B is a graphical representation of furin liver expression. FIG. 34C shows a Western blot of furin liver expression between treatment groups. Treatment shows no significant interaction of PI treatment, whereas furin is upregulated significantly between control and PG-LPS groups (p<0.01).

FIG. 39A is the red blood cell distribution width and FIG. 39B is the mean corpuscular volume of animals during the course of treatment after PG-LPS inoculation.

DETAILED DESCRIPTION

Figure 1A:
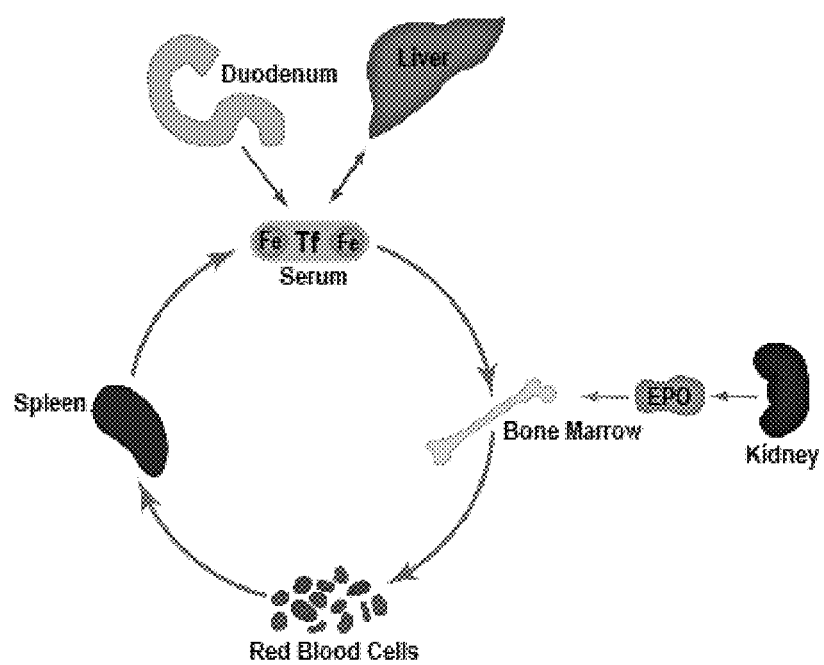
FIG. 1A is a schematic illustration showing iron cycling in mammals, and shows healthy iron cycling between tissues.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Anemia is a medical condition where a decrease in number of red blood cells (RBCs) is usually accompanied with a lower than normal quantity of hemoglobin in the blood. Anemia of chronic inflammation (ACI) is a type of anemia that, commonly occurs in patients with chronic immune activation (Weiss, G. & Goodnough, L. T. Anemia of Chronic Disease. *N. Engl. J. Med.* 352, 1011-1023 (2005); Jr, M. R. Recent developments in the anemia of chronic disease. *Curr. Hematol. Rep.* 2, 116-121 (2003); Da, S. Anemia of chronic disease. *Med. Clin. North Am.* 76, 567-579 (1992)). ACI is characterized by macrophage and liver iron retention triggered by inflammatory cytokines that induce the expression of the master iron regulator hepcidin. Hepcidin is known to regulate iron efflux by binding to ferroportin and initiating endocytosis and degradation of ferroportin causing the iron retention of ACL Hepcidin also regulates iron absorption from the diet as ferroportin is used by the cells lining the intestines to transport, iron into the bloodstream. Hepcidin also degrades this population of ferroportin preventing iron absorption. Hepcidin is cleaved into its active form by the serine protease known as furin.

Iron is a key player for the production of red blood cells. Iron is absorbed into the duodenal enterocytes through DMT1, and then exported into circulation through ferroportin, an iron transport protein. Iron is then transported by transferrin to the bone marrow, where the iron is delivered to erythrocyte precursors to be incorporated into hemoglobin. Excess iron is stored in ferritin, an iron storage protein. When iron is needed for erythropoiesis, iron is released from ferritin into the cytosol, where it is exported through ferroportin into the serum. In ACI, iron stores are normal or high. However, despite normal iron levels in storage, the level of circulating iron is low', which results in a low production of red blood cells.

Hepcidin is the master regulator of iron homeostasis. Hepcidin acts by binding to ferroportin to block the transport (export) of iron. This action leads to iron accumulation in the cell, Hepcidin is expressed in response to inflammation as a signal to sequester iron. However, during periods of chronic inflammation, hepcidin is constitutively expressed, resulting in chronic sequestration of iron. The result is normal or elevated iron stores and decreased blood iron levels.

The proprotein convertase furin is responsible for activating hepcidin. Turin acts by cleaving the inactive precursor prohepcidin into active hepcidin. As described herein, protease inhibitors are used to partially inhibit the activity of furin, thereby blocking the activation of hepcidin from prohepcidin. The inhibition of hepcidin results in the ability of ferroportin to transport iron from the cytosol to the serum, where it is transported by transferrin to the bone marrow for erythropoiesis, and subsequent amelioration of anemia.

Definitions

Unless defined otherwise, technical and scientific terms used herein have the same meaning as commonly understood by one of ordinary skill in the art to which the present disclosure belongs. For purposes of the present disclosure, the following terms are defined below.

As used herein, the term "subject" is an animal, such as a vertebrate, preferably a mammal. The term "mammal" is defined as an individual belonging to the class Mammalia and includes, without limitation, humans, domestic and farm animals, and zoo, sports, or pet animals, such as sheep, dogs, horses, cats or cows. In some embodiments, the subject is mouse or rat. In some embodiments, the subject is human.

As used herein, a "patient in need" or a "subject in need" refers to a subject identified as in need of a therapy or treatment, and refers to a subject susceptible to, at risk of, or presenting with a specified disease, disorder, or condition. In some embodiments, a subject in need is a subject that suffers from or is at risk of developing anemia, including an iron deficiency anemia, a $B_{12}$ deficiency anemia, a folate deficiency anemia, a hemolytic anemic, an aplastic anemia, a glucose-6-phosphate dehydrogenase deficiency anemia, a pernicious anemia, or anemia of chronic inflammation, or combinations thereof. In some embodiments, the subject in needs suffers from anemia of chronic inflammation as a result of an underlying chronic disease. Thus, in some embodiments, the subject in need suffers from a chronic disease, including, for example, an infectious disease, an inflammatory disease, heart disease, kidney disease, cancer, Alzheimer's disease, Parkinson's disease, Human Immunodeficiency Virus (HIV), Hepatitis-C virus (HCV), cytomegalovirus (CMV), Dengue virus, Ebola virus, Lassa virus, West Nile virus, rheumatoid arthritis, vasculitis, sarcoid, inflammatory bowel disease, multiple sclerosis, atherosclerosis, diabetes, congestive heart failure, or combinations of any of the aforementioned diseases. In some embodiments, the subject in need suffers from anemia due to treatment of an underlying disease. For example, in some embodiments, a subject in need suffers from anemia due to chemotherapy treatment.

As used herein, the term "anemia" refers to the condition of having a decrease in the number of red blood cells. In some embodiments, anemia refers to anemia of chronic inflammation, wherein the levels of iron stores may be normal or even high, but the levels of serum iron is low, and the result is low erythropoiesis. In some embodiments, anemia is an iron deficiency anemia, a $B_{12}$ deficiency anemia, a folate deficiency anemia, a hemolytic anemic, an aplastic anemia, a glucose-6-phosphate dehydrogenase deficiency anemia, a pernicious anemia, or anemia of chronic inflammation, or combinations thereof. In some embodiments, anemia of chronic inflammation is the result of an underlying chronic disease. A chronic disease may include, for example, an infectious disease, an inflammatory disease, heart disease, kidney disease, cancer, Alzheimer's disease, Parkinson's disease, Human Immunodeficiency Virus (HIV), Hepatitis-C virus (HCV), cytomegalovirus (CMV), Dengue virus, Ebola virus, Lassa virus, West Nile virus, rheumatoid arthritis, vasculitis, sarcoid, inflammatory bowel disease, multiple sclerosis, atherosclerosis, diabetes, congestive heart failure, or combinations of any of the aforementioned diseases. In some embodiments, the patient suffers from anemia, which is caused by the treatment of another disease. For example, the patient suffers from anemia as a result of chemotherapy treatment for cancer.

Anemia of chronic inflammation (ACI) is prevalent in kidney disease, cancer, autoimmune disorders, inflammatory disorders and infections Inflammatory cytokines trigger the production of an iron regulatory hormone called hepcidin that causes ACI. Hepcidin binds to the iron export protein ferroportin and triggers its endocytosis and degradation. Ferroportin exports iron from intestinal enterocytes into the bloodstream and also facilitates the export of iron stored in the liver and macrophages into serum. When iron exits ferroportin and enters the serum, it is bound by transferrin and delivered to cells that need iron such as the bone marrow that is synthesizing heme for red blood cells. During ACI, anemia results because iron is trapped in iron storage cells or not absorbed from the diet and very little iron is available to be bound by transferrin for delivery to iron deficient cells. This results in iron-deficiency in the bone marrow and prevents the production of heme for red blood cell (RBC) synthesis.

In addition to iron-deficiency in the bone marrow, inflammatory cytokines decrease the production of erythropoietin (EPO), the hormone that triggers the proliferation of RBCs. The kidneys sense serum oxygen levels and when hypoxia is detected, the kidneys express and secrete EPO to stimulate RBC proliferation. However, inflammation inhibits EPO production and secretion into serum.

To treat ACI, patients are given synthetic erythropoiesis stimulating agents (ESAs) and iron supplements. These treatments provide slight improvements to anemia but do not completely alleviate ACI for several critical reasons. First, iron supplements do not efficiently transfer iron to transferrin; instead cells absorb the iron. Once the iron supplement enters the cells the iron is trapped because ferroportin is constantly being degraded by hepcidin. A second problem is called EPO resistance. ESAs signal for erythroblasts to differentiation into RBCs. In ACI, ESAs causes erythroblasts to differentiate. However, without sufficient iron in the bone marrow, the resulting RBCs lack iron in heme and are deficient in oxygen transport.

Thus, as provided herein, the successful treatment of ACI requires several coordinated steps. First, ferroportin must be stabilized so that iron can be properly exported from iron-rich cells or absorbed from the diet. Second, the iron must be properly loaded into transferrin. Third, transferrin must deliver iron to the bone marrow. Fourth, ESAs must be provided with the appropriate timing to stimulate erythroblast differentiation into RBCs when iron is present. To accomplish these goals, the development of hepcidin inhibitors or methods to stabilize ferroportin on the cell surface is required.

The two most clearly identified pathways that trigger the expression of the HAMP gene that encodes for hepcidin are the IL-6 initiated Jak/STAT pathway and the BMP-6 and BMP-9 stimulated SMAD pathway. The understanding of these pathways has prompted the study of the inhibition of the transcription of HAMP by inhibiting BMP receptors with dorsomorphin and its derivatives or inhibiting serum BMP levels using a soluble hemojuvelin domain fused with immunoglobulin Fc, These methods have produced recovery of iron mobilization and redistribution by lowering serum hepcidin levels and increasing the stability of ferroportin on the exterior of iron rich cells, which successfully restores hemoglobin and hematocrit levels.

Sasu et al. targeted hepcidin in the serum with antibodies that eliminate hepcidin from serum as a method to increase ferroportin levels (Sasu, B. J. et al. Anti-hepcidin antibody treatment modulates iron metabolism and is effective in a mouse model of inflammation-induced anemia. *Blood* 115, 3616-3624 (2010)). Anti-hepcidin antibodies decrease serum hepcidin levels and increase serum iron levels but does not allow the restoration of hemoglobin and hematocrit levels until the anti-hepcidin antibody is co-administered with ESAs. Related efforts target the IL-6 receptor with an antibody such as tocilizumab to treat Castleman disease (Song, S.-N. J. et al. Down-regulation of hepcidin resulting from long-term treatment with an anti-IL-6 receptor antibody (tocilizumab) improves anemia of inflammation in multicentric Castleman disease. *Blood* 116, 3627-3634 (2010)). In Castleman disease, EL-6 is unregulated and overexpressed causing chronic inflammation. Blocking the inflammatory signal of IL-6 allows the patients to recover from ACI.

In contrast to inhibiting BMP or IL-6 signaling or targeting hepcidin or IL-6 receptors with antibodies, a method for inhibiting hepcidin production and activation is provided herein. Hepcidin is synthesized in a precursor form called prohepcidin that must be cut by a protease called furin before it folds into its active conformation that binds to and degrades ferroportin. Through the use of computational modeling and in silico molecular docking, along with in vitro fluorogenic assays, which can optionally be accomplished using purified protein, inhibiting furin prevents the cleavage of prohepcidin to hepcidin. In some embodiments, a method of inhibiting furin in tissue culture is provided. In some embodiments, the tissue culture may include Huh7 hepatocytes, HepG2 hepatocytes, or any other tissue culture amenable to the determination of furin expression. In some embodiments, a method of inhibiting furin using an animal model is provided. In some embodiments, HIV protease inhibitors with high affinity to furin halt the processing and activation step where prohepcidin is cleaved to produce hepcidin. Thus, as provided herein, furin is a target for restoring iron mobilization through ferroportin. As described herein, protease inhibitors prevent furin from cleaving prohepcidin to hepcidin in order to restore iron to the bone marrow, and in combination with erythropoiesis stimulating agents provide a treatment for ACI.

As used herein, the term "treatment" refers to an intervention made in response to a disease, disorder or physiological condition manifested by a subject, particularly a subject suffering from or at risk of developing anemia. The aim of treatment may include, but is not limited to, one or more of the alleviation or prevention of symptoms, slowing or stopping the progression or worsening of a disease, disorder, or condition and the remission of the disease, disorder or condition. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. In addition, those in need of treatment are those suffering from anemia caused by the treatment of another disease. For example, in some embodiments treatment may enhance or reduce the activity of furin in the subject, thereby to reduce, alleviate, or eradicate the symptom(s) of the disease(s). Furthermore, in some embodiments, the term "treating" refers to inhibiting or inhibiting the development or progression of a disease or disorder.

As used herein, "susceptible" and "at risk" refer to having little resistance to a certain disease, disorder or condition, including being genetically predisposed, having a family history of, and/or having symptoms of the disease, disorder or condition.

As used herein, the term "reducing" in relation to a particular trait, characteristic, feature, biological process, or phenomena refers to a decrease in the particular trait, characteristic, feature, biological process, or phenomena. The trait, characteristic, feature, biological process, or phenomena can be decreased by 5%, 10%, 15%, 20%, 25%, 30%, 35%, 40%, 45%, 50%, 55%, 60%, 65%, 70%, 75%, 80%, 85%, 90%, 95%, 100% or greater than 100%.

As used herein, the term "prevention" refers to any activity that reduces the burden of the individual later expressing disease symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications.

Some embodiments provided herein related to administering a composition that includes one or more protease inhibitors. In some embodiments, the one or more protease inhibitors includes amprenavir, atazanavir, boceprevir, darunavir, fosamprenavir, indinavir, lopinavir, nelfinavir, ritonavir, saquinavir, simeprevir, or tipranavir. In some embodiments, the composition includes one or more protease inhibitors including darunavir, nelfinavir, or ritonavir. In some embodiments, the one or more protease inhibitor is administered in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 mg, or an amount within a range defined by any two of the aforementioned values. In some embodiments, the one or more protease inhibitors is administered five times daily, four times daily, three times daily, twice daily, once daily, once weekly, or once monthly, or a value within a range defined by any two of the aforementioned values.

In some embodiments, the composition includes darunavir. In some embodiments, darunavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, or 800 mg, or an amount within a range defined by any two of the aforementioned values. In some embodiments, darunavir is present in an amount of 800 mg. In some embodiments, darunavir is present in an amount of 20 mg. In some embodiments, darunavir is present in an amount of 5 mg.

In some embodiments, the composition includes nelfinavir. In some embodiments, nelfinavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, or 2500 mg, or an amount within a range defined by any two of the aforementioned values. In some embodiments, nelfinavir is present in an amount of 2500 mg. In some embodiments, nelfinavir is present in an amount of 45 mg. In some embodiments, darunavir is present in an amount of 10 mg.

In some embodiments, the composition includes ritonavir. In some embodiments, ritonavir is present in an amount of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 mg, or an amount within a range defined by any two of the aforementioned values. In some embodiments, ritonavir is present in an amount of 100 mg. In some embodiments, ritonavir is present in an amount of 50 mg. In some embodiments, ritonavir is present in an amount of 1 mg.

In some embodiments, the composition includes both darunavir and nelfinavir. In some embodiments, darunavir and nelfinavir act synergistically, and thus, a lower amount of each of darunavir and nelfinavir is adequate for administration to a subject in need, than if either of darunavir or nelfinavir is administered alone. Accordingly, in some embodiments, the composition including both darunavir and nelfinavir includes darunavir in an amount of 5 mg and nelfinavir in an amount of 10 mg. In some embodiments, the composition including darunavir and nelfinavir is administered once daily.

In some embodiments, the composition includes darunavir, nelfinavir, or ritonavir, or any combination thereof. In some embodiments, ritonavir acts to inhibit cytochrome P450 enzyme, which provides for better action of the concomitantly administered protease inhibitors.

Routes of administering the composition including one or more protease inhibitors include, but are not limited to, intravenous, intramuscular, subcutaneous, intraarticular, oral, topical, intradermal, transdermal, subdermal, parenteral, rectal, spinal, or epidermal administration. In some embodiments, the composition is administered orally. In some embodiments, the composition is administered in combination with a pharmaceutically acceptable carrier suited for the mode of administration.

In some embodiments, the compositions include a pharmaceutically acceptable carrier. "Pharmaceutically acceptable" carriers are ones which are nontoxic to the cell or subject being exposed thereto at the dosages and concentrations employed. "Pharmaceutically acceptable" earners can be, but are not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also include one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counter ions such as sodium, and nonionic surfactants such as Tween™, polyethylene glycol (PEG), and Pluronics™. Auxiliary, stabilizer, emulsifier, lubricant, binder, pH adjustor controller, isotonic agent and other conventional additives may also be added to the carriers.

The pharmaceutically acceptable or appropriate carrier may include other compounds known to be beneficial to an impaired situation of the GI tract, (e.g., antioxidants, such as Vitamin C, Vitamin E, Selenium or Zinc); or a food composition. The food composition can be, but is not limited to, milk, yogurt, curd, cheese, fermented milks, milk based fermented products, ice-creams, fermented cereal based products, milk based powders, infant formulae, tablets, liquid bacterial suspensions, dried oral supplement, or wet oral supplement.

As used herein, the term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain molecules, and antibody fragments (e.g., Fab or $F(ab^1)_2$, and Fv). For the structure and properties of the different classes of antibodies, see e.g., Basic and Clinical Immunology, 8th Edition, Daniel P. Sties, Abba I. Ten and Tristram G, Parsolw (eds), Appleton & Lange, Norwalk, Conn., 1994, page 71 and Chapter 6.

As used herein, "chemotherapy" refers to administering one or more cytotoxic anti-neoplastic drugs to a cancer patient as part of a standardized treatment regimen.

Numerous chemotherapy drugs are known. In some embodiments, a cancer chemotherapy drug may include nitrogen mustards, nitrosoruaas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda, and pharmaceutically acceptable salts, acids or derivatives of any of the above, or any combination thereof.

In some embodiments, cancer chemotherapy drugs may include alkylating agents, such as Thiotepa and cyclosphosphamide; alkyl sulfonates, such as Busulfan, Improsulfan and Piposulfan; aziridines, such as Benzodopa, Carboquone, Meturedopa, and Uredopa; ethylenimines and methylamelamines, including altretamine, triethylenemelamine, trietylenephosphoramide, triethylenethiophosphaoramide and trimethylolomelamine; nitrogen mustards, such as Chlorambucil, Chlomaphazine, Cholophosphamide, Estramustine, Ifosfamide, mechlorethamine, mechlorethamine oxide hydrochloride, Melphalan, Novembiehin, Phenesterine, Prednimustine, Trofosfamide, uracil mustard; nitroureas, such as Cannustine, Chlorozotocin, Fotemustine, Lomustine, Nimustine, and Ranimustine; antibiotics, such as Aclacinomysins, Actinomycin, Authramycin, Azaserine, Bleomycins, Cactinomycin, Caliehearaicin, Carabicin, Carminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromyein, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues, such as Denopterin, Methotrexate, Pteropterin, and Trimetrexate; purine analogs, such as Fludarabine, 6-mercaptopurine, Thiamiprine, and Thioguanine; pyrimidine analogs, such as Ancitabine, Azacitidine, 6-azauridine, Carmofur, Cytarabine, Dideoxyuridine, Doxifluridine, Enocitabine, Floxuridine, and 5-FU; androgens, such as Calusterone, Dromostanolone Propionate, Epitiostanol, Rnepitiostane, and Testolactone; anti-adrenals, such as aminoglutethimide, Mitotane, and Trilostane, folic acid replenisher, such as frolinic-acid, aceglatone; aldophosphamide glycoside; aminolevulinic acid; Amsacrine; Bestrabucil; Bisantrene; Edatraxate; Defofamine; Demecolcine; Diaziquone; Elfomithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone, 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide, thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Chlorambucil; Gemcitabine; 6-thioguanine; Mercaptopurine; Methotrexate; platinum analogs, such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylomithine (DMFO); retinoic acid; Esperamicins; Capecitabine; and pharmaceutically acceptable salts, acids or derivatives of any of the above. Also included are anti-hormonal agents that act to regulate or inhibit hormone action on tumors, such as anti-estrogens including for example Tamoxifen, Raloxifene, aromatase inhibiting 4(5)-imidazoles, 4 Hydroxytamoxifen, Trioxifene, Keoxifene, Onapristone. And Toremifene (Fareston); and anti-androgens such as Flutamide, Nilutamide, Bicalutamide, Leuprolide, and Goserelin, and pharmaceutically acceptable salts, acids or derivatives of any of the above, or any combination thereof.

Anemia

Anemia is a medical condition where a decrease in the number of red blood cells (RBCs) is usually accompanied with a lower than normal quantity of hemoglobin in the blood. The primary function of the red blood cell is to deliver oxygen to the tissues. Anemia impairs the ability of the blood to efficiently transport oxygen to body tissue, usually leading to hypoxic (low oxygen) conditions in vital organs.

Patients with severe or prolonged anemia are easily fatigued, appear pale, portray dyspnea (shortness of breath), and have a tendency to develop irregular heartbeats known as palpitations. These symptoms involve physiologic compensation, including decreased hemoglobin oxygen affinity, increased cardiac output, and redistribution of blood flow.

Characterizing anemia is often sub-classified into three differing categories—pathogenesis, red blood cell morphology, and clinical presentation. Pathogenic mechanisms involve inappropriate over-production of erythrocytes, or loss of erythrocytes due to hemolysis or bleeding. Further classified as being regenerative versus hypo-regenerative. Polycythemia is a disease state in which the proportion of blood volume occupied by the red blood cells increases. Red blood cell morphology relates to morphologic characteristics within the complete blood count (CBC), identifying the anemia as being microcytic, macrocytic, or normocytic. Analytical parameters provided by automated hematology analyzers include mean corpuscular volume (MCV) and red blood cell distribution width (RDW).

MCV is measured as the average volume of a red blood cell (normal range: 82-98 fL) reported in femtoliters ($10^{-15}$ L). RDW is a measure of the variation of red blood cell size. RBCs are usually 6-8 pm in diameter. In humans, the normal RDW range is 11.5-14.5%. Levels of reticulocytes (immature RBCs) compose about 1% of the total RBC in a healthy individual. Higher percentages of reticulocytes are attributable to anemia.

Clinical presentation involves other analysis useful in anemia diagnosis. Serum levels of iron, urea, creatinine, vitamin B12, folate, and bilirubin are used as important indicators. The levels of protein involved in iron metabolism within serum can also be indicative of iron status and anemia, including transferrin, soluble transferrin receptor (sTfR), and ferritin.

Anemia of Chronic Inflammation (ACI)

ACI is the most frequent anemia in hospitalized patients, and is associated with increased morbidity and mortality. In the U.S., more than 117 million persons live with at least one chronic illness. Over 40% of these cases have resulted in significant debilitating anemia.

Chronic diseases that lead to abnormal activation of the immune response and eventually ACI, include infectious and inflammatory diseases, heart disease, kidney disease, and cancer. The major patient population statistics for ACI is provided in Table 1,

TABLE 1

Anemia Statistics for Patient Populations

| Patient Population | Anemia Statistics |
|---|---|
| Cancer Patients | 80% of chemotherapy patients have severe anemia |
| | 8 million people die from cancer each year worldwide |
| Chronic Kidney Disease (CKD) | 26 million Americans have CKD12 |
| | 28% of mild CKD patients are anemic |
| | 87% of severe CKD patients are anemic |
| Critically Ill Patients | 50% of patients in intensive care unit are anemic |
| | 75% of long-stay critically ill patients are anemic |
| Diabetes | 25.8 million Americans have diabetes |
| | 33% of type 1 diabetic develop CKD after 15 years |
| Elderly | 50% of persons in nursing homes have anemia |
| | Anemic elderly are twice as likely to be hospitalized for falls |
| Heart Disease | 17-48% of anemic patients experience heart failure |
| | 43% of hospitalized heart attack patients have anemia |
| Hepatitis C Virus (HCV) Patients | 3.2 million Americans have chronic HCV infection |
| | 67% of hepatitis C patients have treatment-related anemia |
| HIV/AIDS | 75-80% of people with AIDS have anemia |
| Inflammatory Bowel Disease (IBD) Patients | More than 1 million people in US have IBD |
| | 17-41% of all types of IBD patients have anemia |

TABLE 1-continued

Anemia Statistics for Patient Populations

| Patient Population | Anemia Statistics |
|---|---|
| Rheumatoid Arthritis | 2.1 million Americans have rheumatoid arthritis<br>30-60% of rheumatoid arthritis patients have anemia |

*All values are representative of passing World Health Organization (WHO) criteria for the diagnosis of anemia.

Healthy levels of hematocrit (HOT) are about 45% for men, and 40% for women. Healthy hemoglobin (Hb) values range from 15-18 g/dL. ACI is a mild to moderate anemia where hematocrits can range between 30% and 40%, and Hb levels range between 9-13 g/dL. It is common, however, that hematocrit will drop below 25%. Marginal normocytic anemia is initially observed, and will later progress into microcytic anemia, as severity of the underlying disease progresses.

Despite having adequate iron stores, subjects with ACI elicit low serum iron concentrations and a high erythrocyte sedimentation rate. ACI has similarities with other types of anemia, where the red blood cells show hypochromic microcytic characteristics similar to iron deficient anemia.

ACI is sometimes confused with iron deficiency anemia (IDA). In both forms of anemia, levels of iron circulating in the blood are low. Circulating iron is necessary for supplying iron for red blood cell production in the bone marrow. Low blood iron levels occur in IDA because levels of the iron stored in the tissues are depleted. In ACI, however, iron stores are normal or high. Low blood iron levels occur in ACI, despite normal iron stores. Microcytic cells are usually present in both disorders, despite being more prominent in true iron deficiency.

Transferrin is another biomarker used in diagnosing anemia. Transferrin is a serum protein known for its ability to transport iron throughout the body. During iron-deficiency anemia, transferrin levels in serum are elevated. With ACI, transferrin levels drop.

Soluble transferrin receptor tests can be useful to differentiate between IDA and ACI. The soluble transferrin receptor is much less affected by inflammation than serum ferritin, and so results will be high in IDA and usually low to normal in ACI. The ratio of the soluble transferrin receptor to the logarithm of the serum ferritin concentration can be measured to more clearly distinguish between ACI and IDA. A study reported median values for patient groups of ACI as 0.5-0.8, where IDA patients range 5.0-6.2, and ACD/IDA 2.8-3.4.

Serum ferritin is also a biomarker used to distinguish between ACI and IDA. Ferritin levels correlates with iron content in the bone marrow and serum ferritin concentrations can be used to predict iron status in an individual. This method works well for healthy individuals. However, ferritin is known to be an acute-phase reactant, meaning it can be elevated during the onset of inflammation. Therefore, elevated serum ferritin levels do not accurately correlate with bone marrow iron content if the patient has inflammation. Often C-reactive protein is measured along with serum ferritin content to determine if the serum ferritin content accurately predicts iron status.

Total iron-binding capacity (TIBC) is a medical laboratory-test that measures the blood's capacity to bind iron with transferrin. TIBC values are used as an indirect measurement to determine the iron content in the blood. These values are reported as being significantly low with ACI. This is due to iron not being as easily accessible, as the body stores the iron intracellularly. As iron stores deplete, TIBC values will increase. When iron stores are elevated, the TIBC will decrease. Normal values for TIBC range from 240-400 µg/dL, In IDA, the TIBC is higher than 400-450 µg/dL because stores are low. In ACI, the TIBC is usually below normal because iron stores are elevated.

As ACI develops in inflammatory diseases, increased levels of cytokines are found in such patients. Direct correlations have been previously shown between cytokine concentrations and the degree of anemia.

Several processes are involved in the pathogenesis of ACI. Stunted erythropoiesis and inflammatory cytokines are implicated in all of them. These include impaired RBC survival, impaired proliferation of erythroid progenitor cells, blunted erythropoietin response, iron-restricted erythropoiesis and most importantly, impaired mobilization of reticuloendothelial system (RES) iron stores due to the regulation of the peptide hormone hepcidin.

Anemic patients with rheumatoid arthritis (a common model for ACI) show an inverse relationship between cytokine levels and RBC survival, suggesting that increased erythrocyte destruction is due to the activated immune response. In addition, increased erythrophagocytosis during inflammation leads to a decreased erythrocyte half-life.

Impaired proliferation of erythroid precursors is evident in ACI. Cytokines of inflammation inhibit the proliferation and differentiation of erythroid burst-forming units, which are the precursors to mature RBCs. Interferon-$\alpha$, -$\beta$, and -$\gamma$ along with the interleukin and TNF families of cytokines are particularly potent. Cytokine-mediated apoptosis, formation of ceramide, and down-regulation of erythropoietin have all been claimed as mechanisms. Cytokines can also form labile free radicals such as nitric acid or superoxide. Inhibition is reflected by lowered Hb and reticulocytes concentrations.

Erythrocyte proliferation is regulated to a large extent by erythropoietin (EPO), which is produced in the kidney. Expression of EPO can be inversely related to tissue oxygenation and fib levels. During ACI, EPO tends to stay at normal to low levels. This is in contrast to IDA, where EPO levels dramatically increase. The responsiveness of erythroid precursors to EPO is related to the severity of the disease involved.

Restricted iron availability can be illustrated during the intermediate step of heme production, where iron is incorporated into protoporphyrin IX. Protoporphyrin IX is a precursor to heme. Zinc is a known alternative to iron, and in circumstances where iron is unavailable, zinc protoporphyrin is readily increased. In ACI, zinc protoporphyrin levels are increased, indicating insufficient iron levels. The presence of zinc in hemoglobin produces hypochromic RBCs, a true marker of IDA.

Iron Homeostasis

Major underlying mechanisms of restricted iron availability in ACI include the disruption of iron absorption, iron mobilization from storage tissue, and the transport of iron from the site of absorption and storage to the bone marrow Inflammatory cytokines and cells of the RES system interfere with the body's ability to use stored iron and absorb iron from the diet. This iron then becomes unavailable for efficient erythropoiesis, as it is sequestered in macrophages and other cells.

An average person stores 1-2 g of iron within the blood and tissue. Normally 1-2 mg of iron is lost daily (through the shedding of intestinal enterocytes). This is replenished daily, as 1-2 mg is again absorbed through the gut from the diet.

Senescent erythrocytes are recycled daily by macrophages, recycling 20 mg of iron daily. Iron absorbed from the diet is absorbed through the intestines into duodenal enterocytes. This process is aided with the help of the protein divalent metal transporter-] (DMT1). DMT1 is highly expressed at the apical pole of enterocytes, and is best characterized for its ability to transport ferrous iron ($Fe^{2+}$) into enterocytes.

Ferroportin-1 is an intermembrane protein iron exporter also known as S1c40a1. Ferroportin is found on the surface of cells that store or transport iron including enterocytes in the duodenum, hepatocytes in the liver, and macrophages. Iron is absorbed into the duodenal enterocytes through DMT1, before being exported into the circulation via ferroportin.

Iron is then transported by transferrin to the bone marrow. Each individual transferrin protein is capable of carrying two ferric iron ($Fe^{3+}$) atoms. When iron arrives at the bone marrow, it is delivered to erythrocyte precursors to be incorporated into Hemoglobin (Hb). Circulating macrophages phagocytize senescent erythrocytes, recycling iron, and storing it in ferritin. Ferritin is capable of storing about 4,500 iron atoms during times of iron excess.

When iron is needed for cellular metabolic functions including erythropoiesis, macrophages are able to release the iron in ferritin into the cytosol where it is exported through ferroportin into the serum where it is bound to transferrin. This allows for restoration of serum and cellular iron levels when needed.

Hepcidin

Under inflammatory conditions where the immune system is chronically activated, hepcidin levels are elevated well above basal levels. Hepcidin is a small peptide with the ability to bind and signal endocytosis of the iron exporter protein ferroportin. In doing so, hepcidin is able to negatively regulate enterocyte iron absorption, and iron release from hepatocytes and macrophages.

Hepcidin is a cysteine rich 25 amino acid peptide that plays a major role in iron metabolism. Hepcidin is synthesized in liver tissue cells known as hepatocytes. Initially it is formed intracellularly from the HAMP gene as an 84 amino acid (aa) precursor named preprohepcidin. Enzymatic cleavage converts this aa chain into a 64 aa long prohormone known as prohepcidin, and is then cleaved again into the mature biologically active 25 aa form known as hepcidin. Hepcidin can then be excreted into the blood serum and circulated to various tissues, before being filtered by the glomerulus and excreted in the urine.

Hepcidin is most commonly found as hepcidin-25, but shorter forms have also been characterized. These include hepcidin-22 and hepcidin-20. The 22 aa isoform has currently only been detected in urine, suggesting that it may be a degradation product of hepcidin-25.

Although liver is the main source of hepcidin, hepcidin mRNA and protein have been found in other cells and tissues. Heart, kidney, retina, monocytes and macrophages, splenocytes, pancreatic p cells, and adipocytes have also been observed to express mature hepcidin. However, basal expression of hepcidin in these tissues is much lower than the basal expression rate of hepcidin in the liver. Basal levels of hepcidin in the serum normally range form 20-30 ng/mL, in healthy individuals, whereas in circumstances of chronic inflammation can reach 200-250 ng/mL.

Figure 1B:
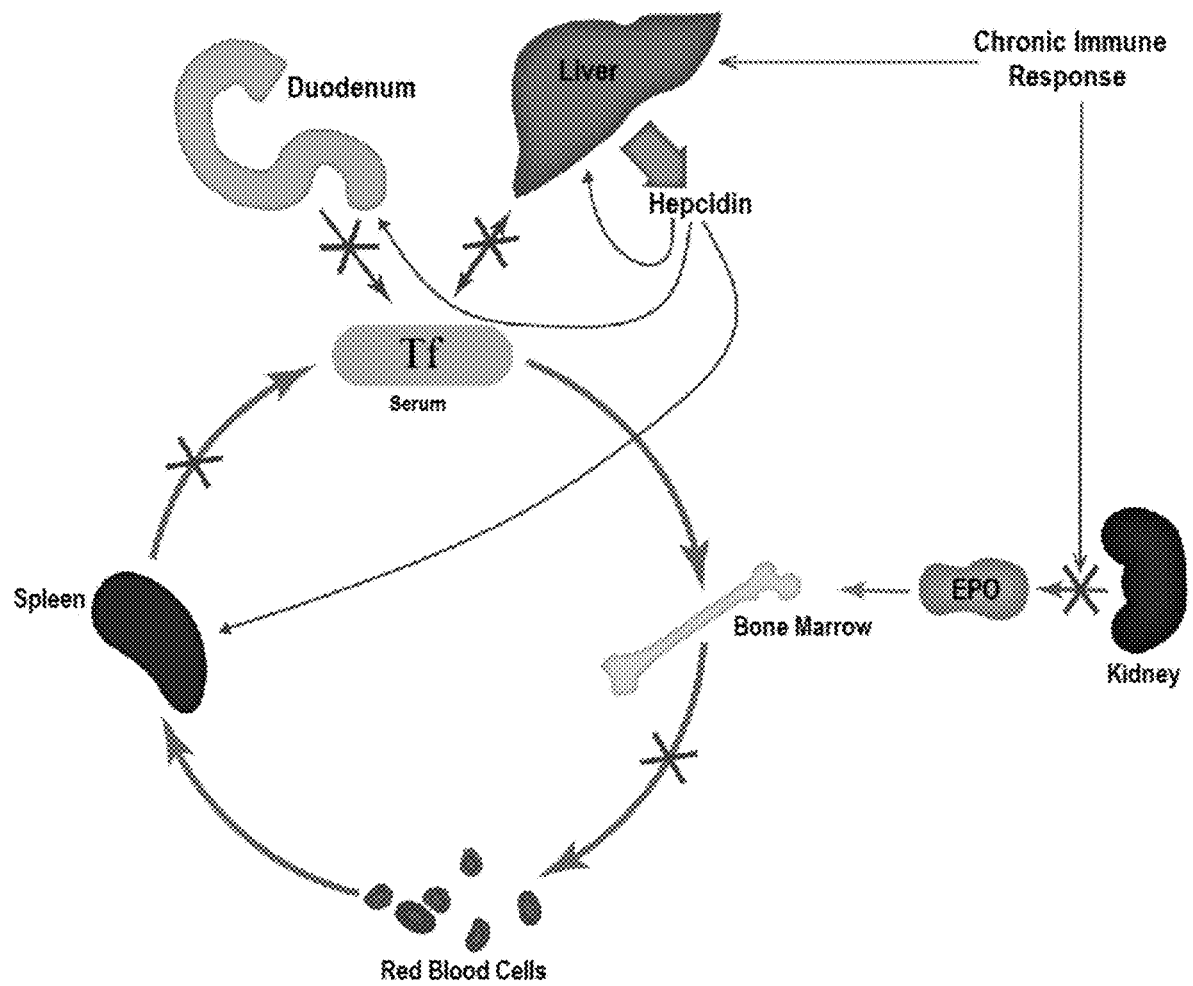
FIG. 1B is a schematic illustration showing iron cycling in mammals during chronic immune activation, showing the mechanism of cytokine release into the serum for the activation of hepcidin production. Hepcidin inhibits iron export from various tissues by triggering endocytosis of ferroportin within hepatocytes of the liver, macrophages in the spleen, and enterocytes in the duodenum.

Production of hepcidin is regulated by the need of iron and erythropoiesis, as is critical regarding anemia (FIG. 1A). During active erythropoiesis hepcidin production is suppressed, making more iron available for the synthesis of heme for hemoglobin (FIG. 1B).

Hepcidin is the master negative regulator of iron homeostasis and rapidly responds to iron supply and demand, as well as to inflammation and erythropoietic activity. Its synthesis is inhibited by iron deficiency, and yet stimulated by inflammation. The hepcidin-ferroportin iron disorders including iron over-load and iron restricted anemia's, are significantly affected by even minute changes at the hepcidin-ferroportin axis. These minute changes provide a potentially promising environment to which minor pharmacological changes have greater therapeutic results.

The molecular target of hepcidin is the cellular iron exporter ferroportin. Ferroportin is a 571 aa intermembrane protein that controls iron efflux. Ferroportin exports iron from the enterocytes into the plasma. It also supplies iron from macrophages of the spleen and liver that recycle senescent blood cells, and from hepatocytes involved in iron storage. When the concentration of hepcidin is low, ferroportin levels are uninhibited. When bioactive hepcidin binds to ferroportin, active induction of endocytosis and consequent degradation of the hepcidin-ferroportin complex occurs. As ferroportin is degraded, iron export from the cell is impeded, and disruption in iron homeostasis throughout the entire organism occurs. Iron is thereby sequestered within the macrophage, enterocytes, or hepatocyte, and inhibited from transport to vital organs and tissues.

Figure 2:
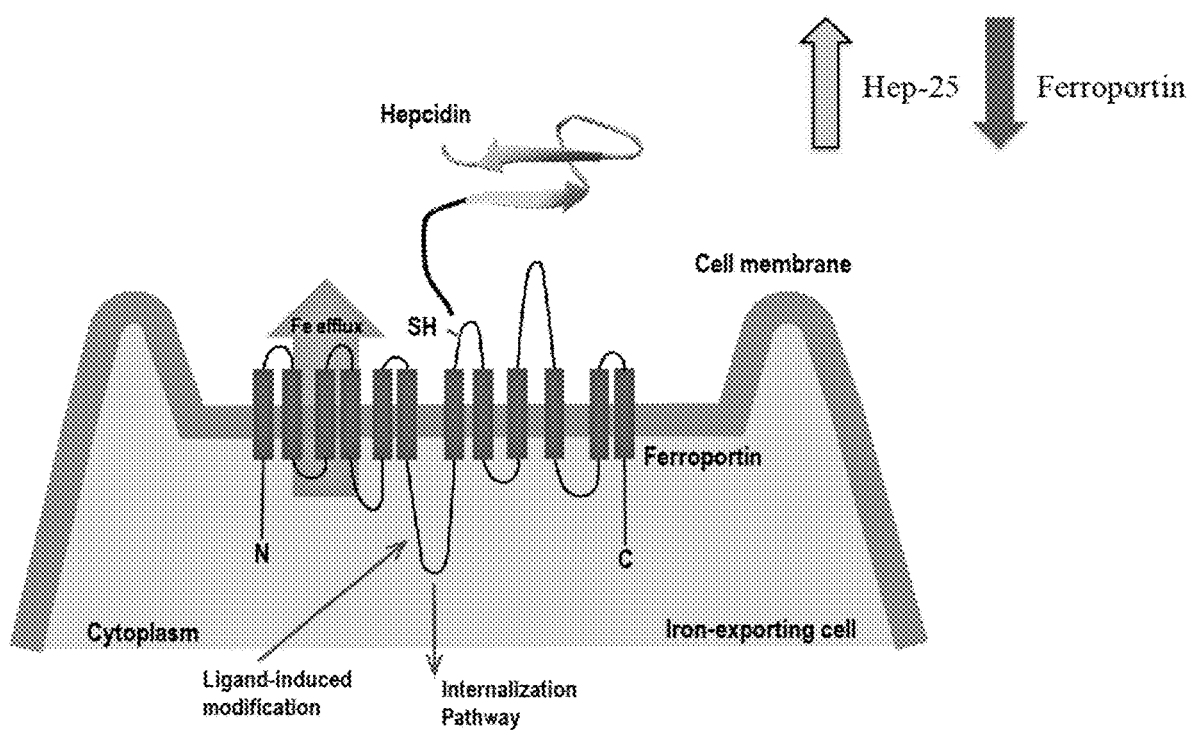
FIG. 2 is a schematic illustration showing hepcidin binding to ferroportin. Hepcidin binding region is located within the first five amino acids (DTHFP). Hepcidin binds to an outer loop of ferroportin (C326) to induce endocytosis and degradation of the hepcidin-ferroportin complex. When hepcidin-25 levels increase, ferroportin levels decrease, and when hepcidin-25 levels decrease, ferroportin levels increase.

Hepcidin acts as a ligand for ferroportin. When hepcidin binds to ferroportin, a conformational change occurs, leading to induced endocytosis and degradation of the hepcidin-ferroportin complex (FIG. 2). Binding to ferroportin is dependent on an extracellular loop containing a cysteine (C326). When this residue is mutated, iron efflux will continue despite the presence of hepcidin. Subjects suffering from the heterozygous mutation of this residue (C326S) quickly develop severe iron overload because iron absorption through the enterocytes continues to occur without regulation or inhibition.

Hepcidin-induced loss of ferroportin decreases iron transfer and availability to serum. This occurrence is known as hypoferremia, as hepcidin is able to regulate the concentration of ferroportin on the cell surface. Cell experiments where ferroportin has been expressed or overexpressed, show that small changes in hepcidin concentration drastically inhibit iron efflux.

To coordinate iron absorption from the apical membrane of enterocytes with ferroportin on the basolateral surface, several key factors are involved.

First, the stimulatory effect for DMT1 can be removed. Cellular iron is a cofactor of oxygen sensing prolyl hyroxylases. These induce the hydroxylation of hypoxia-inducible factor (HIF-1α), leading to degradation, HIF1α is no longer able to stimulate transcription of DMT1.

Second, as hepcidin binds to ferroportin, cellular iron increases because of diminished export. Increased cellular iron inactivates iron regulatory proteins (IRP1 and IRP2) that normally bind to the 3' iron regulatory' element (IRE) of DMT1 mRNA. This destabilizes the DMT-1 mRNA, leading to less transcription, and less expression of DMT1. In contrast, the IRPs are released from the mRNA encoding ferritin and ferritin synthesis increases. This leads to sequestration of iron in ferritin so that free cytosolic iron is not available for export into the bloodstream by ferroportin. Eventually the enterocytes are sloughed off the intestinal wall and excreted with the iron sequestered inside ferritin.

Third, DMT1 is down regulated by hepcidin through activation of ubiquitin ligases. As hepcidin binds to ferroportin, ubiquitin ligases distribute throughout the cytoplasm and consequently stimulate degradation of DMT1, Other apical proteins may be affected as well. Ubiquitination of other enterocyte transporters are currently being investigated.

Hepcidin concentrations are significantly increased with patients having chronic inflammatory disorders Inflammatory secretion of IL-6 and BMPs, as well as other cytokines contribute to anemia of chronic inflammation.

Liver and serum iron stores regulate hepcidin transcription and secretion through many different pathways. One of the major pathways to which hepcidin transcription is upregulated, occurs with inflammation. Cytokines known as bone morphogenic proteins (BMPs) are elevated in serum by inflammation and bind to hepatocytes and activate the BMP receptor and its corresponding pathway.

BMPs represent a superfamily of transforming growth factor β (TGF-β) ligands, which share common 'cross-talk' or transduction. Bone morphogenic protein-6 and -9 (BMP-6 and BMP-9) and interleukin-6 (IL-6) are two of the stimulatory cytokines known to induce production of actively mature hepcidin. BMP-6, BMP-9, and IL-6 promote the transcription of HAMP through signaling cascades. The gene HAMP encodes for preprohepcidin.

During conditions of chronic inflammation, where the immune response is chronically activated, BMP-9 cytokine release is elevated. BMP-9 is known to mediate hemojuvelin (HJV) docking to the bone morphogenic protein receptor (BMP-R), and activate phosphorylation of cascade proteins known as SMADs.

IL-6 induced expression of hepcidin begins with IL-6 binding to the intermembrane glycoprotein 130 (gp130) receptor, signaling tyrosine janus kinase (Jak) phosphorylation of signal transducer and activator of transcription-3 (STAT-3). Upon phosphorylation, STAT-3 forms a dimer with another phosphorylated STAT-3 before translocating into the nucleus and activating HAMP.

HAMP is transcribed and then concurrently translated into an 84 amino acid chain precursor known as preprohepcidin. Preprohepcidin is cleaved by a protease along its multi-basic sequence motif into prohepcidin, and again into hepcidin. Mature hepcidin is 25 amino acids in length, and at which point is actively excreted from the cell and able to bind ferroportin-1.

Figure 3:
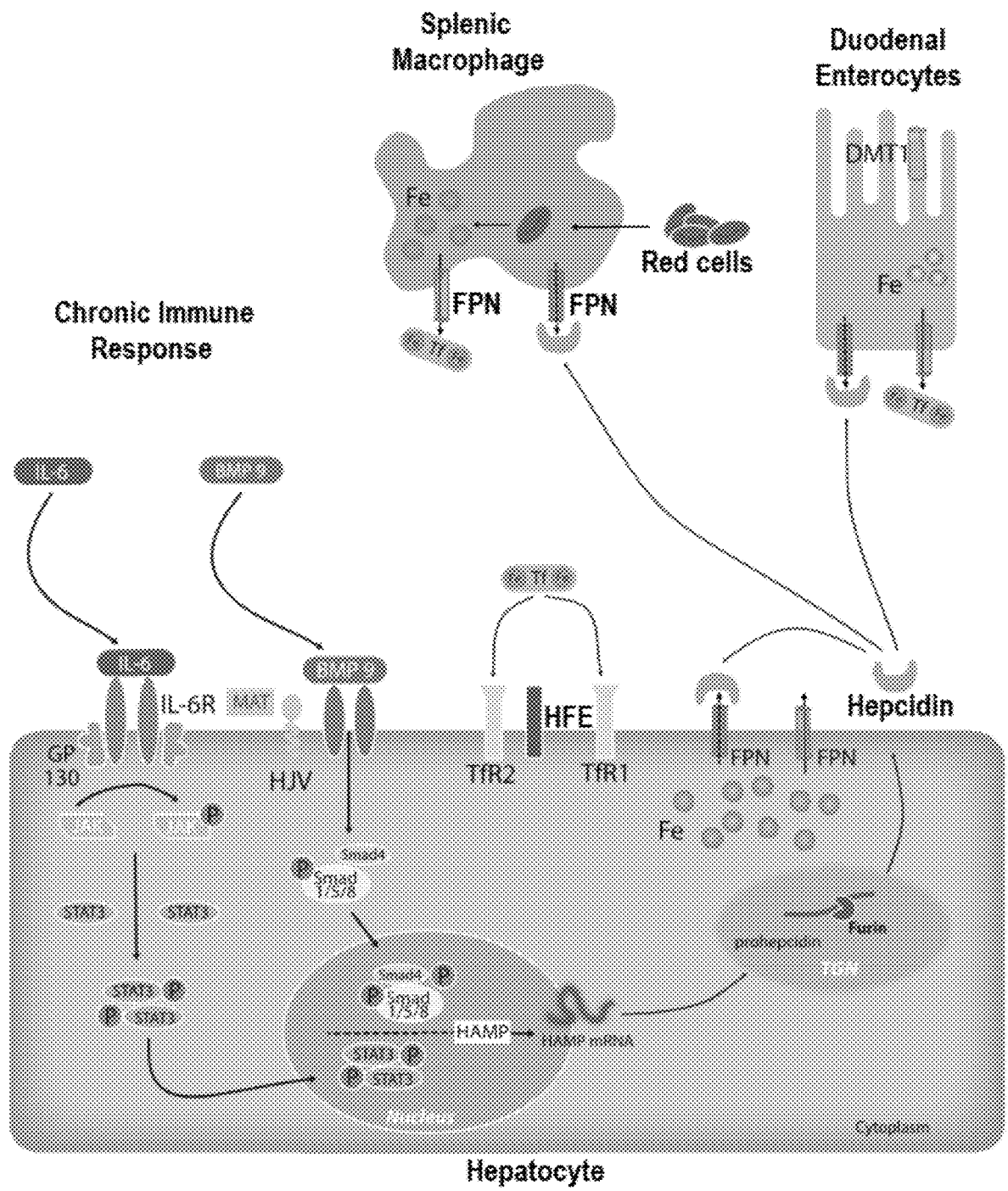
FIG. 3 is a schematic illustration depicting an overview of proteins involved in stimulating hepcidin production. During chronic immune activation, release of cytokines IL-6, BMP-6, and BMP-9 activate HAMP gene expression, increasing the concentration of hepcidin. Hepcidin is exported out of the cell inducing endocytosis of ferroportin in different cells, perpetuating anemia.

BMP receptors facilitate the activation of SMAD proteins (FIG. 3). SMADs are intracellular cascade proteins able to activate downstream transcription. Upon phosphorylation, SMADs can act as transcription regulators for the HAMP gene, which encodes hepcidin. Signaling begins when ligands bind to complexes of two type I and two type II receptors. Type II phosphorylate type I receptors, which then phosphorylate SMADs (Smad1, Smad5, Smad8).

Although serum and liver iron accumulation alone can activate the BMP receptor and its SMAD 1/5/8 pathway to increase hepcidin transcription, chronic inflammatory situations cause high concentrations of BMPs to circulate in the serum. During these situations, the HAMP gene is activated above and beyond physiologically healthy constitutive levels.

A co-receptor protein known as hemojuvelin (HJV) also acts to regulate BMP signaling. HJV is essential for dietary iron sensing, and its mutation leads to severe iron overload. Although the exact function of HJV is still unclear, HJV mutations cause severe hepcidin deficiency resulting in juvenile hemochromatosis.

Matriptase (MT-SP1) is an integral membrane trypsin-like serine protease that is a member of the type II transmembrane serine proteases (TTSP). Matriptase-2, has been shown to cleave and activate HJV in liver tissue, and have an inhibitory effect on hepcidin promotion. Expression of matriptase-2 mutants in zebrafish results in anemia, confirming its role in iron metabolism and its interaction with HJV.

Inflammation has been shown to increase hepcidin synthesis through interleukin-6 (IL-6). EL-6 is an interleukin (cytokine protein family) secreted by T cells and macrophages to stimulate an immune response. IL-6 activates hepcidin production through the Jak/STAT signaling pathway. IL-6 acts as the ligand, and when bound to the glycoprotein 130 (gp130) receptor, activates janus kinases (JAKs). JAKs are then able to phosphorylate and activate Signal Transducers and Activators of Transcription (STATs), particularly STAT3. Activated STAT3s form dimers, translocate to the nucleus, bind to specific response elements in promoters of target genes, and transcriptionally activate these genes. When the IL-6 inflammatory stimulus is upregulated, HAMP gene transcription responds significantly (FIG. 3).

HAMP reporter constructs (as shown by RT-qPCR) respond to both IL-6 and the BMPs in a manner consistent with endogenous hepcidin.

Some diseases result from inadequate hepcidin production. The classic example of this would include the iron overload disease hemochromatosis. Hyper-absorption of dietary iron leads to accumulation of iron in the tissues, iron mediated injury, and organ dysfunction. Hereditary hemochromatosis (HH) usually results from an autosomal recessive mutation in the hemochromatosis protein (HFE) gene. The end result is insufficient production of hepcidin by the liver. This leads to improper iron absorption through enterocytes, and excessive iron transport into the serum.

Similar symptoms occur in β thalassemia hereditary diseases, β thalassemia patients have inherited a mutation where the beta chain synthesis of hemoglobin has been negatively affected. Affected individuals require lifelong blood transfusions, and are essentially receiving repeated doses of recycled iron without being able to properly stop absorbing it. Iron chelation and even phlebotomy treatments have been used as therapeutics.

Hepcidin excess or deficiency clearly plays a role in the pathophysiology of various iron disorders. Hepcidin agonists include agents that mimic the function of hepcidin, or promote its synthesis. Whereas hepcidin antagonists are factors that inhibit function or reduce hepcidin production. Therefore, the use of hepcidin agonists, or antagonists, could potentially be used as therapeutics in treating disease. For example, over expression of hepcidin in a model for HH prevented liver iron overload. Hepcidin knockout mice are shown to produce a milder anemia with quick recovery.

The very nature of using gene-silencing techniques successfully avoids the potentially dangerous side effects of drugs. However, these techniques are difficult to deliver throughout a tissue or system, and can have undesired over-lapping long-term effects. Erythropoiesis stimulating agents promote RBC production, but do not address issues with iron homeostasis.

Antibody therapies have had marginal success, most likely because of the small size and tightly folded structure of hepcidin. BMP pathway agonists have for the most part also pursued inhibition through the use of antibodies. Antibodies have high specificity and low toxicity. Despite these advantages there are drawbacks, including high production costs, eventual resistance, poor pharmacokinetics and tissue penetration, as well as limited efficacy requiring highly sustained doses.

Although hepcidin synthesis in hepatocytes is regulated by iron, erythropoietic activity and inflammation, the processing of hepcidin is specifically dependent on furin processing.

The success of the strategies used depends heavily on the safety and efficacy of the compounds involved, being non-toxic, biocompatible, and able to avoid recognition by the host's defense mechanisms.

Figure 4:
FIG. 4 shows the processing of preprohepcidin to hepcidin. Cleavage of prohepcidin occurs just after the multibasic poly-arginine motif, by the protease furin. Preprohepcidin has a molecular weight of 9.5 kDa, and prohepcidin and hepcidin have molecular weights of 6.9 kDa, and 2.8 kDa respectively.
Figure 4:
Figure 4:

The proprotein convertase (PC) known as furin (PC 1/3), has been specifically identified as being the sole PC responsible for generating active hepcidin. Hepcidin is initially synthesized as a larger precursor protein, undergoing two cleavages (the signal sequence then the pro-region). Furin is known to form mature, active hepcidin with the removal of this pro-region. Cleavage of prohepcidin occurs just after the multibasic poly-arginine motif, by the protease furin. Pre-prohepcidin has a molecular weight of 9.5 kDa, while prohepcidin and hepcidin have the molecular weights of 6.9 kDa and 2.8 kDa, respectively. Furin is also capable of activating hormones and other substrates by cleavage of the inactive protein precursors at multi-basic consensus motifs. In the case of hepcidin, furin readily hydrolyzes the prepro-hepcidin at its arginine rich consensus site, producing active hepcidin-25 to be secreted from hepatocytes (FIG. 4).

Serine Proteases

Serine proteases make up at least one third of all known protease enzymes. Serine proteases are known for their use of the catalytic triad in hydrolyzing peptide bonds. The —OH group serine residue is responsible for the nucleophilic attack, attacking the carbonyl carbon on the peptide bond of the substrate. The —OH group acts as the nucleophile, and the nitrogen on the histidine has the ability to accept the hydrogen from the serine —OH group. The aspartic acid residue's carboxyl group then hydrogen bonds with the histidine, making the nitrogen on the histidine more electronegative. A nearby pocket of positively charged residues also stabilizes the transition state of the deprotonated oxygen. This pocket is usually referred to as an oxyanion hole. Oxyanion holes also aid with substrate insertion, preventing steric hindrance by substrates that otherwise would not fit.

The most abundant sub-group of the serine proteases is the chymotrypsin-trypsin like protease family. These are involved in a multitude of physiological processes, including digestion, tissue repair, apoptosis, embryogenesis, and cell activation.

Proprotein convertases are a family of $Ca^{2+}$ dependent proteins known to activate other proteins, and perform a variety of activation functions within critical cellular pathways. These proteolytic enzymes cleave larger inactive protein precursors into smaller active forms. PCs are initially formed as zymogens. Zymogens are the inactive precursors that are chaperoned by their prodomains. The prodomains are essential in orchestrating folding and eventual departure from the endoplasmic reticulum (HR). Following exit from the ER, a pH and calcium dependent cleavage event in the trans-Golgi network activates the enzyme.

PC activity occurs through the kinetic contribution of the highly conserved catalytic domain (C domain) and protein-protein domain (P domain). Clustering of negatively charged amino acids within the C domain are common throughout all known PCs. This organization is responsible for the selectivity of pro-basic substrates. Seven PCs cleave after single or paired basic residues, and two (SKI-1, PC9) cleave at non-basic residues.

Novel approaches in studying PC kinetics and substrate specificity have been developed, including the use of fluorogenic assays. Although there is some cross talk between substrate specificity, each PC performs unique proteolytic tasks specific to that enzyme. Fluorogenic assays are particularly ideal for studying the kinetics of an enzyme. In this method, a fluorogenic peptide contains a fluorescent portion located at the C-terminus just after the known cleavage site. The most commonly used fluorescent groups are the 4-methyl-7-amino coumarinamide (MCA) and 7-amino-4-methyl coumarin (AMC) groups.

Although fluorogenic and other in vitro assays are useful when studying individual PCs and their substrates, understanding the physiological homeostasis of the PCs in vivo remains challenging. Some consequences of PC function have been explored through gene-knockout and tissue specific models. The absence or under expression of PCs during embryogenesis has critical effects during organ development. Knockout of furin is lethal at the embryonic stage, as formation of the cardiovascular system and gut are severely defective.

Knockouts of other PCs, when possible, have also shown extreme defects and deficiencies in growth and fertility (PC 2,4) or in development (PC 6), As PCs have the ability to activate a wide range of substrates, over expression or deficiency of PCs has been linked to many diseases. These include Alzheimer's, atherosclerosis, infectious diseases, cancer, and many others.

Suicide inhibition of a PC would likely be detrimental as a therapeutic due to the large amount of cross talk between PCs. Suicide inhibition occurs when covalent bonds, or irreversible bonds, are made with the catalytic triad residues within the PC. Inhibition of an upregulated PC, acting to clinically reduce activity back to basal rate through reversible binding, would likely be a better alternative.

Furin

Furin is a 794 aa serine endoprotease, and is as other PCs, dependent on calcium and pH for activity. Whereas other PCs enhance their catalytic properties in acidic environments, furin is optimally active at neutral pH.

Furin has a substilin-like domain with the catalytic triad (Ser368, His194, Asp153 typical of other serine proteases, and an oxyanion hole (Asn295). The oxyanion hole contains an asparagine that is interconnected to Ser368 through a water molecule, allowing for stabilization of serine's deprotonated oxygen during catalysis of a peptide bond.

Furin is expressed ubiquitously, in all tissues, and at high levels in the liver. At steady state, furin is found mostly in the trans Golgi network (TGN), as it cycles back and forth to the cell surface as well as within the endosome, cleaving various substrates under mildly acidic conditions. More recently, it has been reported that furin can be secreted from cell tissue cultures into media post transfection.

Figure 5:
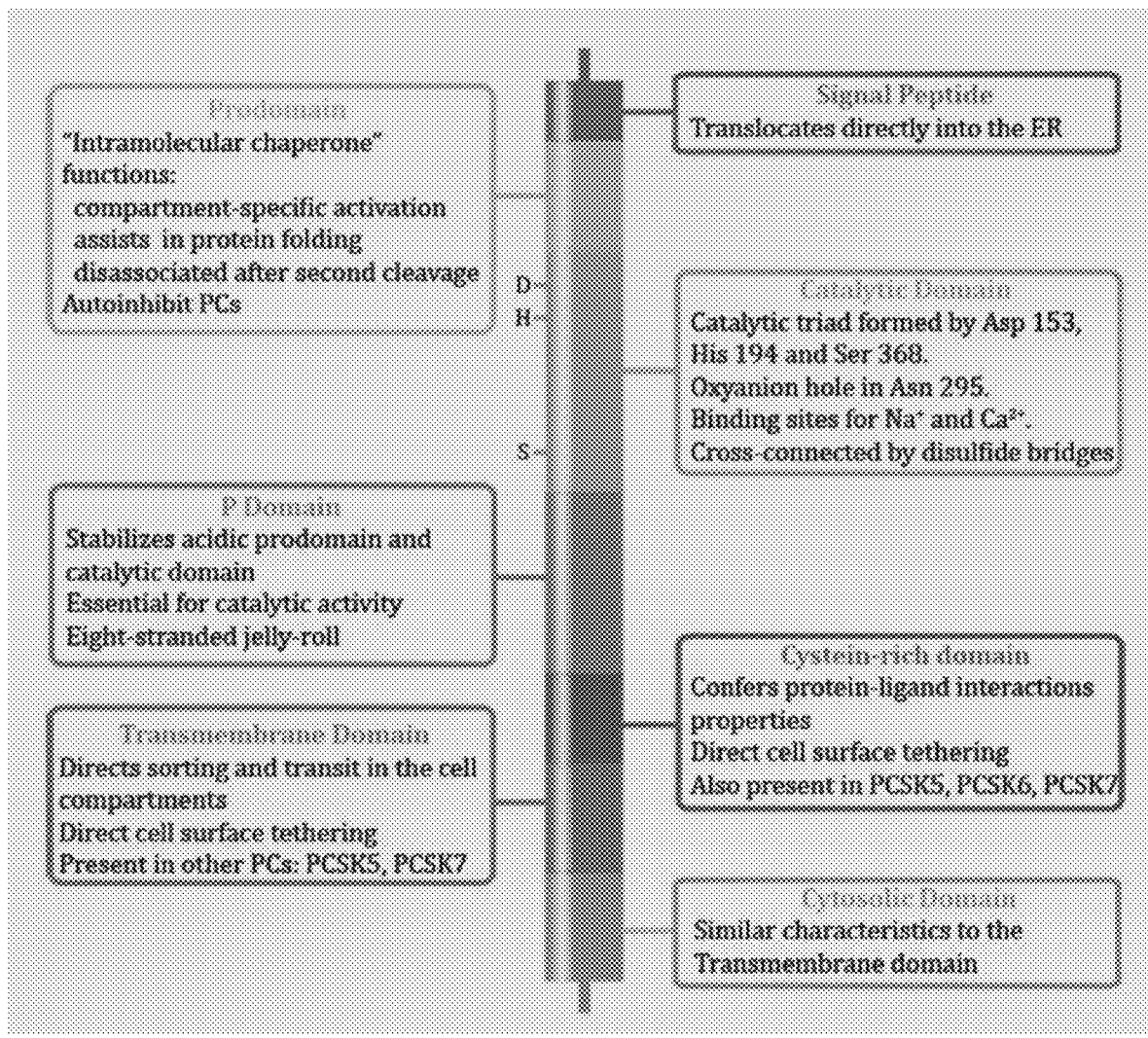
FIG. 5 is a schematic illustration of furin domains with their functions. Furin includes a catalytic (C) domain and the protein-protein (P) domain. Furin has three $Ca^{2+}$ binding sites and one $Na^+$ binding site, contributing to furin's catalytic cycle. Thus, furin is $Ca^{2+}$ dependent, requiring concentrations of at least 1 mM for full activity. The catalytic domain contains a conserved catalytic triad. The catalytic triad catalyzes peptide cleavage via a serine (368) residue, and stabilized by histidine (194) and aspartate (153). Serine's hydroxyl group acts as a nucleophile to attack the peptide's carbonyl carbon. Consequent tetrahedral intermediates are stabilized by a water molecule within the oxyanion hole, designated by the curved bar.

Proteolysis by furin is highly specific, and occurs on the C-terminal end of a multibasic recognition motif. The binding site strongly favors arginine at the PI site, and basic amino acid side chains at P2, P4 and/or P6 (FIG. 5). Furin cleaves secretory protein precursors at specific single or paired basic amino acids within the motif of $(Arg/Lys)X_n(Arg/Lys)\downarrow$, where X represents a neutral, polar amino acid, '$\downarrow$' designates the cut site, and $X_n$ represents a 0-, 2-, 4-, or 6-amino acid spacer.

2,5-dideoxystreptamine and dicoumarol derivatives, naphthofluorescein disodium salt (CCG-8294 or B3), and multi-arginine peptide mimetics have been used for the inhibition of furin. These compounds all act as competitive inhibitors of furin, interfering with proteolytic processing by furin's catalytic domain. Protein inhibitors such as α1-PDX also successfully inhibit furin in vitro and in vivo, and are commercially available to be studied in various disease models.

According, in some embodiments provided herein is a method for inhibiting the development or progression of anemia of chronic inflammation in a subject, comprising selecting a subject who suffers from or is at risk of developing anemia of chronic inflammation and reducing anemia of the subject by administering to the subject an effective amount of a pharmaceutical composition comprising one or more protease inhibitors, wherein the one or more protease inhibitors reduces the activity of furin.

In some embodiments, the method for inhibiting the development or progression of anemia of chronic inflammation includes administering one or more protease inhibitors. In some embodiments, the one or more protease inhibitors is selected from the group consisting of amprenavir, atazanavir, boceprevir, darunavir, fosamprenavir, indinavir, lopinavir, nelfinavir, ritonavir, saquinavir, simeprevir, tipranavir, or combinations thereof. One of skill in the art will recognize that the selection of the protease inhibitor relates to the ability of the protease inhibitor to bind to either or both of the catalytic and/or allosteric site of furin. In some embodiments, ritonavir is included with one or more additional protease inhibitor. Ritonavir is known to inhibit cytochrome P450 enzymes 3A4, the enzyme primarily responsible for metabolizing protease inhibitors within the liver. By adding ritonavir in combination with one or more protease inhibitor, the protease inhibitor serum levels are sustained for longer periods of time.

In some embodiments, the method for inhibiting anemia of chronic inflammation includes selecting a subject who suffers from or is at risk of developing anemia of chronic inflammation. In some embodiments, the subject suffers from or is at risk of developing an underlying chronic disease. In some embodiments the underlying chronic disease is an infectious disease, an inflammatory disease, heart disease, kidney disease, cancer, Alzheimer's disease, Parkinson's disease, Human Immunodeficiency Virus (HIV), Hepatitis-C virus (HCV), cytomegalovirus (CMV), Dengue virus, Ebola virus, Lassa virus, West Nile virus, rheumatoid arthritis, vasculitis, sarcoid, inflammatory bowel disease, multiple sclerosis, atherosclerosis, diabetes, congestive heart failure, or a combination thereof.

In some embodiments, the subject suffers from anemia as a result of a drug treatment to another disease. In some embodiments, the drug treatment that causes anemia is chemotherapy for the treatment of cancer. In some embodiments, the treatment increases the expression of hepcidin. In some embodiments, the treatment upregulates IL-6, BMP-6, or BMP-9.

In some embodiments, the subject who suffers from or is at risk of developing anemia of chronic inflammation has elevated serum hepcidin levels, low serum iron levels, low bone marrow iron levels, low red blood cell count, low hemoglobin levels, or combinations thereof. In some embodiments, the subject has elevated serum hepcidin levels greater than about 50 ng ml. In some embodiments, the subject has hemoglobin levels of less than about 13 g/dL.

In some embodiments, the pharmaceutical composition further includes one or more iron compound, erythropoietin, a chemotherapy drug, or a combination thereof. In some embodiments, the iron compound is selected from the group consisting of ferrous sulfate, ferrous fumarate, ferric pyrophosphate, iron gluconate, iron sucrose, iron dextran, intravenous iron treatments, and combinations thereof. In some embodiments, the pharmaceutical composition further includes one or more erythropoiesis stimulating agent. In some embodiments, the pharmaceutical composition further includes erythropoietin (EPO). In some embodiments, the EPO is recombinant EPO. In some embodiments, the recombinant EPO is glycosylated resulting in one or more of alpha, beta, delta, or omega forms of EPO.

In some embodiments, the pharmaceutical composition includes one or more protease inhibitors as the sole active ingredient. In some embodiments, the pharmaceutical composition optionally does not have an antibody.

In some embodiments is provided a method for inhibiting a disorder that has a propensity to cause anemia of chronic inflammation, including inhibiting the protease activity of furin in a subject suffering from a disorder that has a propensity to cause anemia of chronic inflammation and decreasing the levels of serum hepcidin in the subject. In some embodiments, the method of inhibiting the protease activity of furin includes administering to the subject a composition including one or more protease inhibitors.

In some embodiments is provided a method for modulating iron metabolism in a subject, including determining an amount of serum hepcidin in a subject suffering from or at risk of developing anemia of chronic inflammation and administering to the subject a pharmaceutical composition including one or more protease inhibitors when the amount of serum hepcidin is above normal levels. In some embodiments, the amount of serum hepcidin in a subject is determined to be greater than about 50 ng/mL. In some embodiments, modulating iron metabolism in a subject includes increasing serum iron levels, increasing bone marrow iron levels, increasing red blood cell counts, increasing hemoglobin levels, or combinations thereof.

Figure 23:
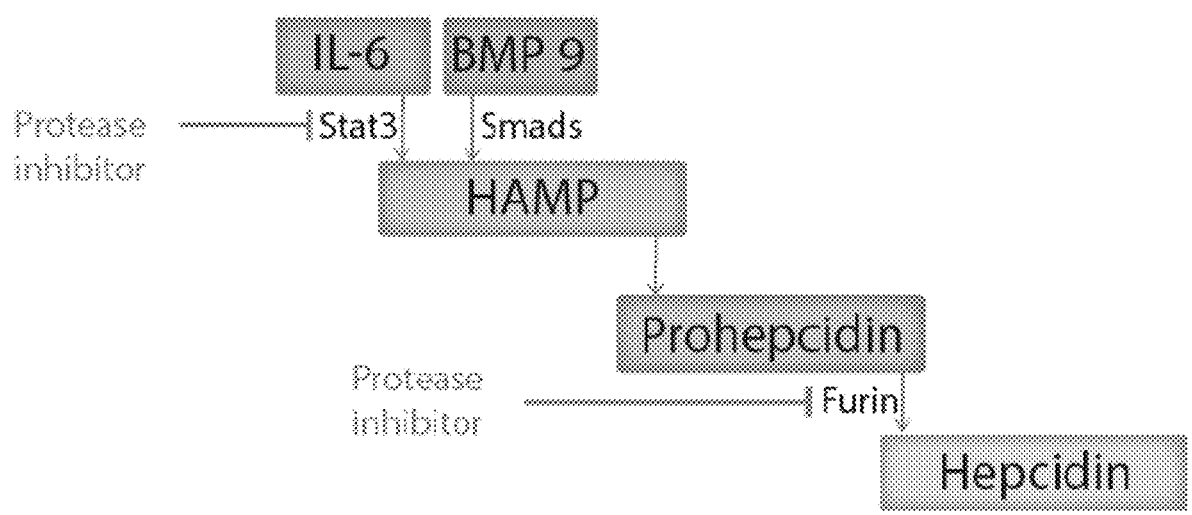
FIG. 23 is a schematic representation of predicted potential targets of selected PIs. Peptidomimetic small-molecule PIs included are nelfinavir, ritonavir, darunavir, indinavir, and CMK.

In some embodiments described herein, protease inhibitors effectively prevent hepcidin secretion from hepatocytes by inhibiting furin. In particular, nelfinavir acts as a catalytic site inhibitor and darunavir acts as an allosteric site inhibitor. Interestingly, nelfinavir has also been identified as a STAT3 phosphorylation inhibitor. As described herein, since HAMP is activated by a STAT3 phosphorylation pathway, nelfinavir acts as a dual inhibitor by functioning to inhibit both transcriptional activation of HAMP, as well as proteolytic cleavage of prohepcidin to hepcidin (FIG. 23).

EXAMPLES

Some aspects of the embodiments discussed above are disclosed in further detail in the following examples, which are not in any way intended to limit the scope of the present disclosure.

Experimental Materials and Methods

The following experimental materials and methods were used for Examples 1-5 described below.

In Silico Molecular Docking

Molecular interactions are the fundamental players in biological processes. To better understand binding and affinity between interacting molecules, the tertiary structure of proteins and three-dimensional structure of the molecule is required.

Acquiring complex tertiary or three-dimensional structures with experimental methods such as NMR or X-ray crystallography is laborious, challenging, and often expensive. Computational docking is a technique, which allows the researcher to gain understanding of protein-protein or protein-ligand interactions using molecular docking software. Docking is a method able to predict the preferred orientation of one molecule bound to another, forming a stable complex in three-dimensional space.

Modeling interactions between two molecules involves many intermolecular associations, including hydrophobic, van der Waals, stacking interactions between amino acids, hydrogen bonding, and electrostatic interactions. The process itself attempts to mimic a natural course of interaction involving the lowest energetic pathway.

If the receptor structure and ligand configuration is available, mathematical algorithms create an optimum number of configurations that include different binding modes. These algorithms regularly require supercomputers to handle the copious number of precise configurations and best-fit possibilities between two complex molecules.

Scoring functions are generally used for this purpose. A scoring function consists of a number of mathematical methods used to predict binding affinity. Binding affinity is defined here as the strength of the non-covalent interaction between ligand and protein. Scoring functions select the best pose, otherwise known as the best ligand conformation and orientation. These poses are then ranked based on affinity.

Some common searching algorithms include molecular dynamics, Monte Carlo methods, genetic algorithms, fragment-based, point complementary and distance geometry methods, and systematic searches.

Structure Preparation

When using these algorithms during virtual screening, lead optimization, or de novo drug design, several factors become critical. First, the protein's tertiary structure must be known. Factors of solvent, flexibility, and the environment to which the protein was initially characterized will influence the algorithm's output. Orientation of asparagine, histidine, and glutamine side chains, as well as the position of water molecules should be considered with caution, since their identification and location are challenging to X-ray crystallographers and sometimes different from in vivo conditions.

Second, the three-dimensional shape of the ligand when bound to the protein must be well understood. The proper stereochemistry of the small molecule in its most relevant setting should be considered. Factors of protonation state, tautomeric form, and concentration may be influential on prediction outcomes. Circumstantial differences in vivo often relay pharmacokinetic variation in ligands.

And third, the appropriate scoring function must be applied to estimate a relevant conformation and binding mode, A perfect scoring function would be able to predict the exact binding free energy between a ligand and its target. Unfortunately, differing scoring methods provide differing advantages and limitations. These variations lead to differences between docking scores and experimental results.

Scoring Functions

Currently, there are three main designations of scoring functions, including force field, statistical, and empirical scoring functions.

Force field scoring functions estimate the sum of strength of electrostatic interactions between all atoms of the two molecules involved. This includes not only the intermolecular forces, but also predicted intramolecular forces. Desolvation energies of the protein and ligand also contribute the summing of strength, as binding normally occurs in water or other solvents. The hydrophobic solvent accessible surface area, through use of the Generalized Born model, compliments the prediction data and aids in this calculation.

Statistical scoring potentials are energy functions derived from analysis of protein structures in the Protein Data Bank (PDB). These are approximations of free energy based on torsion angles, hydrogen bond geometry, and solvent exposure. The energies are determined using statistics from amino acid contacts, where a numerical value is affixed to each possible pair of amino acids binding to one another. Once values are assigned, calculated versions of binding affinity are ranked and ordered.

Empirical scoring functions focus on counting the types of interactions between two molecules. These interactions are scored as favorable versus unfavorable. A favorable scoring would include a hydrophobic-hydrophobic contact, whereas an unfavorable scoring would include a hydrophobic-hydrophilic contact. Rotatable bonds are considered unfavorable. Hydrogen bonds are considered as favorable, especially if shielded from solvent.

Scoring methods are constantly being revised to improve accuracy and limit variability. The recent introduction of metal ion interactions, improved pose predictions, sp2-sp2 torsions, and covalent bond docking, are just a few aspects that constantly contribute to the evaluation and debate of docking structures. However, published binding constants have shown a spread of computational factors to experimental factors of up to a factor of 5 ($\approx$4 kJ/mol).

Despite the common setbacks of protein and ligand flexibility, solvent interactions, and other limitations, computational molecular docking is proven as an effective basis for experimental testing and screening.

Application and Procedure of Protein-Ligand Molecular Docking

The amino acid sequence and tertiary structure of human furin is first retrieved from the National Center for Biotechnology Information (NCBI) and from the Protein Data Bank (PDB) under the classification entry codes (ex. 4OMD or 4OMC).

Small molecule ligands are collected from the ZINC database. The ZINC database is a free database of commercially available compounds for virtual screening. Containing over 35 million compound entries, molecules are available in ready-to-dock three-dimensional formats. Compounds can also be acquired from chemspider.com or the emolecules.com database. Although available in multiple file formats, ligand information available in mol2 files is most desired. Precaution should be taken to ensure that the mol2 file includes all applicable hydrogens and three-dimensional coordinates. Chirality and protonation state should also be reviewed.

To best review these variables and ensure proper ligand topology, mol2 files are uploaded to ChemDraw. ChemDraw is a drawing tool that allows for ligand editing among a multitude of other features. Once the ligand has been altered to the desired configuration, it can be saved and exported into a number of differing chemical file formats. The mol2 file format is presently a convenient format suitable for CHARMM energy calculation.

CHARMM software uses force field simulation analysis to predict molecular dynamics. As previously described, a force field scoring uses a set of mathematical functions to represent the potential energy of a system. A set of parameters is given to each type of atom, and based on these parameters a summation calculation is made to determine the strength of the force field. Once the ligand is properly prepared, it can be uploaded along with the protein PDB file onto the online docking server known as SwissDock.

SwissDock is based on the docking software EADock DSS. Many binding modes are produced in a designated box for what is known as local docking. Binding modes can also be produced in a target cavity, which is referred to as blind docking. CHARMM energies are then predicted and the binding modes with the most favorable energies are evaluated with a program called Fast Analytical Continuum Treatment Software (FACTS). FACTS provides a description of the solvation effect upon binding. After the most favorable energies are clustered and then ranked, the results can be downloaded. Predicted binding modes can be viewed via a Jmol applet, or uploaded into Chimera for further investigation.

SwissDock is a docking web server. The burdensome work of the docking engine is done on the server side. This allows for extensive docking calculations to be completed without the need for excess computational power on the client's side.

Viewing SwissDock Predictions in Chimera

Chimera is a free computational program used for interactive visualization of molecular structures, sequence alignments, docking results, and conformational illustrations. It allows for the analysis of sequence-structure-function relationships. Prediction software analyses and docking results can be explored visually in three-dimensions. Multiple software tools are linked to Chimera. Visualization plugins for NMR analysis, secondary and tertiary structure topography, and transmembrane protein images are openly accessible.

Chimera illustrates docking results, interpolate absolute fitness, and manifest free energy calculations. The site of binding is studied, and the lowest ΔG values recorded and evaluated. Compounds found in SDF, SMILES, or flexibase file formats can be converted into compliant, mol2 files using Chimera.

LigPlot+ or DIMPLOT Displays

Figure 6:
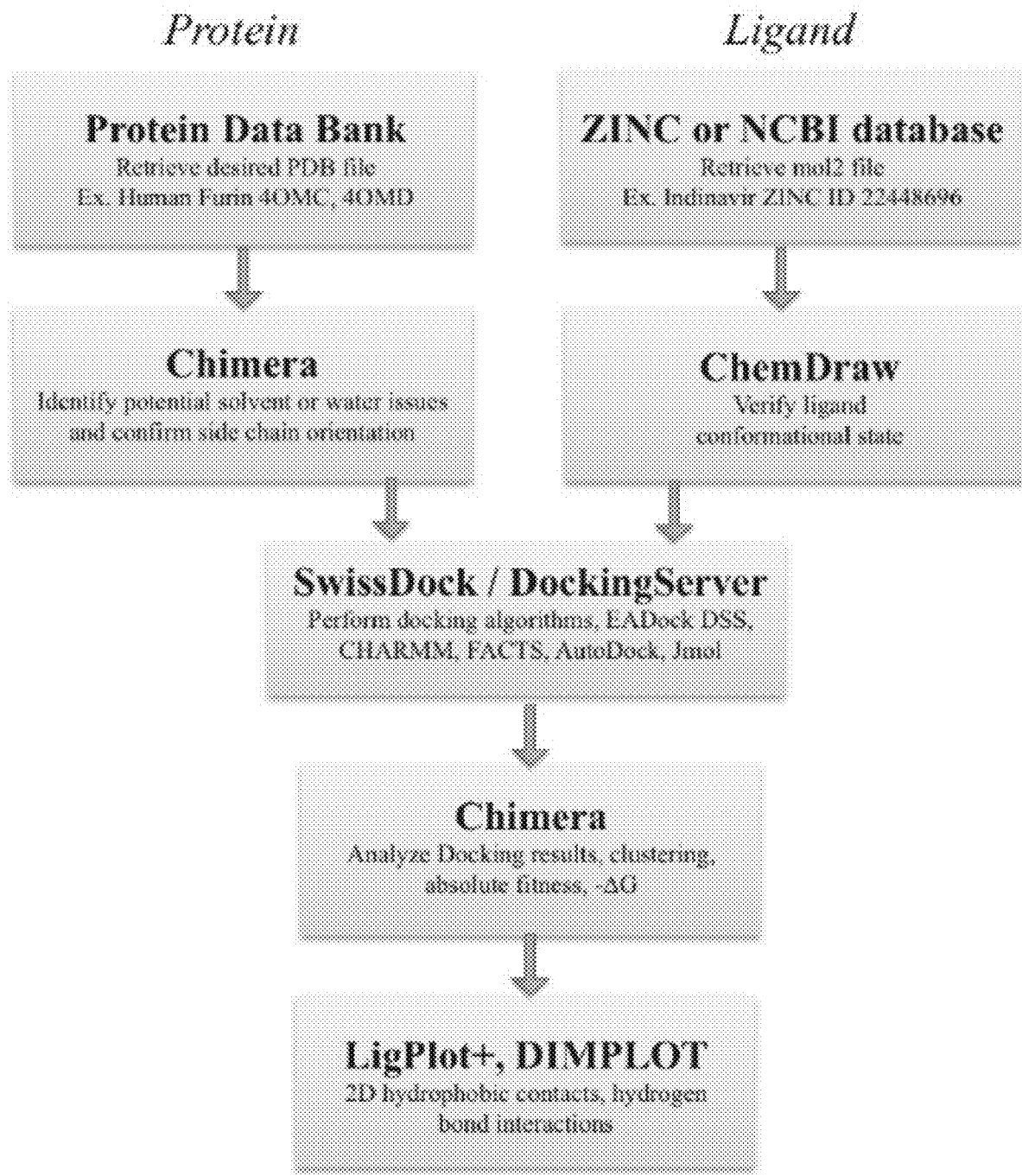
FIG. 6 depicts a molecular modeling flowchart. After retrieval of the protein and ligand files, the molecules are prepared with a molecular imaging program, such as Chimera, or with available options from Swissdock and DockingServer and subsequently submitted for docking. The resulting file can then be visualized in the molecular imaging program, such as Chimera. Interactions can then be mapped, for example with LigPlot+.

To further understand the ligand-protein interaction generated from the SwissDock predictions, a LigPlot can be performed. LigPlot+ software displays a two-dimensional view of the interaction between the ligand and the protein. LigPlots illustrate hydrophobic contacts and hydrogen bond interactions with any amino acids in the protein. Ligand-target complementarity between differing ligands can be viewed and compared. These visual aids help communicate differences in small molecules binding to the same protein target (FIG. 6), They can also aid in drag design strategy, Loading SwissDock output results files in .pdb format allow for LigPlot analysis.

HIV Protease Inhibitors as Potential Furin Inhibitors

HIV protease inhibitors are small-molecule ligands capable of binding with high affinity to catalytic residues within the homodimeric HIV protease. Their development is based on a structure-based drug design.

HIV proteases have conserved catalytic regions, with hydrophobic cavities and two aspartyl residues. Two aspartyl residues are responsible for hydrolyzing peptide bonds. Other amino acid residues along the catalytic domain mediate recognition and binding of substrate, by potentially forming hydrogen bonds or hydrophobic contacts with the substrate.

Based on the recognized cleavage sequences performed by HIV-1,2 protease, small-molecules were designed to mimic substrate, and fit within the hydrophobic cavity to prevent catalytic activity. As HIV protease is known to cleave sequences containing Tyr-Pro or Phe-Pro, "peptidomimetic" structures were synthesized to promote binding, and therefore inhibit cleavage of mature precursors.

Design of these small-molecule inhibitors include a hydroxyl group on the core motif, which is able to form a hydrogen bond with the carboxylic acid on the aspartic acid residues at the catalytic site. This bond is stabilized through a water molecule usually found within what is termed as an oxyanion hole. Design also involved adding different terminal residues to enhance solubility, as in the case of adding pyridyl groups in place of terminal phenyl residues.

Some residues on the protease binding site are capable of forming hydrogen bonds with hydrophilic groups on the inhibitor. Terminal tetrahydrofuran (THF) groups are added to the molecule for this purpose, as was done with amprenavir. In the case of darunavir, two have been added. The THF groups allow for more hydrogen bonds to be potentially made with the residues at the catalytic site of the protease, increasing binding affinity.

The basic design and structure of the HIV protease inhibitor small-molecules were designed for high affinity, based on principles of structural fit and hydroxyl motif. Consequently, it is not unreasonable to assume, that these small-molecules might also make potentially similar hydrogen bonds and hydrophobic contacts with other proteases. The hydroxyl group motif of the molecules could also form hydrogen bonds with the catalytic subunits.

Cells

Huh7 cells were purchased from the Japanese Research Cell Resource Bank (JRCB, Osaka, Japan. Lot 08062010), Cells were cultured in DMEM supplemented with 10% fetal bovine serum, non-essential amino acids, 100 U/ml, penicillin, and 100 μg/mL streptomycin (all from Gibco, Grand Island, NY) and kept at 37° C. in a humidified air chamber containing 5% $CO_2$.

HepG2 cells were purchased from the American Type Culture Collection. (ATCC, Manassas, VA Lot 60435372) These cells were cultured in EMEM medium supplemented with 10% heat-inactivated fetal bovine serum (I BS, Gibco, Grand Island, NY), 100 U/mL penicillin, and 100 μg/mL streptomycin, and kept at 37° C. in a humidified air chamber containing 5% $CO_2$.

Cells were seeded at a density of $1.5 \times 10^6$ per T25 flask in 5 mL culture medium and allowed to reach 50% confluency. At time 0, the cells received fresh media and were then simultaneously treated with either nelfinavir or darunavir alone, or nelfinavir and darunavir at varying concentrations (2.5/2.5 μM, 5/5 μM and 7.5/7.5 μM) and induced with IL-6 and BMP-9 (10 ng/mL each) for 18 hours. After 18 hours, 2 mL of media were collected, aliquoted and flash frozen for mass spectrometry (MS) analysis. Control groups not being induced with cytokines, are designated as 'Healthy'.

For the STAT3 and Smad4 experiments, the cells were seeded at a density of $1.5 \times 10^5$ per flask in 5 mL of culture medium and allowed to reach 70% confluency. At time 0, the cells received fresh media and were treated with nelfinavir, ritonavir, darunavir or indinavir, at concentrations ranging from 0 to 60 μM for three hours, and then induced with IL-6 or BMP-9 (Cat, #200-06 and 120-07, PeproTech, Rocky Hill, NJ) 50 ng/mL, for 30 minutes.

Protein Extraction from Cell Cultures

After treatments, cultured cells were washed with ice-cold PBS and lysed by adding ice-cold RIPA buffer containing 50 mM Tris-HCl (pH 8), 150 mM NaCl, 1% Triton X-100, 0.5% sodium deoxycholate, 0.1% SDS, 5 mM EDTA and IX protease/phosphatase cocktail inhibitor (Thermo Fisher Scientific, Waltham, MA), Cells were scraped off the flask and were further disrupted by passing the solution through a 21 gauge needle. The extracts were then transferred to a microfuge tube and centrifuged for 20 min at 12000 rpm. Protein concentration was determined with a Lowry assay and equal amounts of the resulting protein (30 μg) were separated by 8% SDS-PAGE and then transferred to a nitrocellulose membrane (Bio-Rad).

Western Blotting of Cell Samples

After transfer, the membranes were blocked in Odyssey™ Blocking Buffer (927-40100, LI-COR Biosciences, Lincoln, NE) at room temperature, for 1 hour. Primary antibodies were diluted in blocking solution containing 0.2% Tween and incubated overnight at 4° C. with polyclonal antibody to ferroportin (rabbit, 1:1000 dilution; PAS-2293, Thermo Scientific, Waltham, MA), phospho-STAT3 Tyr705 and STAT3 (1:1000 dilution, (Cat. #9145 and 9139 respectively, Cell Signaling Technology, Beverly, MA). Blots were normalized by probing the membranes with either a p-actin or glucose-6-phosphate dehydrogenase polyclonal antibody (Cat. #3700 and 8866 respectively, Cell Signaling Technology, Beverly, MA). After incubation and washing with PBS-T, the membranes where incubated in the dark, in blocking solution with 0.2% Tween with IRDye 800CW Goat anti-Rabbit IgG and IRDye® 680RD Donkey anti-Mouse IgG (1:10000, LI-COR Biosciences, Lincoln, NE) for 1 hour at room temperature. The proteins were detected and visualized by fluorescence using the Odyssey Classic (LI-COR Biosciences, Lincoln, NE). Densitometry analysis of specific bands was performed with the Image Studio software.

RNA Preparation from Tissue Culture, Reverse Transcription and RT2-qPCR

RNA was isolated by washing tissue culture in 1×PBS, before applying QIAzol lysis reagent (Cat #79306). RNA was then purified on RNeasy mini kit columns (Cat #74104) from Qiagen. All samples were treated with Qiagen DNase (Cat #79254). Two micrograms of RNA were used for reverse transcription and subsequent SYBR® Green ROX real time PCR for the genes of interest. Reverse transcription kits (Cat #330401) and SYBR Green real-time PCR master mixes (Cat #330523) were from Qiagen (Louisville, KY).

The following primers and probes were used: human hepcidin, HAMP (Cat #PPH06152A); human furin, TURIN (Cat #PPH09618A); human ferroportin, SLC40A1 (Cat #PPH5747A); and human glyceraldehyde 3-phosphate dehydrogenase, GAPDH (Cat #PPH00150F).

Real time quantitative PCR was performed on an Applied Biosciences StepOne plus instrument and analyzed with StepOne software v2.3. The relative amounts of transcripts from each gene were normalized to reference gene GAPDH and calculated as follows: $\Delta\Delta C_T$=the average $\Delta CT$ of sample B−the average $\Delta C_T$ of sample B, and their fold difference=$2^{-\Delta\Delta C_T}$.

Mass Spectrometry

Detection of Hepcidin-25 isoform was completed using an HPLC-MS/MS method with an Eksigent NanoLC HPLC with a Thermo Scientific C-18 reverse-phase column coupled via Thermo Scientific Nanospray ESI soft ionization source to a Thermo Scientific LTQ/Orbitrap XL mass spectrometer (MS). Samples were prepared for MS using an in-house developed enrichment and purification protocol. Data was collected over a 90 minute instrumental method starting with a 95:5 (v/v) mixture of water and acetonitrile up to 100% acetonitrile to cause gradient elution of the species of interest.

The mass spectrometer was tuned and calibrated to a pure human recombinant hepcidin-25 solution. All samples were treated with DTT or TCEP to reduce the disulfide bonds and were subsequently carbamidoalkylated with 2-iodoacetamide or 2-iodo-N-(phenylethyl)-acetamide to improve chromatographic characteristics and ESI response and efficiency. Peaks with isotopic envelopes corresponding to [M+5H+] and [M+6H+], 651.8 m/z and 543.3 m/z for 2-iodoacetamide, 818.5 m/z and 682.2 m/z for 2-iodo-N-(phenylethyl)-acetamide respectively, were detected in all samples and were not observed in the protocol blank. Fragmentation data (MS/MS) was collected on high abundance samples and subjected to the Matrix Science Mascot MS/MS Ions Search tool using a human database for sequencing and positive identification to the bioactive form of hepcidin-25. Quantification was completed using in-house developed ion chromatogram extractor software that allowed positive isolation of unfragmented peaks by m/z and chromatographic elution windows for total spectral ion count summation. Samples were intensity normalized to hepcidin-25 detected in healthy culture media for each dataset.

Sample preparation consisted of three phases: 1) ultra-filtration to remove large abundant proteins and media debris; 2) earboxamidomethylation of cysteine residues; and 3) 2-phase extraction of lipid substituents and subsequent concentration by speed-vac. Samples were acidified to 0.1% (v/v) formic acid immediately preceding data collection. Data was recorded at a resolution of 100,000 over the course of a two-hour method. Detected intensities were totaled using in-house developed ion-chromatogram extractor software.

Data Analysis

Statistical analysis was conducted using GraphPad Prism 5.0 software. Calculations for statistical differences between various groups were evaluated using a one-way ANOVA or a two-way ANOVA where appropriate followed by a Bonferroni post hoc test. Statistical significance is defined as $p<0.05$. Results are presented as means±Standard Error.

Animals

Female Lewis rats received at age 3-4 weeks and 75 g (Charles River Laboratories) were kept in a temperature-controlled (20° C.±1° C.) and well-ventilated room with a 12:12-h light-dark cycle. Animals had free access to standard (Diet 8604, Harlan Teklad) rodent laboratory chow and water. Chow iron content was 300 mg/kg. All experimental procedures were approved by applicable standards, including the BYU IACC.

Female Lewis rats at seven weeks of age received a single intraperitoneal inoculation of Group A Streptococcal Peptidoglycan-Polysaccharide (PG-LPS; Lee Laboratories) suspended in a 0.85% saline. Total dose received was 12.5 μg rhamnose/g body weight. Two weeks after PG-LPS injection, animals were tested for development of anemia, and randomized into groups with similar hemoglobin (Hb) and hematocrit (HCT) levels. Animals incurring greater than a 2 g/dL hemoglobin drop from baseline range were characterized as having ACL Treated animals received a human equivalent dose of prescription nelfinavir (Viracept) and ritonavir (Norvir) via oral gavage. To utilize the potential of nelfinavir, ritonavir is co-administered to adequately promote nelfinavir serum concentrations. Ritonavir is known to inhibit cytochrome P450 enzymes 3A4, the enzyme primarily responsible for metabolizing nelfinavir within the liver. By adding ritonavir alongside nelfinavir, nelfinavir serum concentrations are sustained for longer periods of time.

The adjusted rat dose was calculated by the body surface area (BSA) normalization method as previously described, where the human equivalent dose (mg/kg) is equal to animal dose (mg/kg) multiplied by (animal Km/human Km). Animal and human Km equal 37 and 6 respectively. Drug treatment was administered every 12 hours via oral gavage.

Equal volumes of dimethyl sulfoxide (DMSO) and flax seed oil were used as vehicle. Protease inhibitors nelfinavir and ritonavir have high solubility properties in DMSO as compared to water. The flax seed oil was used in combination to sustain serum concentrations for longer periods of time. Both drugs were weighed and crushed together from tablet into powder form before being dissolved in DMSO, immediately prior to administration. One dose is represented as 1 mL total volume.

Throughout the treatment period, ~0.5 mL of blood was collected once a week from a small tail clip. Complete blood counts (CBC) were performed on a BeckmanCoulter HmX Hematology Analyzer. Serum iron analysis was performed via inductively coupled plasma mass spectrometry (ICP-MS). Animals were weighed daily and scored for pain and distress.

After 6 weeks of treatment (8 weeks after induction of ACI), all rats wore euthanized with tissues being snap-frozen in liquid nitrogen and stored at −80° C. for subsequent gene expression studies, iron analysis, and protein analysis.

Protein Extraction from Animal Tissue

Approximately 100 mg of liver frozen tissue was transferred to ice cold RIPA buffer containing 50 mM Tris-HCl (pH 8), 150 mM NaCl, 1% Triton X-100, 0.5% sodium deoxycholate, 0.1% SDS, 5 mM EDTA and IX protease/phosphatase cocktail inhibitor (Thermo Fisher Scientific, Waltham, MA) and homogenized on ice with a glass pestle at 700 rpm. The homogenate was transferred to a pre-chilled, clean microfuge tube, subjected to three freeze-thaw cycles and centrifuged for 25 minutes at 12,000 rpm. The supernatant was collected and protein content was determined with a Lowry protein assay.

Western Blotting of Animal Samples

Protein samples were prepared for electrophoresis and equal amounts of resulting protein were separated in 8% SDS PAGE and then transferred to a nitrocellulose membrane (Bio-Rad). After transfer, the membranes were blocked in Odyssey™ Blocking Buffer (927-40100, LI-COR Biosciences, Lincoln, NE) at room temperature for 1 hour. Primary antibodies were diluted in blocking solution containing 0.2% Tween and incubated overnight at 4° C. with polyclonal antibody to ferroportin (rabbit, 1:1000 dilution; ab85370, Abcam, Cambridge, MA)). Blots were normalized by probing the membranes with P-actin (Cat. #3700). Cell Signaling Technology, Beverly, MA). After incubation and washing with PBS-T, the membranes where incubated in the dark, in blocking solution with 0.2% Tween with IRDye 800CW Goat anti-Rabbit IgG and IRDye® 680RD Donkey anti-Mouse IgG (1:10000, LI-COR Biosciences, Lincoln, NE) for 1 hour at room temperature. The proteins were detected and visualized by fluorescence using the Licor Odyssey Classic Infrared Imaging system (LI-COR Biosciences, Lincoln, NE). Densitometry analysis of specific bands was performed with the Image Studio software provided by LI-COR Biosciences.

RNA Preparation from Tissue, Reverse Transcription and RT-qPCR

RNA was isolated by homogenizing frozen ground liver in Trizol reagent (Cat #15596-018) from Invitrogen with an OMNI Tissue Master homogenizer, and then purified on RNeasy mini kit columns (Cat #74104) from Qiagen. All samples were treated with DNase (Cat #79254) from Qiagen. Two micrograms of RNA were used for reverse transcription and subsequent SYBR® Green ROX real time PCR for the genes of interest as previously described (Shanmugam, N. K. N. et al. Tumor Necrosis Factor a Inhibits Expression of the Iron Regulating Hormone Hepcidin in Murine Models of Innate Colitis. PLoS ONE 7, e38136 (2012)). Reverse transcription kits (Cat #330401) and SYBR Green real-time PCR master mixes (Cat #330523) were from Qiagen (Louisville, KY).

The following primers and probes were used: rat hepcidin, HAMP (Cat #PPR43953A); rat furin, TURIN (Cat #PPR43007A); rat ferroportin, (Cat #PPR46085A); and rat glyceraldehyde 3-phosphate dehydrogenase, GAPDH (Cat #PPR 06557B).

Real time quantitative PCR was performed on an Applied Biosciences Step One plus instrument and analyzed with StepOne software v2.3. The relative amounts of transcripts from each gene were normalized to reference gene glyceraldehyde 3-phosphate dehydrogenase (GAPDH) and calculated as follows: $\Delta\Delta C_T$=the average $\Delta C_T$ of sample B−the average $\Delta C_T$ of sample B, and their fold difference=$2-^{\Delta\Delta}C_T$ as previously described (Arikawa, E. et al. Cross-platform comparison of SYBR® Green real-time PCR with TaqMan PCR, microarrays and other gene expression measurement technologies evaluated in the MicroArray Quality Control (MAQC) study, BMC Genomics 9, 328 (2008)). No statistical variance of reference gene expression was observed between tissue groups.

Enzyme-Linked Immunosorbent Assays (ELISA)

The following commercially available ELISA kits were used to quantify protein concentrations in Lewis Rat serum:

Hepcidin-25 and Prohepcidin ELISA kits (Cat #EIA5258 and Cat #EIA4644 DRG International, Mountainside, NJ).

Interleukin-6 ELISA kits (Cat #437107, BioLegend, San Diego CA).

Bone morphogenic protein-9 (BMP-9), also known as Growth Differentiation Factor-2 (GDF-2), protein ELISA kits (Cat #SEB728Ra, Cloud-Clone Corp., Houston TX).

Erythropoietin ELISA kits (Cat #MBS160249, MyBio-Source, San Diego, CA).

Inductively Coupled Plasma Mass Spectrometry (ICP-MS) Fe Analysis

Serum and tissue samples previously prepared and preserved in liquid nitrogen were weighed and dissolved in 1 mL 70% OmniTrace® analytical grade nitric acid. Samples were then sonicated for 30 minutes, diluted to 3% nitric acid and heated to 95° C. for 3 hours. Finally, they were centrifuged for 30 minutes at 15,000 g with supernatant collected for analysis. Trace iron quantification was measured via a Perkin Elmer Elan 6000 Inductively coupled plasma mass spectrometer as previously described (Sariego Muiz, C., Marchante Gayn, J. M., Garcia Alonso, J. I. & Sanz Medel, A. Speciation of essential elements in human serum using anion exchange chromatography coupled to post column isotope dilution analysis with double focusing ICP-MS. J. Anal, At. Spectrom. 16, 587-592 (2001); Ciavardelli, D. et al. Phenotypic profile linked to inhibition of the major Zn influx system in Salmonella enterica: proteomics and ionomics investigations. Mol Biosyst. 7, 608 (2011)), Multi-elemental standard solutions were used for calibration.

Example 1

Determination of an Allosteric Site on Furin

This example demonstrates the determination of an allosteric site on furin, which provides synergistic inhibition of furin activity through binding of protease inhibitors to one or both of the catalytic and allosteric site.

Protein structure files of the human paired basic amino acid cleaving enzyme known as furin were retrieved from the Protein Data Bank (PDB) with ID 4OMC, 4OMD containing resolution of about 2.71 Å. Structures of known inhibitors were removed and the resulting PDB file saved. Necessary hydrogen atoms and solvation parameters were added to the structure with the help of AutoDock tools.

The target protein is visualized in .pdb format using UCSF Chimera software (Pettersen, E. F. et al. UCSF Chimera—A visualization system for exploratory research and analysis. *J. Comput. Chem.* 25, 1605-1612 (2004)), where remaining residual solvent structures could be removed, which often interfere with docking software analysis by Swissdock. The resulting .pdb file is then uploaded onto online Swissdock modeling prediction software used to characterize binding sites of potential ligands to the modeled furin protein structure, Swissdock is a protein ligand docking web service powered by EADock DSS by the Molecular Modeling group of the Swiss Institute of Bioinformatics (Grosdidier, A., Zoete, V. & Michielin, 0. EADock: Docking of small molecules into protein active sites with a multi objective evolutionary optimization. *Proteins Struct. Fund. Bioinforma.* 67, 1010-1025 (2007)). Swissdock automatically searches for the chemical ligand structure from Zinc database using the pharmaceutically and commercially available isomers of the following ligands. Binding modes were scored using their Full fitness score and then clustered. Clusters were then ranked according to the average Full fitness of their elements. Moreover, results can be downloaded and viewed in Chimera. The following protease inhibitors were screened.

Amprenavir. (3S)-oxolan-3-yl N-[(2S,3R)-3-hydroxy-4-[N-(2-methylpropyl)(4-aminobenzene)sulfonamide]-1-phenylbutan-2-yl] carbamate, also known commercially as Agenerase, Zinc ID 3809192, Atazanavir. Methyl N-[(1S)-1-{[(2S,3S)-3-hydroxy-4-[(2S)-2-[(methoxycarbonyl)amino]-3,3-dimethyl-N'-[[4-(pyridm-2-yl]phenyl]methyl}bulanehydrazido]-1-phenylbutan-2-yl[carbamoyl]-2,2-dimethylpropyl]carbamate, also known as Reyataz, Zinc ID 3941496.

Darunavir. [(1R, 5S, 6R)-2,8-dioxabicyclo[3.3.0]oct-6-yl] N-[(2S, 3R)-4-[(4-aminophenyl)sulfonyl-(2-methylpropyl) amino]-3-hydroxy-1-phenyl-butan-2-yl] carbamate, also known as Prezista, Zinc ID 3955219.

Indinavir. (2S)-1-1(2S,4R)-4-benzyl-2-hydroxy-4-[[(1S, 2R)-2-hydroxy-2,3-dihydro-1H-inden-1-yl]carbamoyl] butyl]-N-tert-butyl-4-(pyridin-3-ylmethyl)piperazine-2-carboxamide, also known as Crixivan, Zinc ID 22448696.

Lopinavir. (2S)—N-[(2S,4S,5S)~5~[2-(2,6~dimethylphenoxy)aceiamido]-4-hydroxy-1,6-diphenylhexan-2-yl]-3-methyl 2-(2-oxo-1, 3-diazinan-1-yl)butanamide, also known as Kaletra, Zinc ID 3951740, Nelfinavir. (3S,4aS,8aS)—N-tert-butyl-2-[(2R,3R)-2-hydroxy-3-[(3-hydroxy-2-methyl(phenyl) formamido]-4-(phenylsulfanyl)butyl]-decahydroisoqmnoline-3-carboxamide, also known as Viracept, Zinc ID 26994433, Ritonavir. [(1,3-thiazol-5-ylmethyl N-[(2S, 3S, 5S)-3-hydroxy-5-[(2S)-3-methyl-2-{[methyl({[2-(propan-2-yl)-1, 3-thiazol-yl]methyl})carbamoyl]amino}butcmamido]-1, 6-diphenylhexan-2-yl]carbamate, also known as Norvir, Zinc ID 3944422.

Saquinavir. (2S)—N-[(2S, 3R)-4-[(35)-3-(tert-butylcarbamoyl)-decahydroisoquinolin-2-yl]-3-hydroxy-1-phenybutan-2-yl]-2-(quinolin-2-ylformamido)butanediamide, also known as Fortovase, Zinc ID 3914596, Tipranavir. N-{3-[(1R)-1-[(2R)-6-hydroxy-4-oxo-2-(2-phenylethyl)-2-propyl-3,4-dihydro-2H-pyran-5-yl]propyl] phenyl}-5-(trifluoromethyl)pyridine-2-sulfonamide, also known as Aptivus, Zinc ID 14879987.

Chemical structures are docked with furin as the receptor in Chimera using default parameters. Small molecule ligand structures are converted into .mol2 flies via Parachem (Vanommeslaeghe, K., Raman, E. P. & MacKerell, A. D. Automation of the CHARMM General Force Field (CGenFF) II: Assignment of Bonded Parameters and Partial Atomic Charges. *J. Chem. Inf. Model.* 52, 3155-3168 (2012)), as to further properly format computational framework for Swissdock. Values are obtained in terms of energy $-\Delta G$ in units kcal/mol.

Predicted binding modes and docking results are then loaded into the ViewDock (Lau, C. D., Levesque, M. J., Chien, S, Date, S. & Haga, J. H. ViewDock TDW: high-throughput visualization of virtual screening results. Bioinformatics 26, 1915-1917 (2010)) plugin and JSmol (Hanson, R. M. Jmol—a paradigm shift in crystallographic visualization. *J. Appl. Crystallogr.* 43, 1250-1260 (2010); Hanson, R. M., Prilusky, J., Renjian, Z., Nakane, T. & Sussman, J, L. JSmol and the Next-Generation Web-Based Representation of 3D Molecular Structure as Applied to Proteopedia. *Isr. J Chem.* 53, 207-216 (2013)) before being characterized further within Chimera and LigPlotplus (Laskowski, R. A. & Swindells, M. B. LigPlot+: Multiple Ligand-Protein Interaction Diagrams for Drug Discovery. *J. Chem. Inf. Model.* 51, 2778-2786 (2011)) software.

To validate and complement the results obtained from SwissDock docking jobs were further submitted to another server. Docking calculations were carried out using DockingServer (Bikadi, Z. & Hazai, E. Application of the PM6 semi-empirical method to modeling proteins enhances docking accuracy of AutoDock. *J. Cheminformatics* 1, 15 (2009)). Ligand files were obtained from PubChem, IDs 641413 (Nelfinavir) and 213039 (Darunavir). Gasteiger partial charges were added to the ligand atoms. Non-polar hydrogen atoms were merged, and rotatable bonds defined. Docking calculations were carried out on chain A of 4OMC (PDB). Essential hydrogen atoms, Kollman united atom type charges, and solvation parameters were added with the aid of AutoDock tools. Affinity (grid) maps of 0.375 A spacing were generated using the Autogrid program (Morris, G. M. et al. Automated docking using a Lamarckian genetic algorithm and an empirical binding free energy function. *J. Comput. Chem.* 19, 1639-1662 (1998)). AutoDock parameter set- and distance-dependent dielectric functions were used in the calculation of the van der Waals and the electrostatic terms, respectively.

Docking simulations were performed using the Lamarckian genetic algorithm (LGA) and the Solis & Wets local search method (Solis, F. J. & Wets, R, J.-B. Minimization by Random Search Techniques. *Math. Oper. Res.* 6, 19-30 (1981)). Initial position, orientation, and torsions of the ligand molecules were set randomly. All rotatable torsions were released during docking. Each docking experiment was derived from 255 different runs that were set to terminate after a maximum of 2,500,000 energy evaluations. The population size was set to 150. During the search, a translational step of 0.2 Å, and quaternion and torsion steps of 5 were applied. Two docking boxes were set up, one including the known catalytic triad residues and one on the proposed allosteric site.

Recombinant human furin was purchased from New England BioLabs (Ipswich, MA). Fluorogenic furin convertase substrate BOC-Arg-Val-Arg-Arg-AMC (AMC=7-Amino-4-methylcoumarin) from Enzo Life Sciences (Farmingdale, NY) and HIV aspartyl protease inhibitors (Sigma) were dissolved in DMSO. Protease inhibitory' drugs were prepared at a. concentration of 10 mg/mL and stored at room temperature. Furin Inhibitor II chloromethylketone was purchased from EMD Millipore (Darmstadt, Germany).

The assay was performed at pH 7.5 in buffer 50 mM HEPES, 1 mM $CaCl_2$, 1 mM β-mercaptoethanol, 0.2 mg/mL BSA. In a total volume of 100 μL, the final concentration per well of substrate enzyme was 10 μM and 1 U/well respectively. All assays were performed at 37° C. in a 96-well fluorometer (BioTek Synergy H4 Hybrid reader) with an excitation wavelength of 345 nm and an emission wavelength of 420 nm.

Inhibitory small molecules were incubated with enzyme for 1 hour at 37° C. prior to addition of substrate to initiate the reaction. All assays were performed in triplicate. Inhibition constants were calculated based on methods previously described (Lineweaver, H. & Burk, D. The Determination of Enzyme Dissociation Constants. J. Am. Chem. Soc. 56, 658-666 (1934)). The rate of hydrolysis was followed for 60 minutes.

Huh7 cells were purchased from the Japanese Research Cell Resource Bank (JRCB, Osaka, Japan. Lot: 08062010). Cells were cultured in DMEM supplemented with 10% Fetal Bovine Serum, non-essential amino acids, 100 U/mL penicillin, and 100 μg/mL streptomycin (all from Gibco, Grand Island, NY) and kept at 37° C. in a humidified air chamber containing 5% $CO_2$.

Cells were seeded at a density of $1.5 \times 10^6$ per T25 flask (25 $cm^2$, PE plug seal cap, Cat #83.1810, Sarstedt, Newton, NC) in 5 mL culture medium and allowed to reach 50% confluency. At time 0, the cells received fresh media and were then simultaneously treated with nelfinavir and darunavir at varying concentrations and induced with IL-6 and BMP-9 (10 ng/mL each) for 18 hours. After 18 hours, media was collected, aliquoted and flash frozen for Mass Spectrometry (MS) analysis.

Sum totaled spectral ion intensities of Hepcidin-25 were detected using HPLC-MS/MS. An Eksigent NanoLC HPLC system and Thermo Scientific LTQ Orbitrap XL. mass spectrometer were used to analyze Huh7 immortalized hepatocyte cell media.

Sample preparation consisted of three phases: T) ultra-filtration to remove large abundant proteins and media debris; 2) carboxamidomethylation of cysteine residues; 3) 2-phase extraction of lipid substituents and subsequent concentration by speed-vac. Samples were acidified to 0.1% (v/v) formic acid immediately preceding data collection. Data was recorded at a resolution of 100,000 over the course of a two-hour method. Detected intensities were totaled using ion-chromatogram extractor software.

Figure 13:
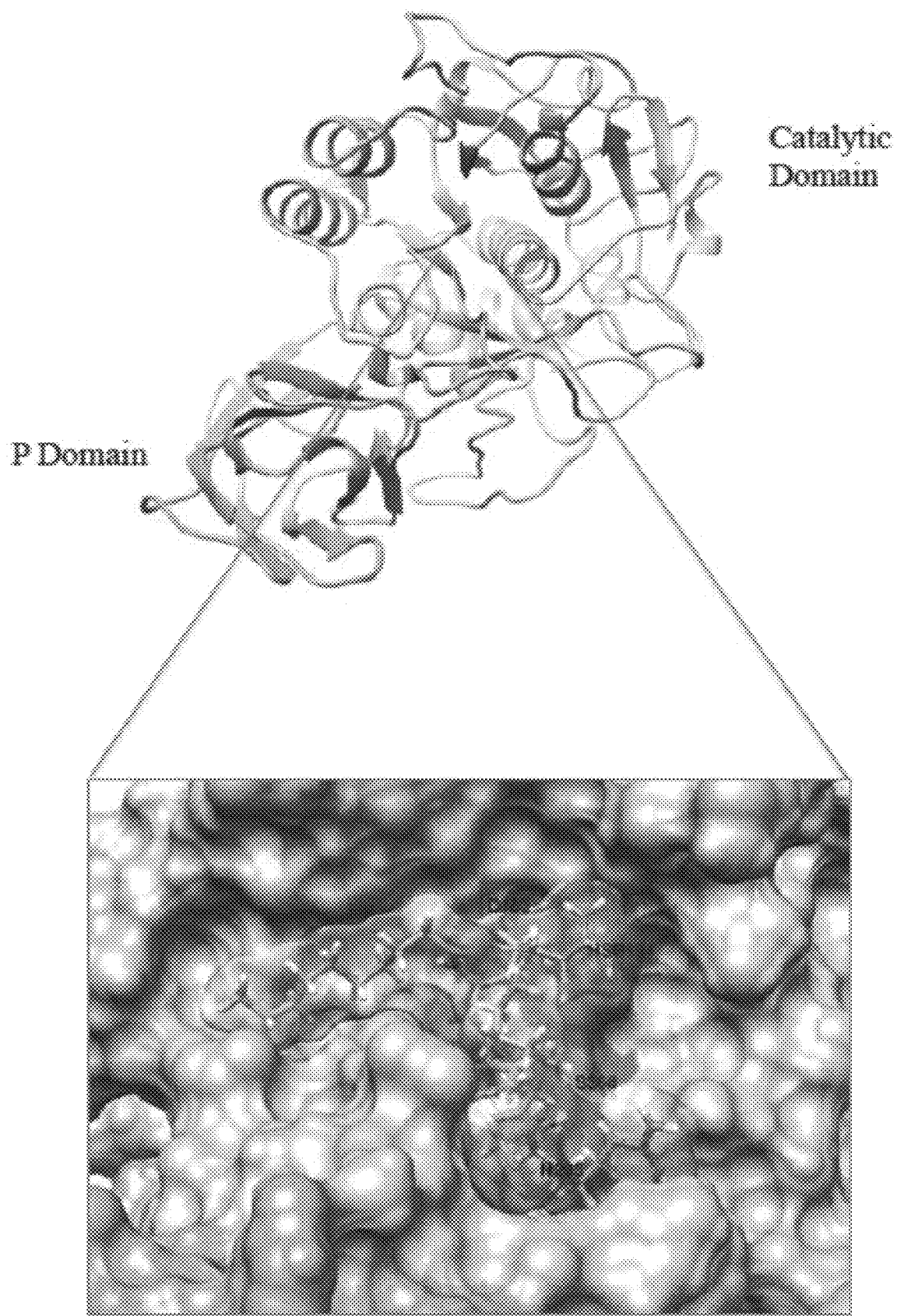
FIG. 13 depicts molecular representation of the known furin inhibitor CMK bound to the catalytic site of human furin (full fitness −1965.4, simple fitness −91.36, ΔG −11.24 kcal/mol).
Figure 22:
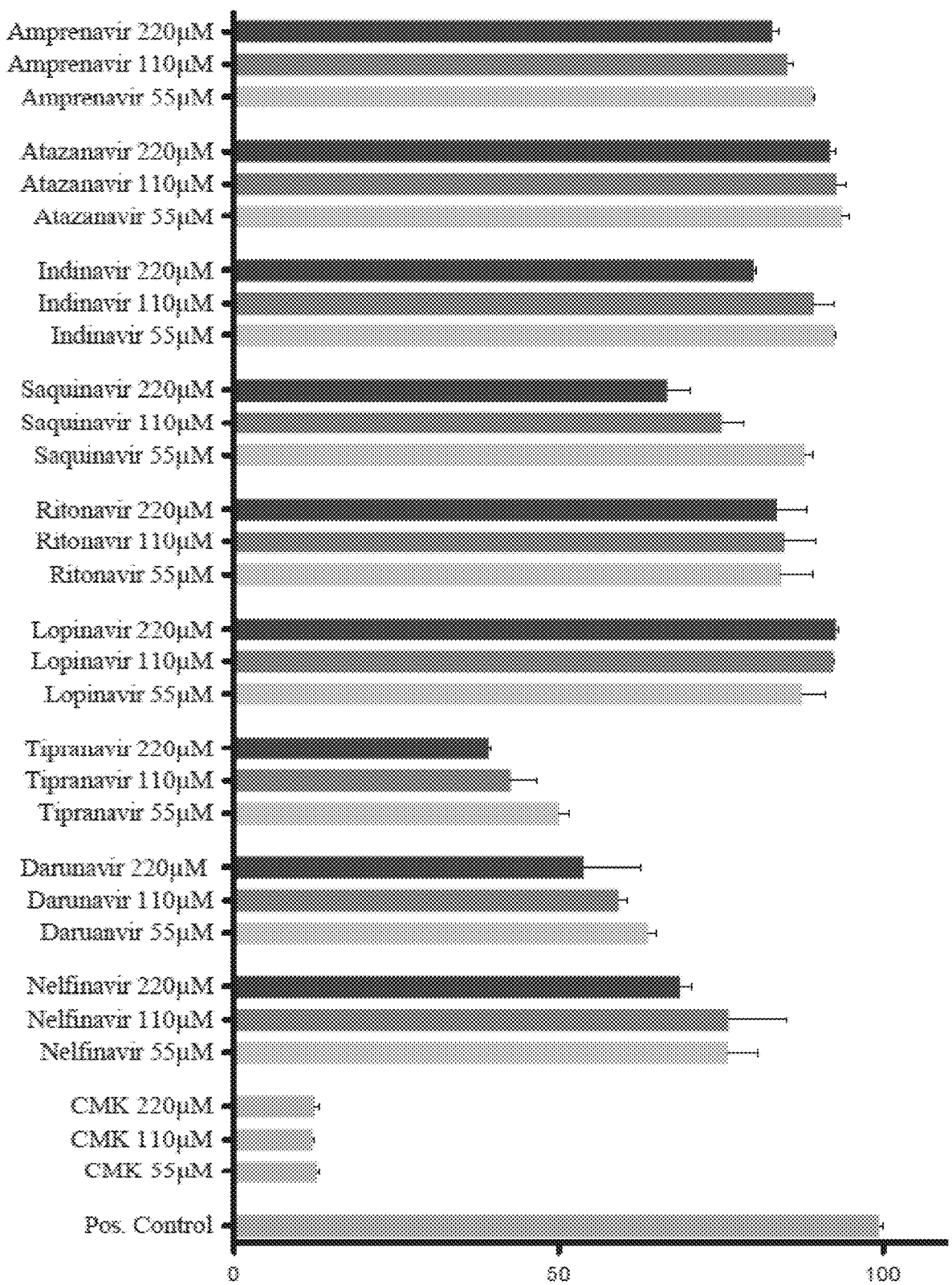
FIG. 22 shows the results of the in vitro furin activity drug screen assay. The positive control for furin activity is all assay components without any inhibitors added. CMK is used as a known furin inhibitor and represents full inhibition of furin. The remaining assays include furin, substrate, and the indicated concentration of the PI.

The SwissDock and LigPlot Molecular docking programs were used with the crystal structure of human furin to evaluate the binding of potential small molecule inhibitors to furin. Initial docking experiments were assessed using the known furin inhibitor CMK. Both the P-domain and the catalytic domain are required for catalytic activity. The region connecting the two domains acts as a hinge during catalysis and this molecular motion is important in catalysis. CMK binds at the active site of furin with a full fitness value of −1968.62 and free energy of binding (ΔG) of −11.07 kcal/mol (FIG. 13, FIG. 22, and Table 2).

TABLE 2

Swissdock Docking Results. Full Fitness And Free Energy Results Obtained From The Docking Of HIV Protease Inhibitors With Furin By Swissdock.

| ZINC ID | Protease Inhibitor | Catalytic Site | | Allosteric Site | |
|---|---|---|---|---|---|
| | | Full Fitness | −ΔG kcal/mol | Full Fitness | −ΔG kcal/mol |
| CAS 150113998 | Dec-RVKR-CMK | 1968.62 | −11.07 | −1974.15 | −9.25 |
| 3809192 | Amprenavir | N/A | | −1795.2 | −7.81 |
| 3941496 | Atazanavir | N/A | | −1709.16 | −8.82 |
| 3955219 | Darunavir | N/A | | −1794.72 | −8.18 |
| 22448696 | Indinavir | −1664.28 | −8.03 | −1674.87 | −8.22 |
| 3951740 | Lopinavir | N/A | | −1765.17 | −7.6 |
| 26994433 | Nelfinavir | −1716.31 | −8.24 | −1726.38 | −8.22 |
| 3944422 | Ritonavir | N/A | | −1834.58 | −8.57 |
| 3914596 | Saquinavir | −1676.77 | −8.92 | −1688.23 | −7.84 |
| 14879987 | Tipranavir | N/A | | −1747.93 | −8.58 |

*N/A represents data as not provided, as there was insufficient affinity of the drug for furin at this site.

Molecular docking programs were used to evaluate the binding of PIs to the catalytic site of human furin. Several of the PIs showed significant affinity for binding to the catalytic site of furin. The predicted free energy of binding (−ΔG of binding) and Full fitness scores are listed in Table 2. The evaluation of potential inhibitors was judged by the predicted free energy of binding (−ΔG), the full fitness score, and the goodness of fit.

Figure 7A:
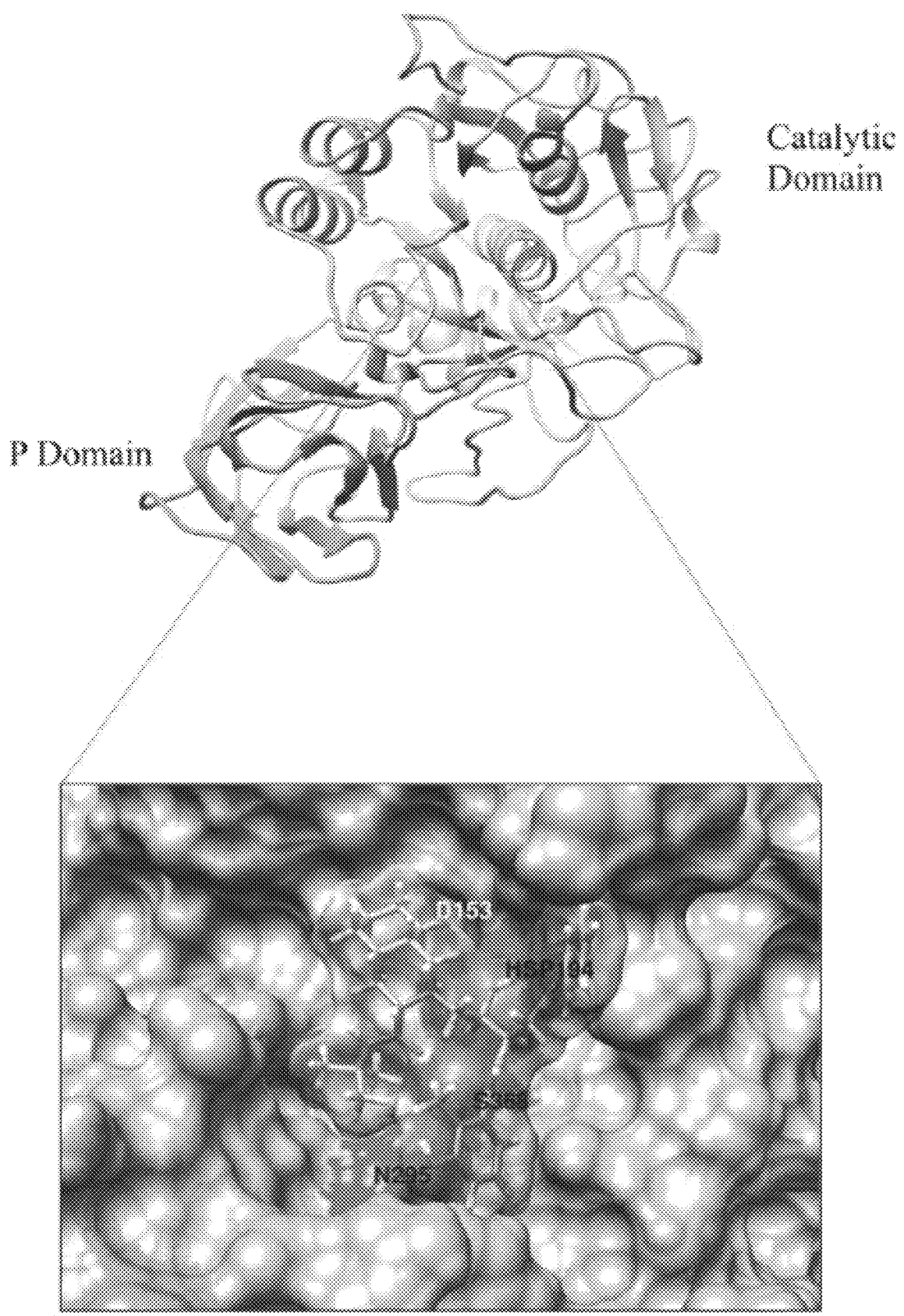
FIG. 7A depicts a surface visualization of nelfinavir binding to furin at the catalytic site and cysteine rich area of the P domain. Nelfinavir (full fitness −1716.31, ΔG −8.24 kcal/mol) is shown binding on the active site.
Figure 8A:
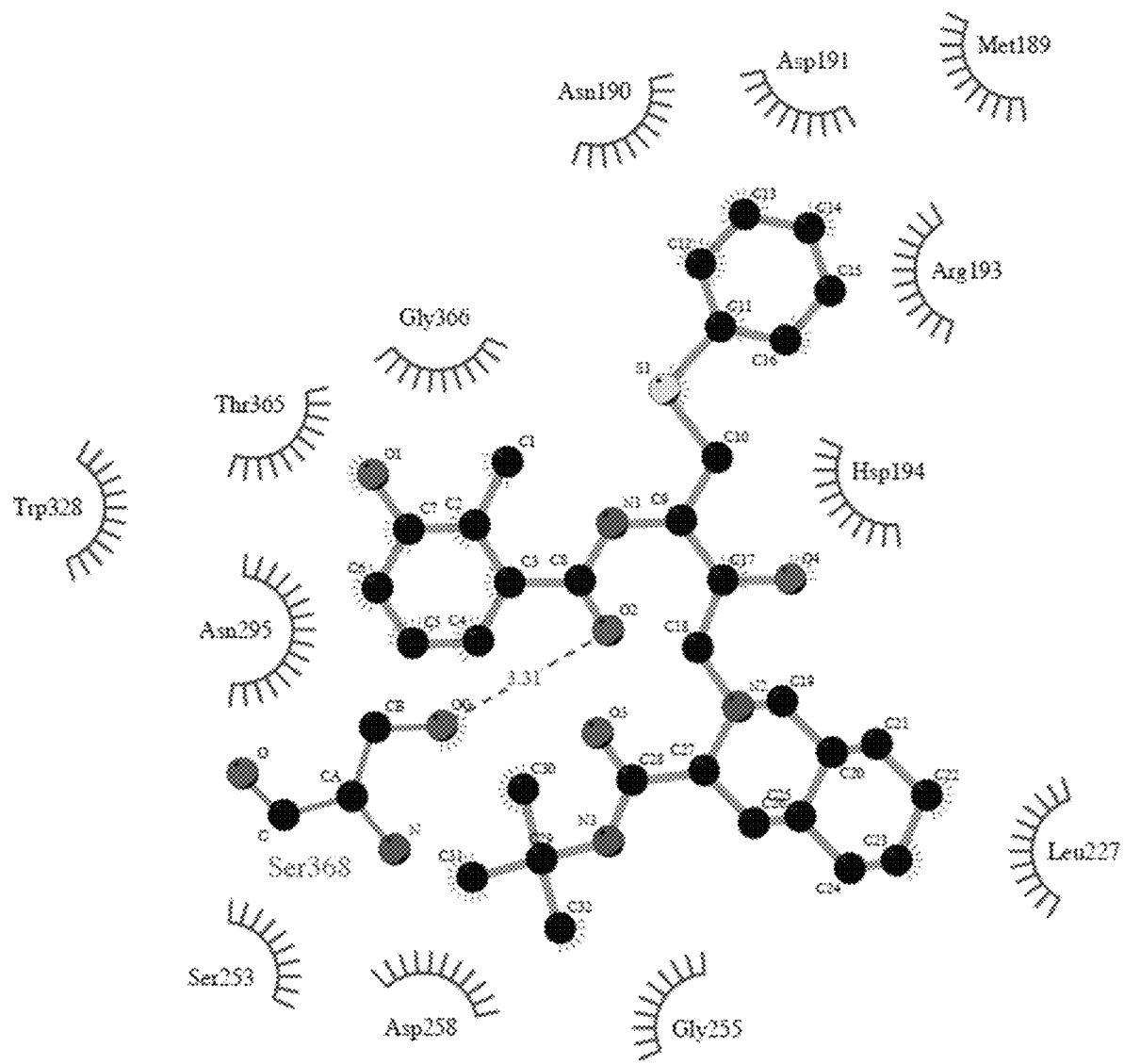
FIG. 8A illustrates a two-dimensional LigPlot representation of ligands with furin. Hydrogen bonds are depicted with dashed lines, and hydrophobic interactions are depicted as arches.

Nelfinavir docking showed high affinity for furin based on free energy of binding and Full fitness scores. Molecular docking studies show that nelfinavir has an affinity of binding to furin (ΔG=−9.18 kcal/mol) that is close to the affinity of CMK (ΔG=−11.07). FIGS. 7A and 8A show images of nelfinavir bound at the active site of furin, and identify the modeled interactions that contribute to the predicted binding.

Figure 17A:
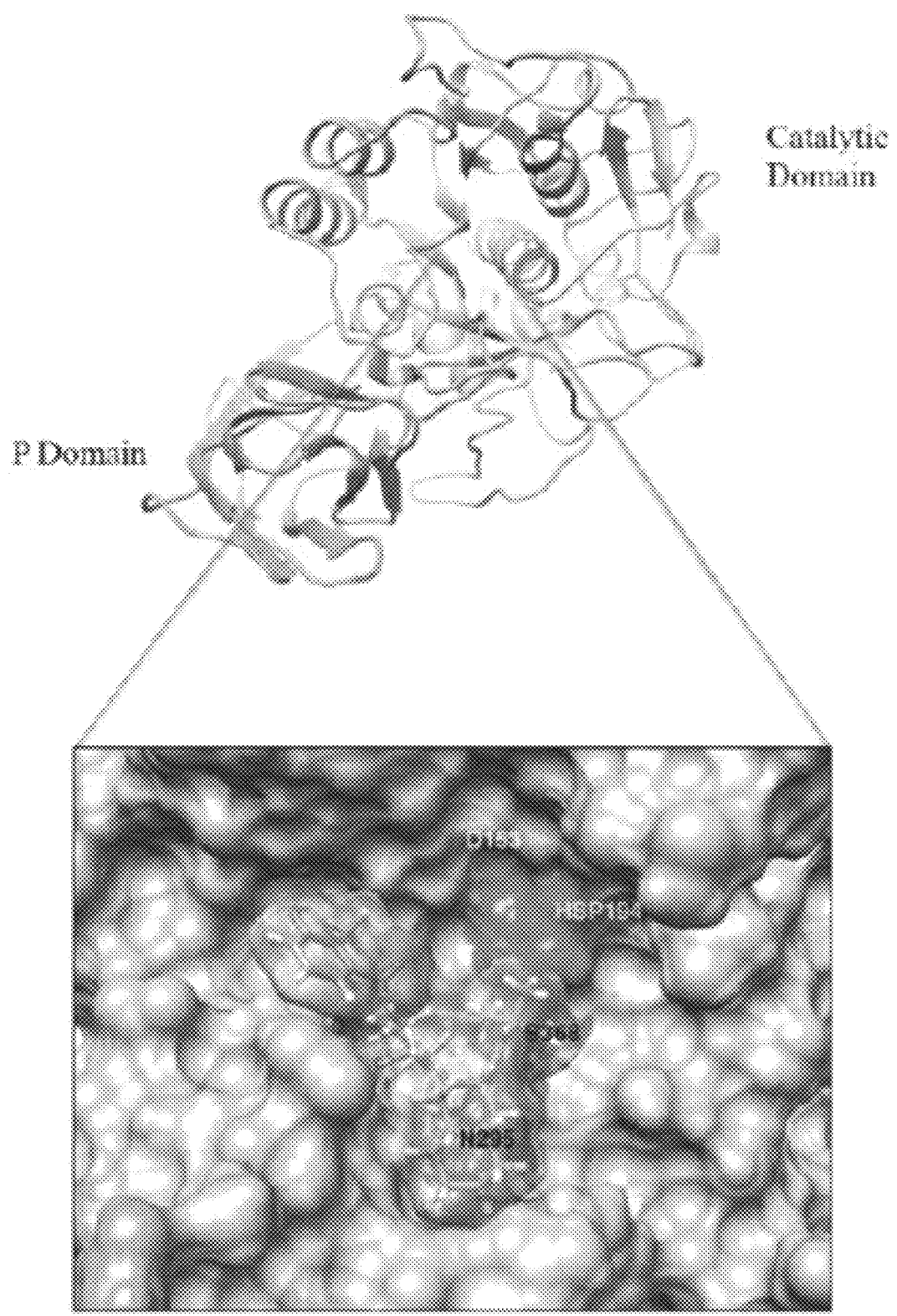
FIG. 17A depicts the surface visualization of nelfinavir in a second conformation at the catalytic site of furin (full fitness −1719.31, ΔG −9.18 kcal/mol).
Figure 17B:
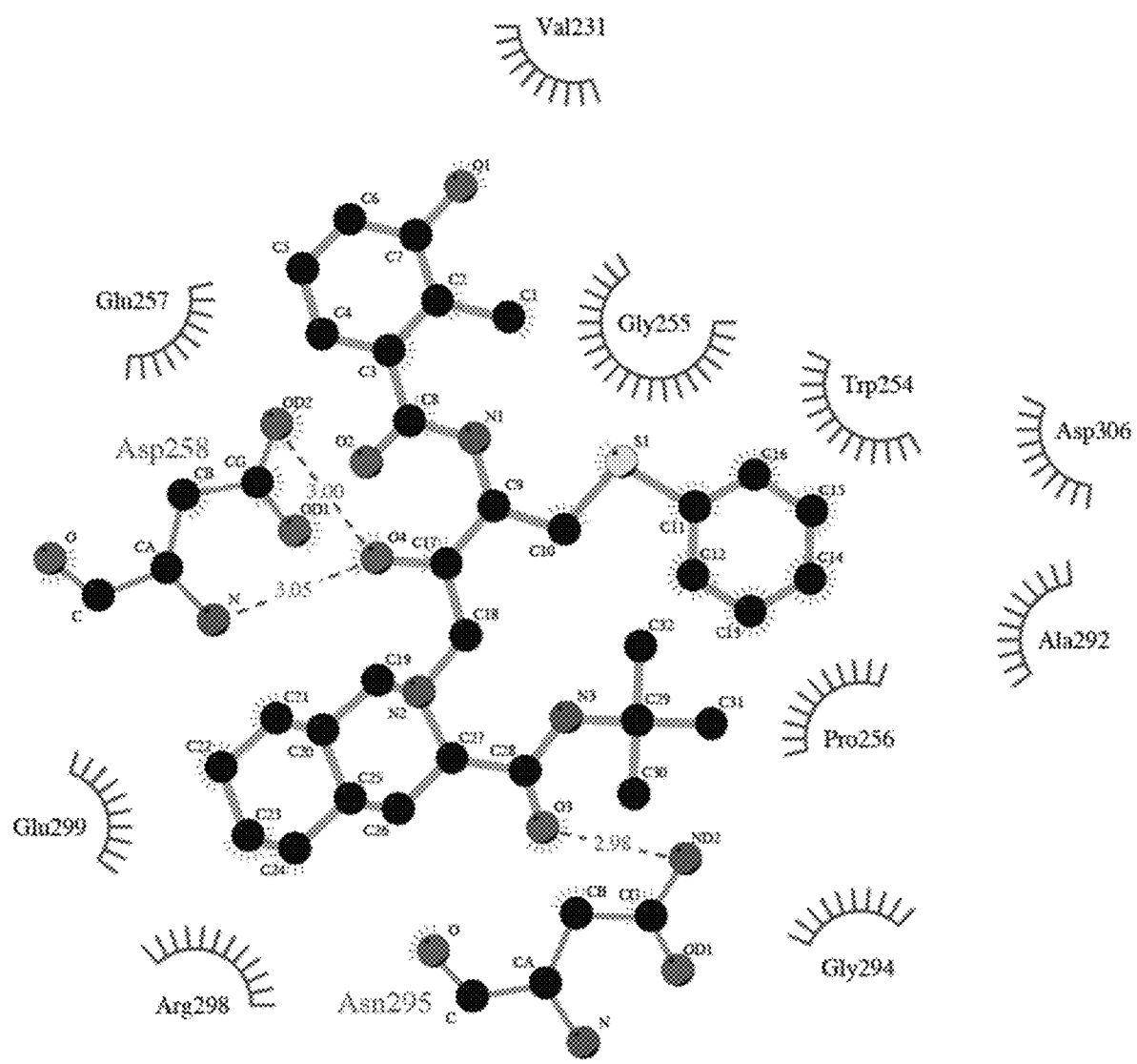
FIG. 17B shows the second conformation of nelfinavir in a LigPlot representation, showing nelfinavir forming hydrogen bonds with residues Asp258 and Asn295.
Figure 18:
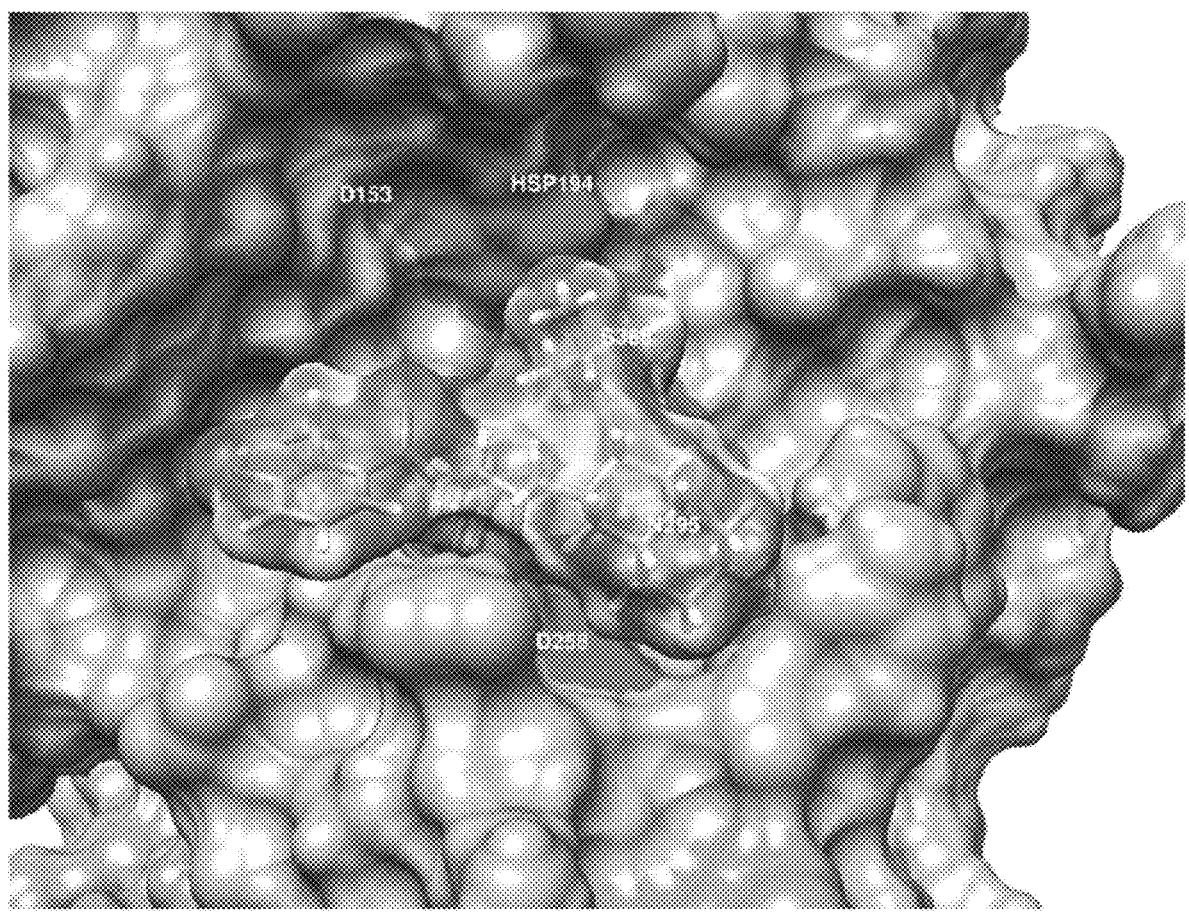
FIG. 18 depicts the surface structure illustration of nelfinavir bound to furin, with predicted binding affinity characterized as being ΔG=−12.79 kcal/mol.
Figure 20:
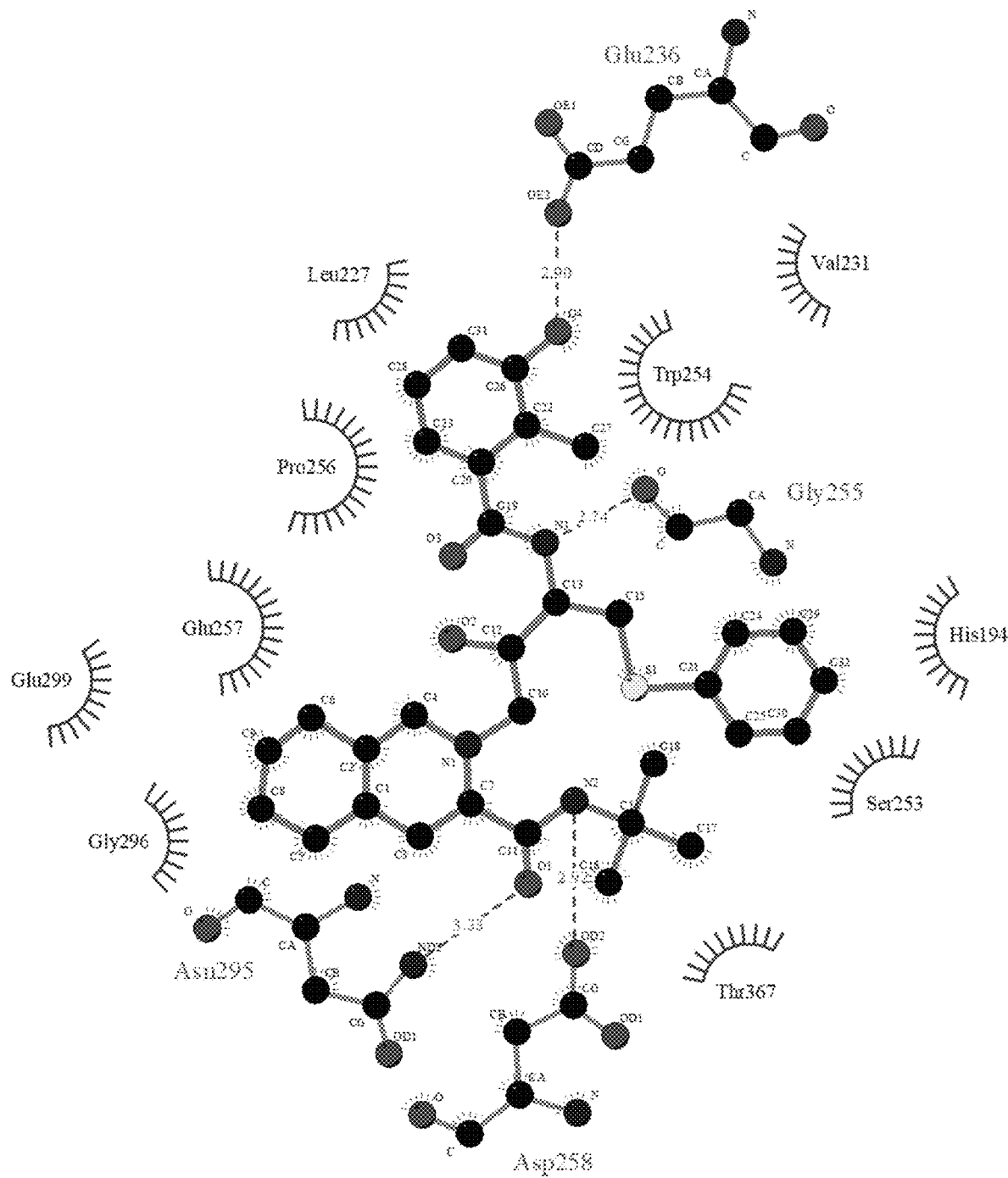
FIG. 20 shows a LigPlot representation of nelfinavir interacting with furin as characterized by DockingServer. A two-dimensional representation of the predicted interactions of nelfinavir with residues in the catalytic domain of furin is shown. Predicted hydrogen bonds are shown with dashed lines, and hydrophobic contacts are depicted with arches. Predicted hydrogen bonds are formed with residues Asn295, Asp258, Glu236, and Gly255.

Nelfinavir also showed a higher affinity (full fitness −1719.32, ΔG −9.18 kcal/mol) in a second conformation within the catalytic site (FIG. 17A). This conformation shows two predicted hydrogen bonds with residues Asp258, and one hydrogen bond with residue Asn295, as shown in the LigPlot representation (FIG. 17B and FIG. 20). FIG. 18 depicts a molecular structure illustration of nelfinavir bound to furin.

Several other PIs bound tightly to a site on furin that was not at the catalytic site of furin but in a cleft between the two major domains of furin. Protease catalysis requires both the catalytic domain and the P domain and movement between these two domains is essential for catalysis. This hinge region is essential for catalytic activity and this cleft represents a potential allosteric site. Binding of the PIs in this cleft provides an alternate mechanism of inhibiting furin.

Figure 7B:
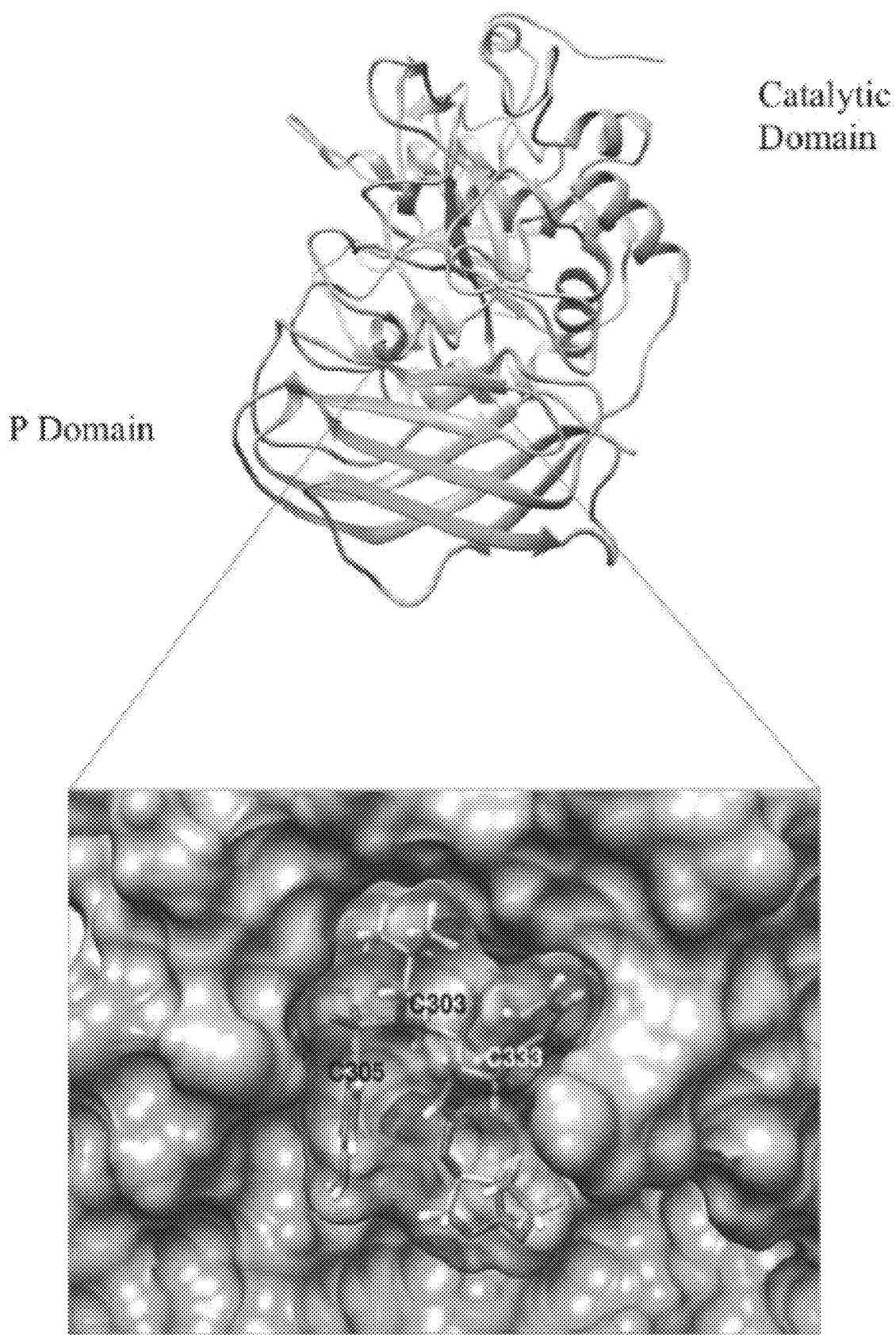
FIG. 7B depicts a surface visualization of darunavir binding to furin at the catalytic site and cysteine rich area of the P domain. Darunavir (full fitness −1794.72, ΔG −8.18 kcal/mol) is shown binding to the allosteric site.
Figure 8B:
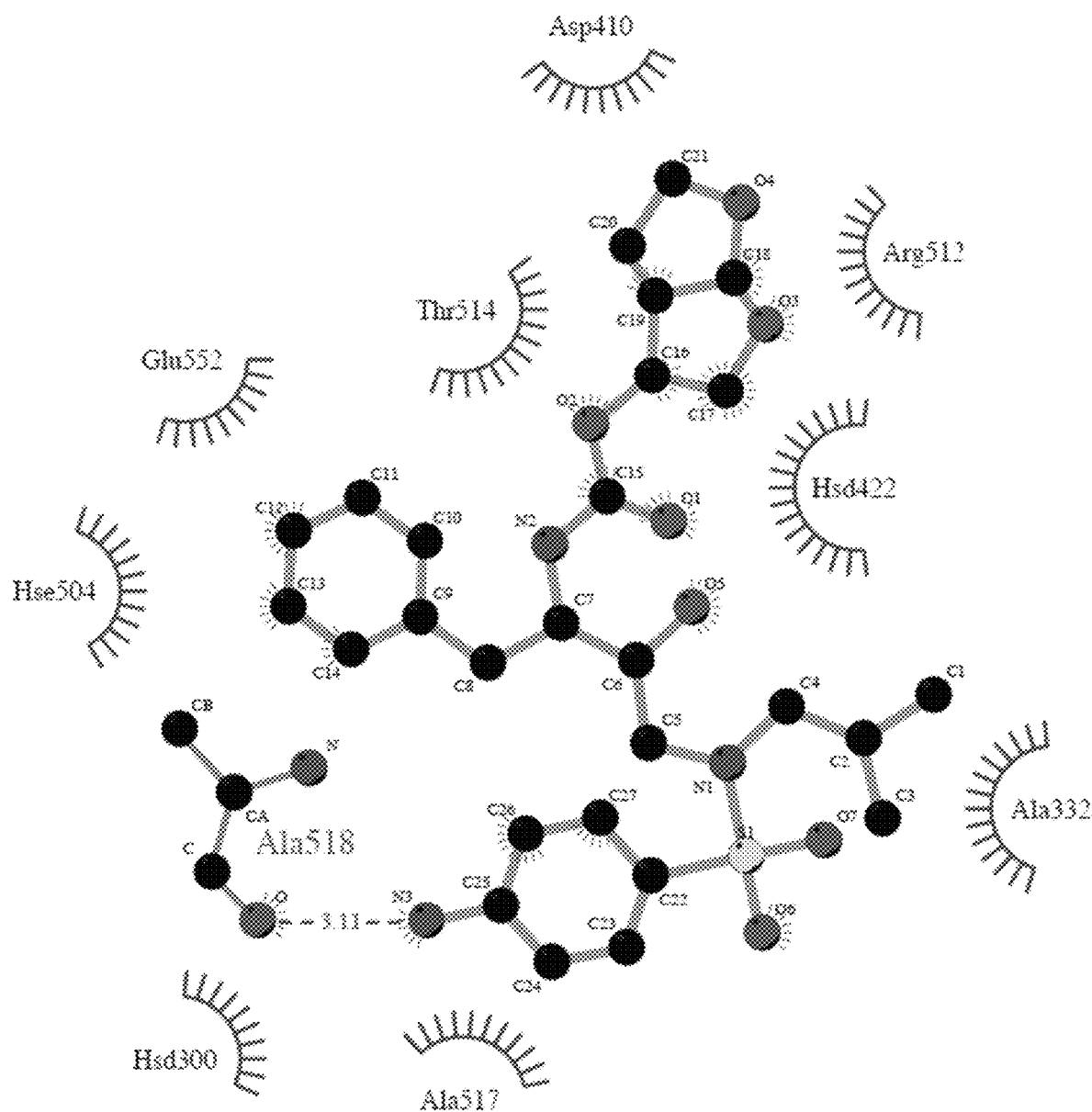
FIG. 8B illustrates a two-dimensional LigPlot representation of ligands with furin. Hydrogen bonds are depicted with dashed lines, and hydrophobic interactions are depicted as arches.
Figure 19:
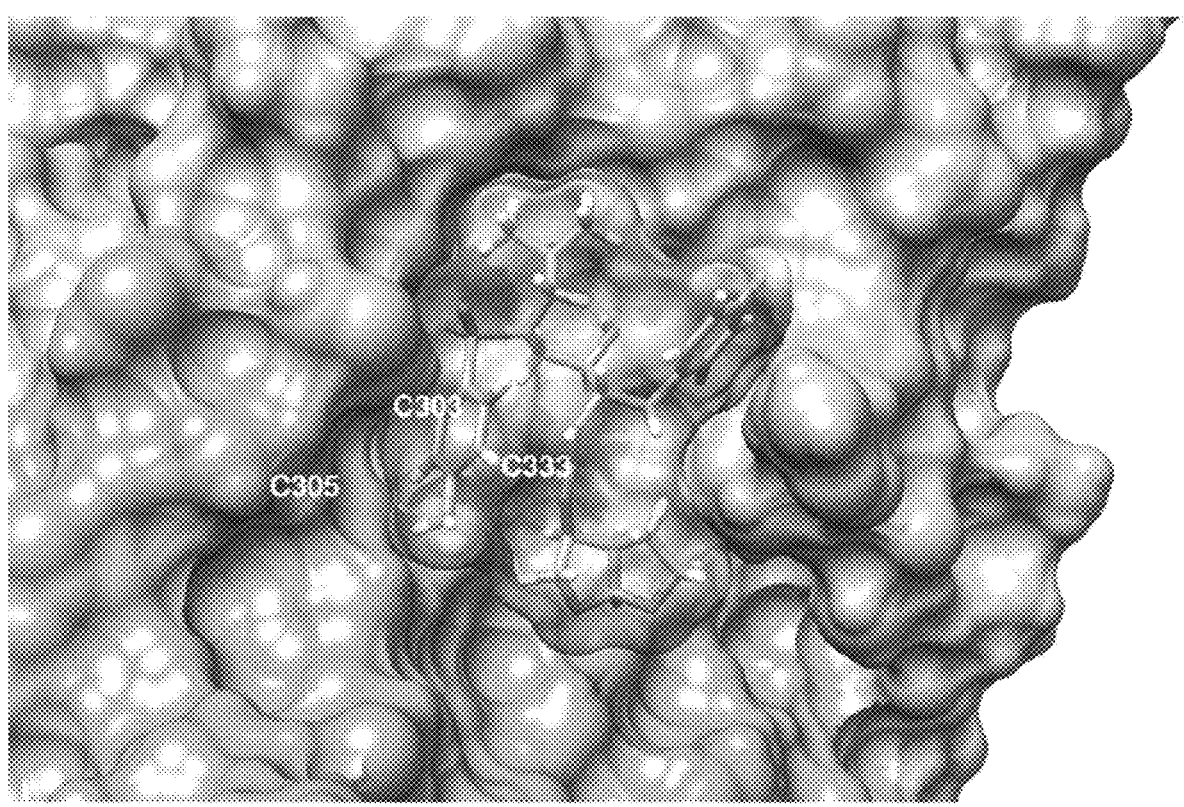
FIG. 19 depicts the surface structure illustration of darunavir bound to furin, with predicted binding affinity' characterized as being ΔG=−8.88 kcal/mol.
Figure 21:
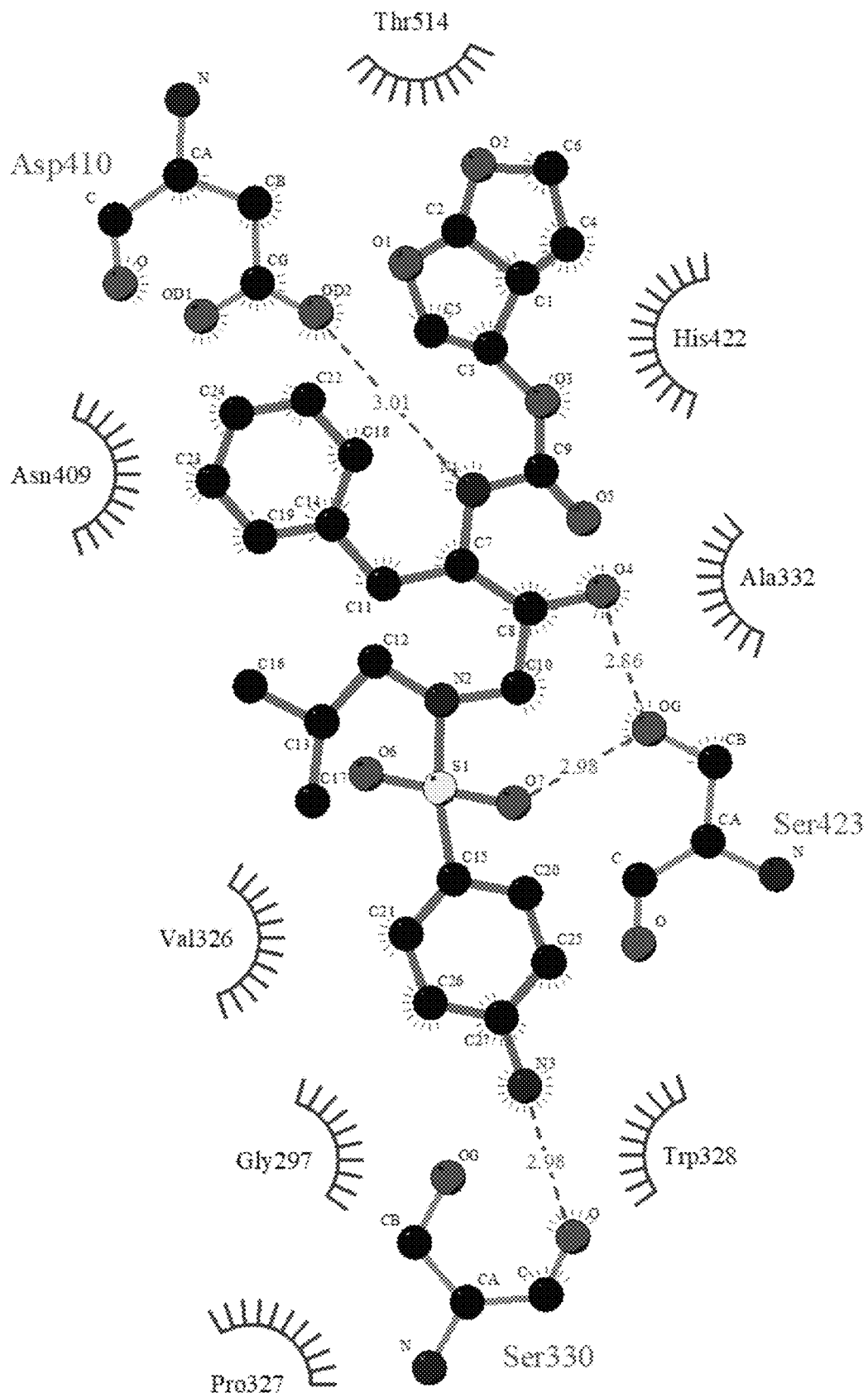
FIG. 21 shows a LigPlot representation of darunavir interacting with furin as characterized by DockingServer. A two-dimensional representation of the predicted interactions of darunavir with residues in the cysteine rich domain of furin is shown. Predicted hydrogen bonds are shown with dashed lines, and hydrophobic contacts with arches. Predicted hydrogen bonds form with residues Ser330, Ser423, and Asp410.

The structural representations from the molecular docking studies of darunavir binding at the interface of the catalytic domain and the P domain are shown in FIGS. 7B and 8B. Remarkably, darunavir showed very little affinity for binding to the catalytic site of furin. The binding of darunavir to furin (ΔG=−8.18 kcal/mol, allosteric site, FIG. 19 and FIG. 21) at this putative allosteric binding site had similar affinity as nelfinavir (ΔG=−9.18 kcal/mol, catalytic site) binding to the catalytic site. Table 2 represents the affinity for the individual PIs, identifying computational affinity for binding to furin at the catalytic site, the allosteric site, or both.

Nelfinavir showed higher affinity for the catalytic site as determined by Docking Server (Table 3). Nelfinavir has a predicted affinity for the active site (ΔG=−11.33 kcal/mol) that is similar to that of CMK with Swissdock (ΔG=−11.07 kcal/mol). In this conformation, there are three predicted hydrogen bonds—Asp258, Asn295 and Gly255. Other possible conformations that include hydrogen bonds with the residues from the catalytic triad have a lower affinity (ΔG=−9.29 kcal/mol, bonds with Asp 153 and His194 and ΔG=−9.92 kcal/mol, bonds with His194 and Ser368). Docking-Server does not provide full fitness data, but does provide a predicted computational K. value (nelfinavir K, =4.97 nM) for the C-domain and (darunavir K, =5.64 μM) for the P-domain.

TABLE 3

Ligand-Protein interaction parameters by DockingServer.

| Ligand* | Estimated -ΔG (kcal/mol) | Estimated $K_i$ | Total intermolecular energy (kcal/mol) | Hydrogen Bonds |
|---|---|---|---|---|
| Nelfinavir | −11.33 | 4.97 (nM) | −12.79 | Gly255, Asp258, Asn295 |
| Darunavir | −7.25 | 5.64 (μM) | −8.88 | Ser302, Asp410, Asp423, Thr514, Arg519 |

*Free binding energy, estimated Ki and interactions for Nelfinavir and Darunavir using furin (PDB ID 4OMC).

Example 2

In Vitro Inhibition of Furin

This example demonstrates that the predicted molecular docking studies described in Example 1 are realized using purified furin in vitro.

Figure 14B:
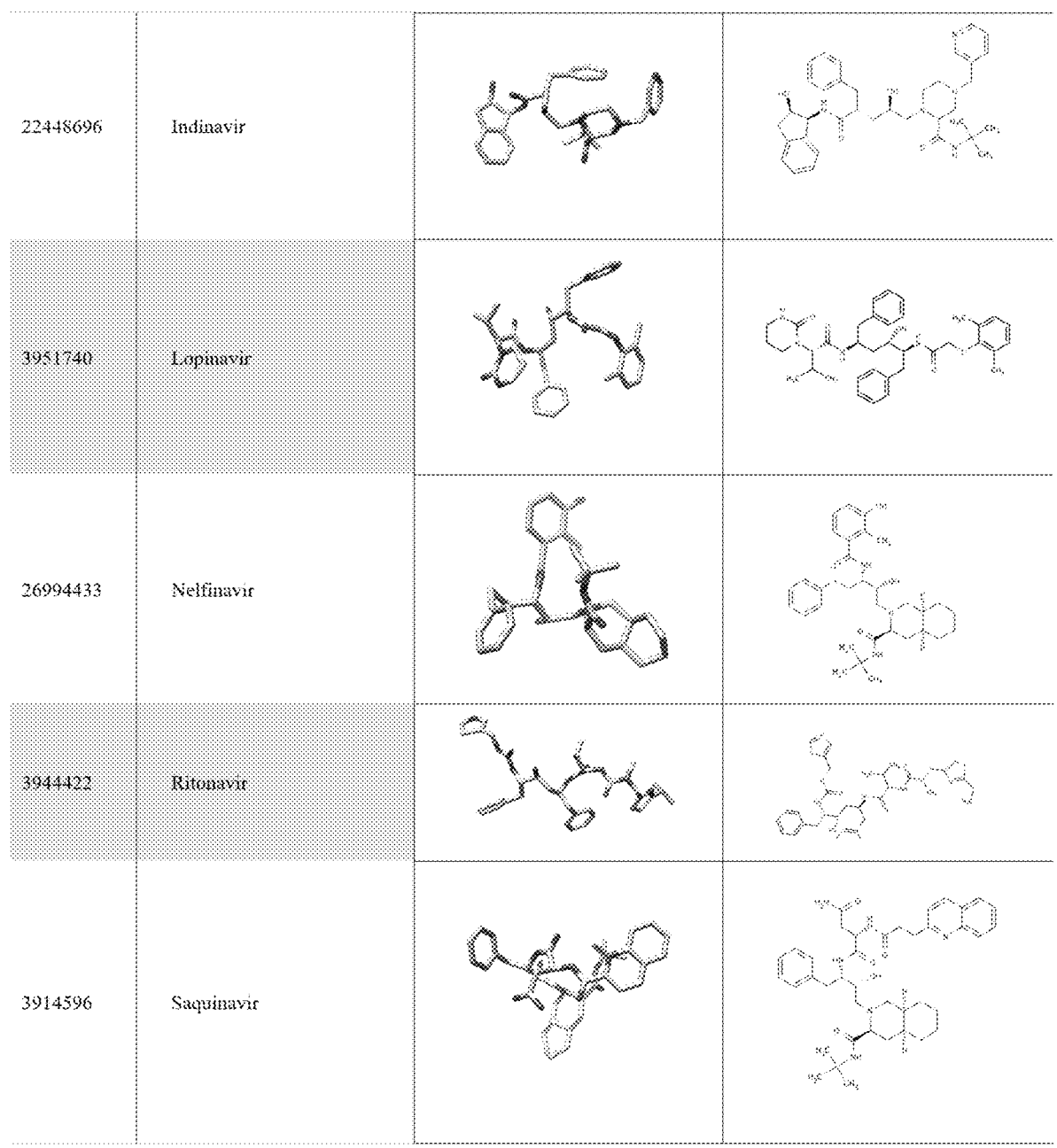
Figure 14C:
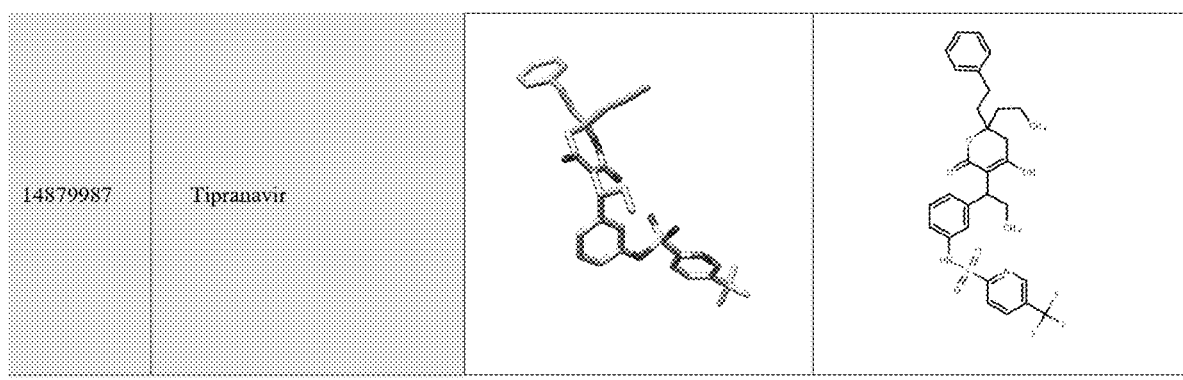

The molecular docking studies predicted that PIs bind to the catalytic site of furin as well as to a putative allosteric site on furin (FIGS. 7A and 7B). A fluorescence assay was used to monitor furin activity. Furin has substrate specificity for the multi-basic consensus amino-acid sequence of Arg-X-Lys/Arg-Arg (RXRR) at the cleavage site, where X represents a neutral, polar amino acid. Peptide substrates including the furin cleavage sequence having an attached fluorescent tag were used. A fluorescence tag is quenched when it is attached to the peptide, but when furin cleaves the peptide the fluorophore is released and is able to fluoresce. The inhibitory effect of the PIs in this assay can be characterized through a positive control, in which furin actively cleaves substrate without the presence of an inhibitor. Commercially available PIs (FIGS. 14A-C), including chloromethylketone, amprenavir, atazanavir, darunavir, indinavir, lopinavir, nelfinavir, ritonavir, saquinavir, and tipranavir were tested and the results are shown in FIGS. 7A and 7B.

Figure 9:
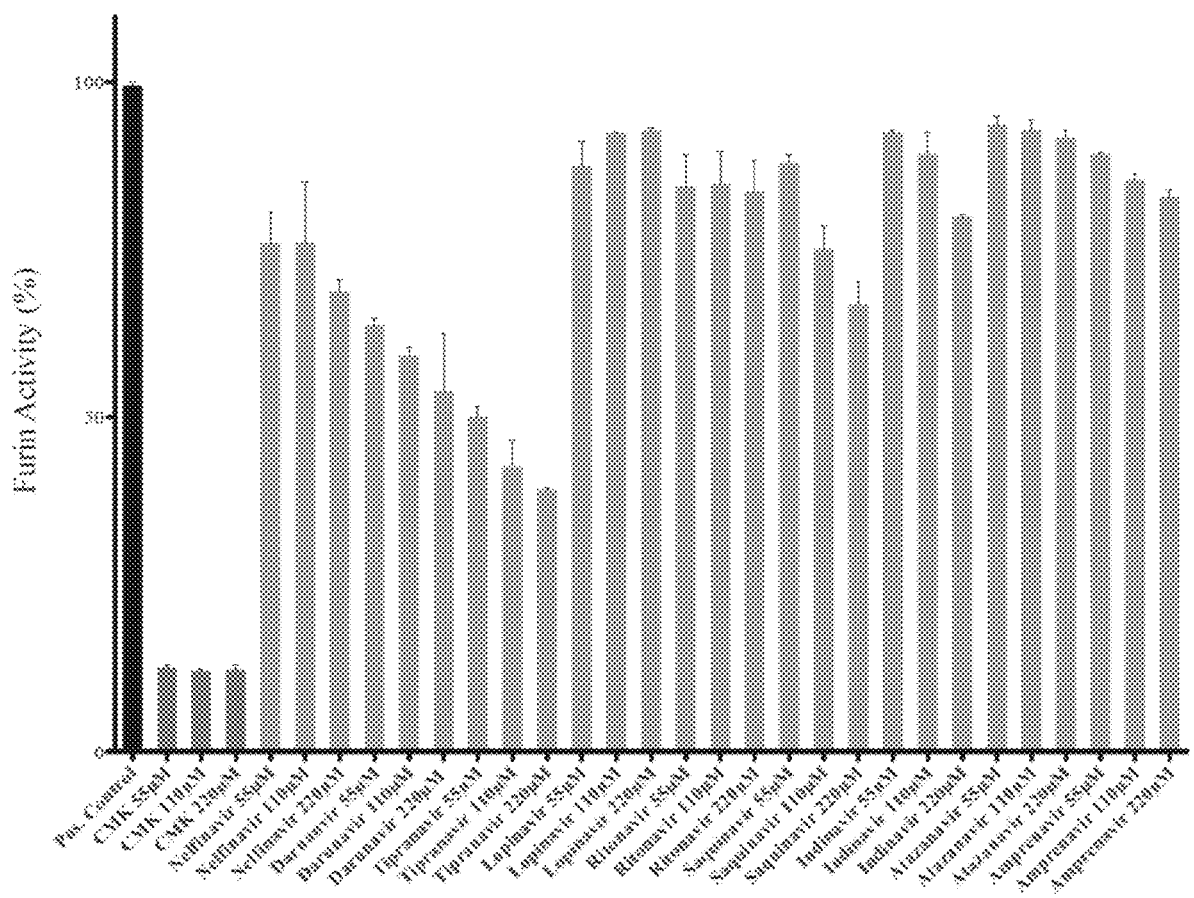
FIG. 9 shows the furin activity screen in percent furin activity versus varying concentrations of various protease inhibitors (PIs). The positive control for furin activity is all assay components without any inhibitors added. Chloromethylketone (CMK) is used as a known furin inhibitor and represents full inhibition of furin. The remaining assays include furin, substrate and the indicated concentration of the PI.

In general, the predicted inhibition of furin by PIs was consistent with the predictions from the molecular docking studies, as illustrated in FIG. 9. Tipranavir, darunavir, and nelfinavir were the three best inhibitors as predicted by the molecular docking. Darunavir did in fact inhibit furin activity even though it bound at an allosteric site between the catalytic domain and the P domain of furin and not at the active site.

Figure 10A:
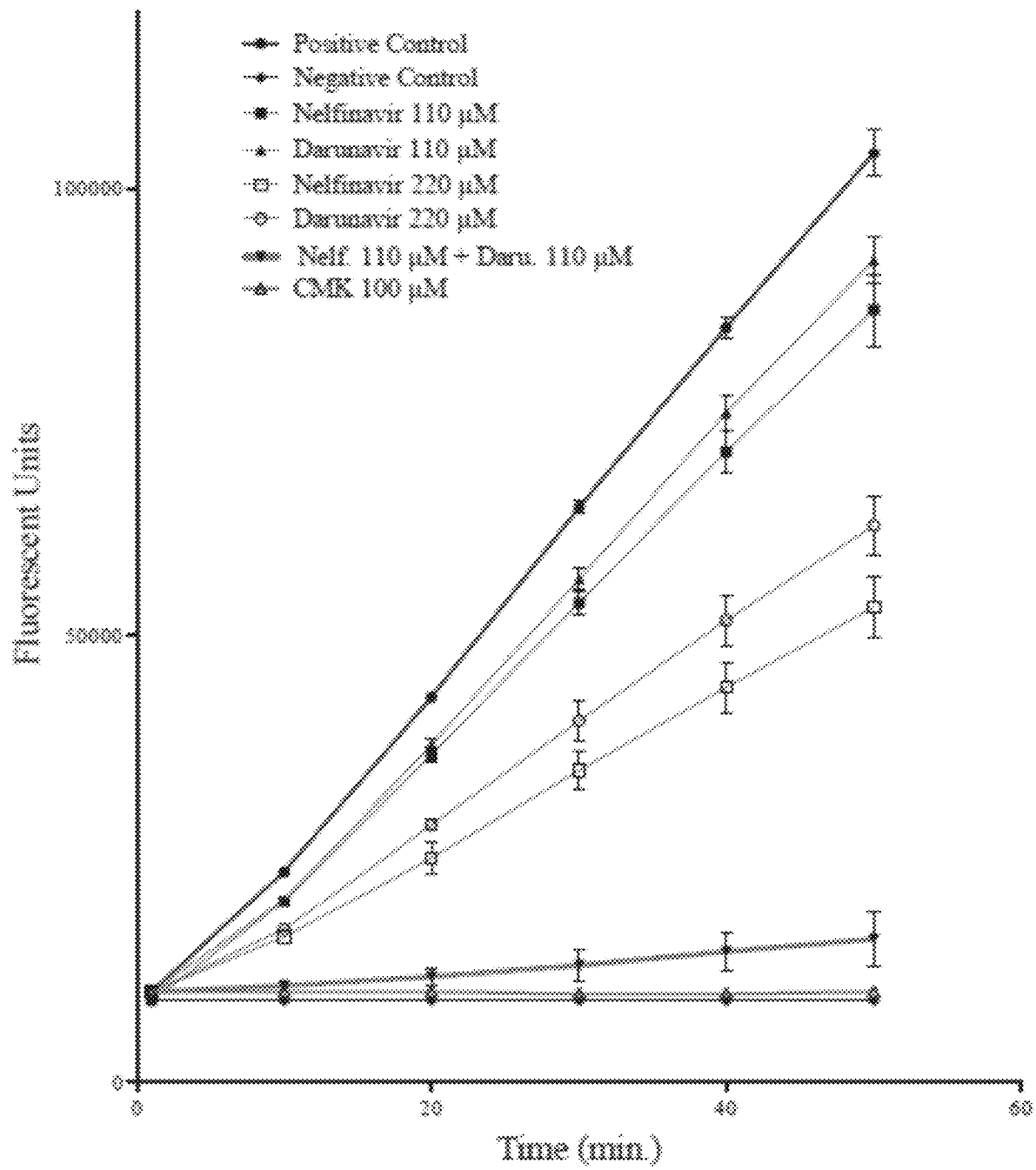
FIG. 10A shows the inhibition of furin in vitro. Known furin inhibitor CMK is used as an inhibitor control, while the positive control lacks the presence of an inhibitor. An additional negative control lacks the presence of furin. Furin activity is shown over a 50-minute time course.
Figure 10B:
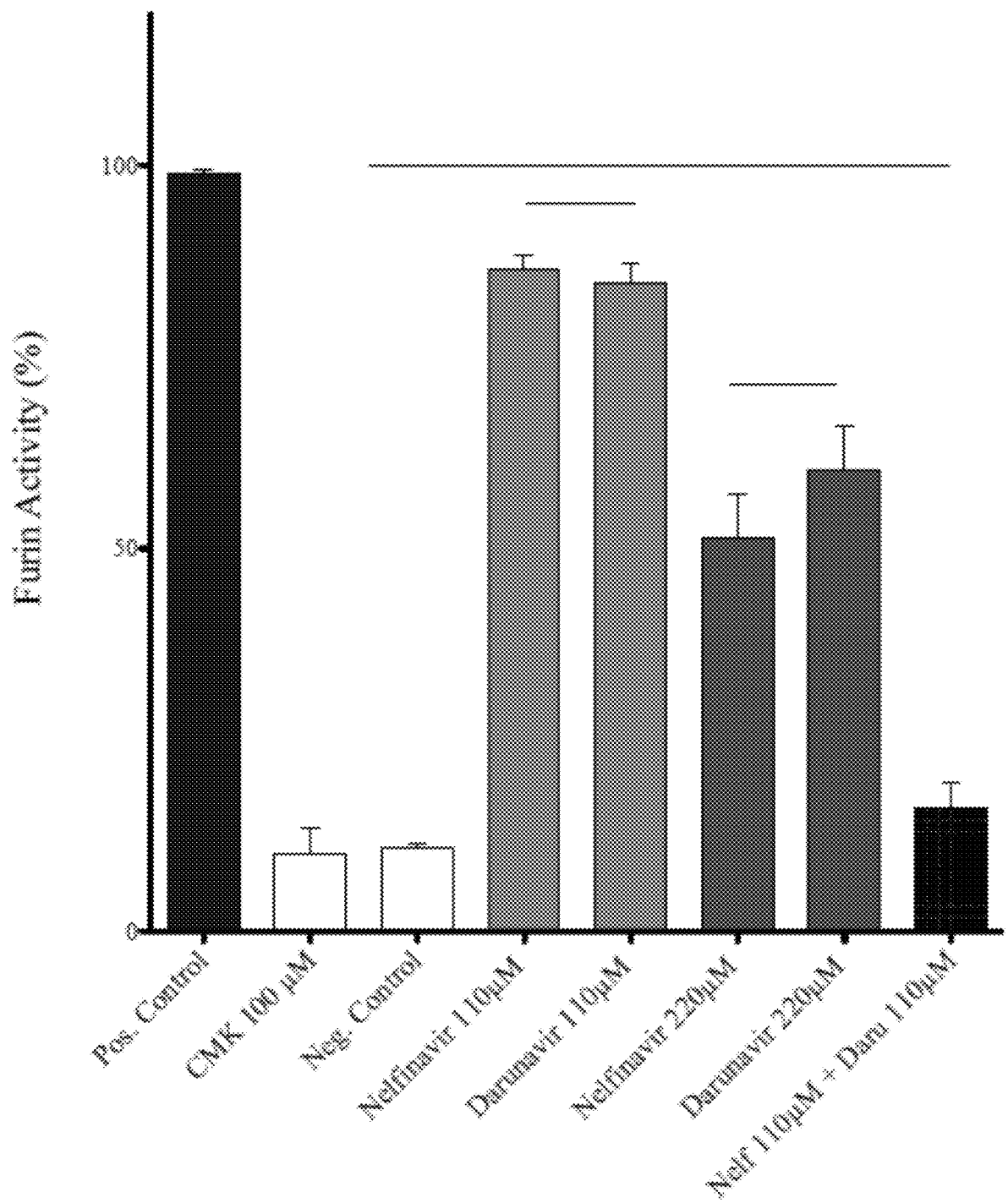
FIG. 10B is a graphical representation of the percent furin activity at an endpoint of 50 minutes.
Figure 15A:
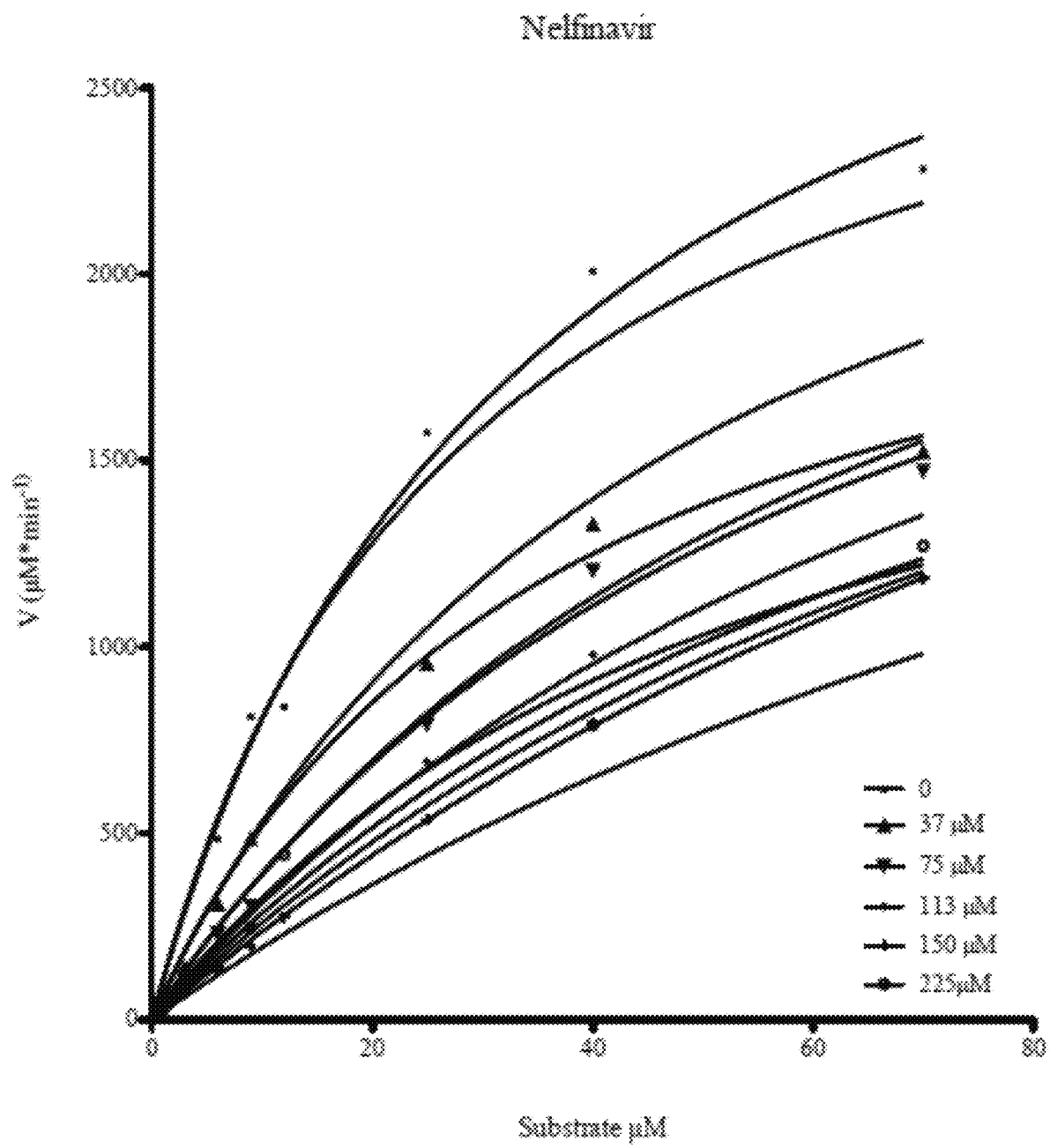
FIGS. 15A-B show the Michaelis-Menten plots for nelfinavir (FIG. 15A) and darunavir (FIG. 15B).
Figure 15B:
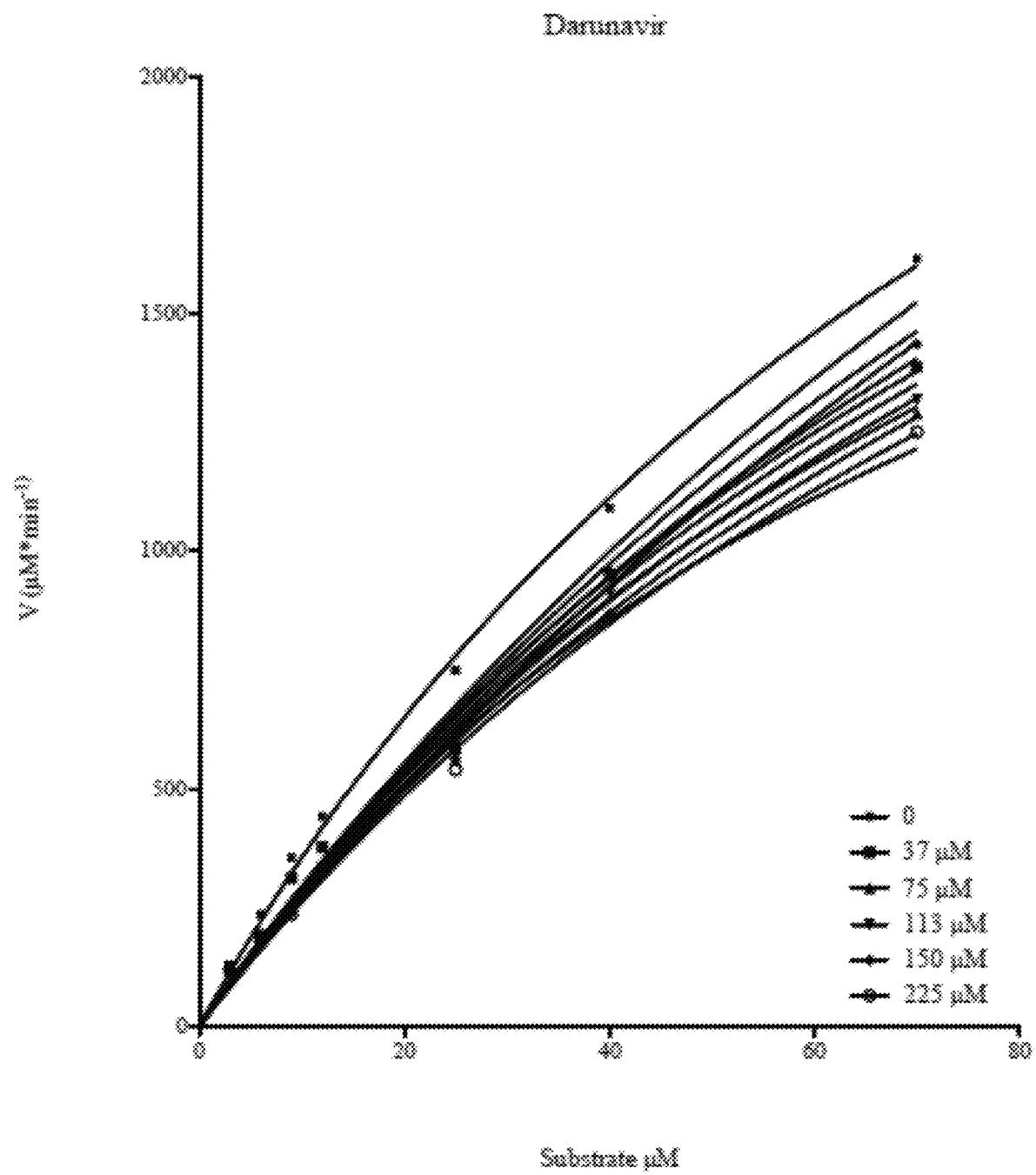

PIs offering the fewest physiological side effects are of the highest interest. Thus, additional studies with nelfinavir and darunavir were conducted. Nelfinavir represents catalytic site inhibitors and darunavir represents allosteric site inhibitors. FIG. 10A shows decreased fluorescence caused by the presence of darunavir or nelfinavir at two different concentrations (110 and 220 μM). The potential synergistic effect when the two drugs are combined was also tested (nelfinavir 110 μM+darunavir 110 μM), as these drugs are predicted to bind to different sites. The combined drug treatment gave a synergistic effect, consistent with inhibition occurring at the catalytic site as well at the allosteric site. FIG. 10B is a graphical representation showing the positive control at 100% and each reaction with the different protease inhibitors as a percent of the positive control. The Lineweaver-Burk statistical transformations (FIGS. 11A-B and FIG. 16), the Michaelis-Menten plots (FIGS. 15A and 15B), and the predicted computational binding affinity data are consistent with the binding of darunavir at an allosteric site indicating uncompetitive inhibition, whereas nelfinavir portrays competitive inhibition.

Example 3

Inhibition of Turin in Hepatocytes

This examples demonstrates the efficacy of inhibiting furin in hepatocyte cell cultures with protease inhibitors, thereby reducing hepcidin secretion by hepatocytes.

The hepatoma cell line Huh7 has been used previously to demonstrate the secretion of hepcidin in response to inflammation as a model for ACL. Because hepcidin is synthesized in a precursor form called prohepcidin with furin, specifically cutting prohepcidin into the active hormone hepcidin, protease inhibitors should act to inhibit furin and prevent the cleavage of prohepcidin into hepcidin.

Figure 12:
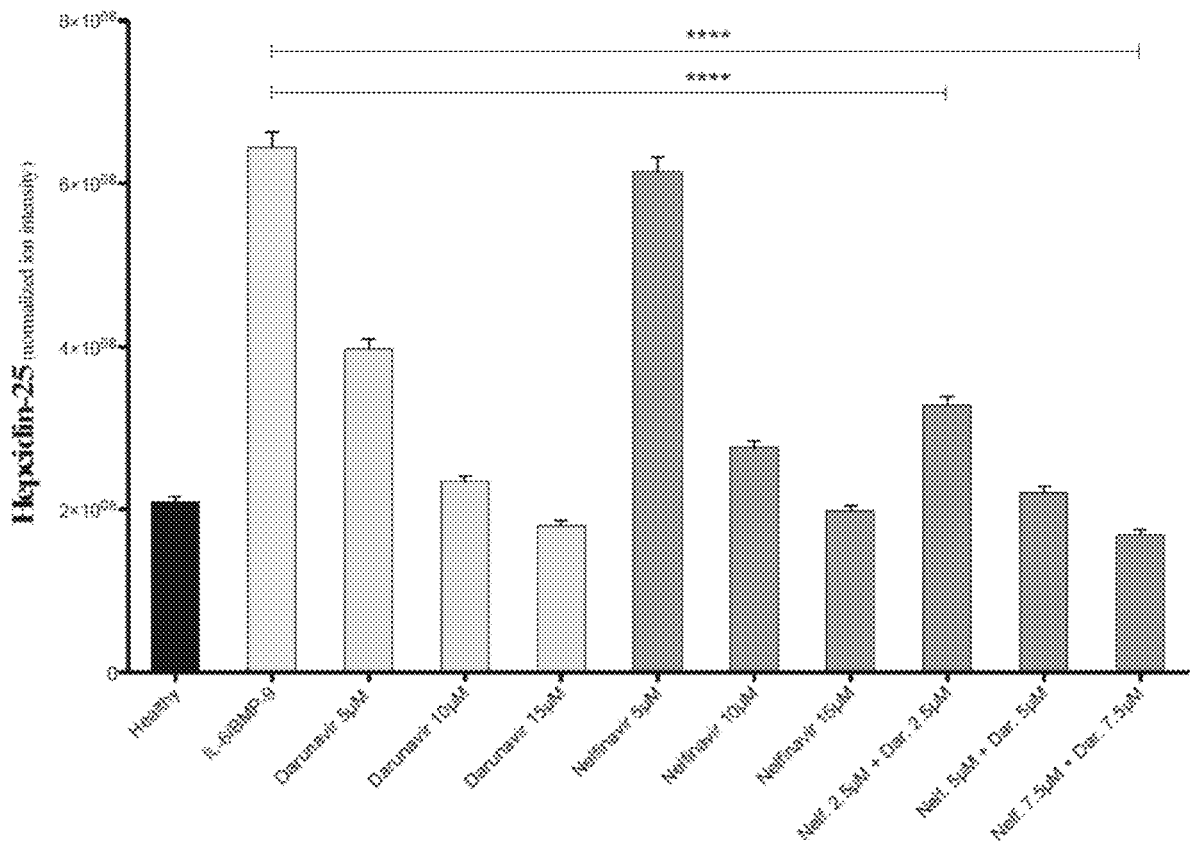
FIG. 12 shows hepcidin-25 quantification in Huh7 cell media. LTQ-Orbitrap XL mass spectrometer total ion intensity of hepcidin-25 in Huh7 cell media of cells not treated (Black), cells treated with inflammatory cytokines (IL-6 and BMP-9) and cells treated with inflammatory' cytokines and with protease inhibitors (PIs) at the indicated concentrations to inhibit hepcidin activation and secretion. IL-6 was induced alongside BMP-9 at a concentration of 10 ng/mL each for all cell groups except healthy control. Healthy PI treated control group showed no significant change in hepcidin-25.

Huh7 cells were treated with and without inflammatory cytokines (IL-6 and BMP-9) and treated with PIs to inhibit furin. Mature hepcidin-25 secreted into the media from differing cell groups was collected and quantified by mass spectrometry (FIG. 12). As shown in FIG. 12, PI treatment potently inhibits hepcidin secretion from inflamed cells under these conditions. These results demonstrate that PIs, particularly nelfinavir and darunavir, are potent potential therapeutics to inhibit furin and prevent ACL Example 4

Determination of the Mechanism of Protease Inhibitor Inhibition of Furin

This example demonstrates the mechanism of PI inhibition by evaluating: 1) which of the PIs are STAT or SMAD inhibitors; 2) the concentration dependence of the PIs on STAT or SMAD pathway inhibition versus the inhibitory concentration for furin inhibition; and 3) whether PIs have a dual role as transcription inhibitors and activation inhibitors by inhibiting both STAT/SMAD and furin.

Hepcidin is a principal regulator of iron metabolism. During conditions of chronic immune activation, hepcidin production increases. Cytokines stimulate STAT or SMAD signaling pathways that activate the HAMP gene encoding for Hepcidin. Hepcidin is synthesized as preprohepcidin, and is targeted to the ER/Golgi for secretion. In the ER, the targeting sequence is cleaved and prohepcidin is further processed by furin to produce active hepcidin. In serum hepcidin binds to the iron export protein ferroportin, causing endocytosis and degradation. The removal of ferroportin from cells prevents dietary iron absorption and prevents iron redistribution, and resulting in anemia. Inhibition of hepcidin results in stable ferroportin expression and normal iron release from cells as a pathway for future treatment of anemia.

Example 3 shows the inhibited secretion of hepcidin from hepatocytes by-inhibiting furin with PIs. Nelfinavir, which was particularly efficacious, is also a known STAT3 inhibitor.

A well-established model of inflammation was used to stimulate hepcidin production in the immortalized Huh7 and HepG2 hepatocyte cell lines (Kartikasari, A. E. R. et al. Secretion of bioactive hepcidin-25 by liver cells correlates with its gene transcription and points towards synergism between iron and inflammation signaling pathways. *Biochim. Biophys. ActaBBA—Proteins Proteomics* 1784, 2029-2037 (2008)).

Of the PIs tested, only nelfinavir showed the capability of inhibiting STAT3 phosphorylation in a dose dependent manner. PIs did not significantly inhibit SMAD phosphorylation, although nelfinavir did have a significant inhibitory effect in HAMP gene expression (p<0.05). Prohepcidin concentrations significantly increased (p<0.0001), while hepcidin markedly decreased (p<0.0001) with co-treatment of nelfinavir and darunavir and inoculation of inflammatory cytokines IL-6 and BMP-9. Similar results trended with both Huh7 and HepG2 hepatocyte cell lines.

By employing a LTQ Orbitrap XL mass spectrometer calibrated with hepcidin isoforms, hepcidin-25 secretion from Huh7 and HepG2 immortalized hepatocyte cell lines were identified.

To activate expression of hepcidin, Huh7 and HepG2 cells were induced with 10 ng/mL IL-6 and 10 ng/mL BMP-9 for 18 hours. Treatment groups were co-induced with PIs at varying concentrations (5, 10, 15 µM). These concentrations represent physiological concentrations as measured in serum of HIV treated patients. The concentrations are selected due to their relevancy in biological environments, as shown in previous human pharmacokinetic studies (Falzacappa, M. V. V. et al. STATS mediates hepatic hepcidin expression and its inflammatory stimulation. *Blood* 109, 353-358 (2007)).

Each of nelfinavir and darunavir (15 µM) successfully inhibited the production of mature secreted hepcidin back to basal levels (FIG. 12). Interestingly, when combined at 2.5 µM each, nelfinavir and darunavir exhibited 49% inhibition of hepcidin compared to IL-6/BMP-9 controls (p<0.0001). This synergistic effect of nelfinavir and darunavir was exploited in further experimentation to inhibit furin, and consequently to blunt hepcidin production.

To assess whether PIs abrogate the IL-6 signaling cascade, STATS phosphorylation (pSTAT3) was measured in the hepatocyte cell lines. PIs were incubated with both Huh7 and HepG2 cell lines for 3 hours, before the addition of IL-6 (50 ng/mL) for 30 minutes. Concentrations of PIs ranged from 0-60 µM. Following 30 minutes of IL-6 induction, cells wore immediately lysed, and proteins harvested for Western blot analysis. Untreated hepatocyte control cells are designated as healthy.

Figure 24A:
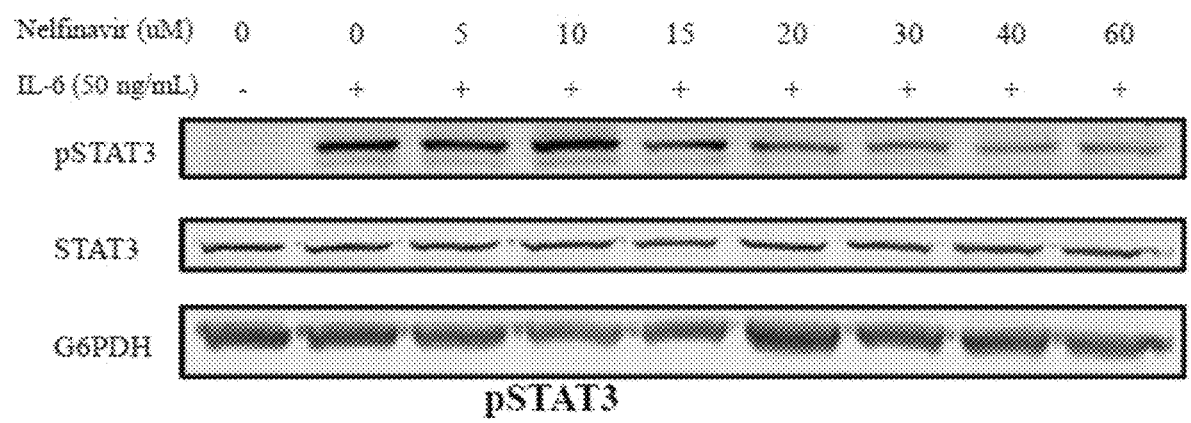
FIGS. 24A-C show the results of the dose dependent inhibition of pSTAT3 by nelfinavir and ritonavir. Neither darunavir nor indinavir inhibits STAT3 phosphorylation. Cells wore incubated with or without PIs (nelfinavir, ritonavir, darunavir, or indinavir) at (0, 15, 30, or 60 µM) for 3 hrs prior to 30 min induction with 50 ng/mL IL-6.
Figure 24B:
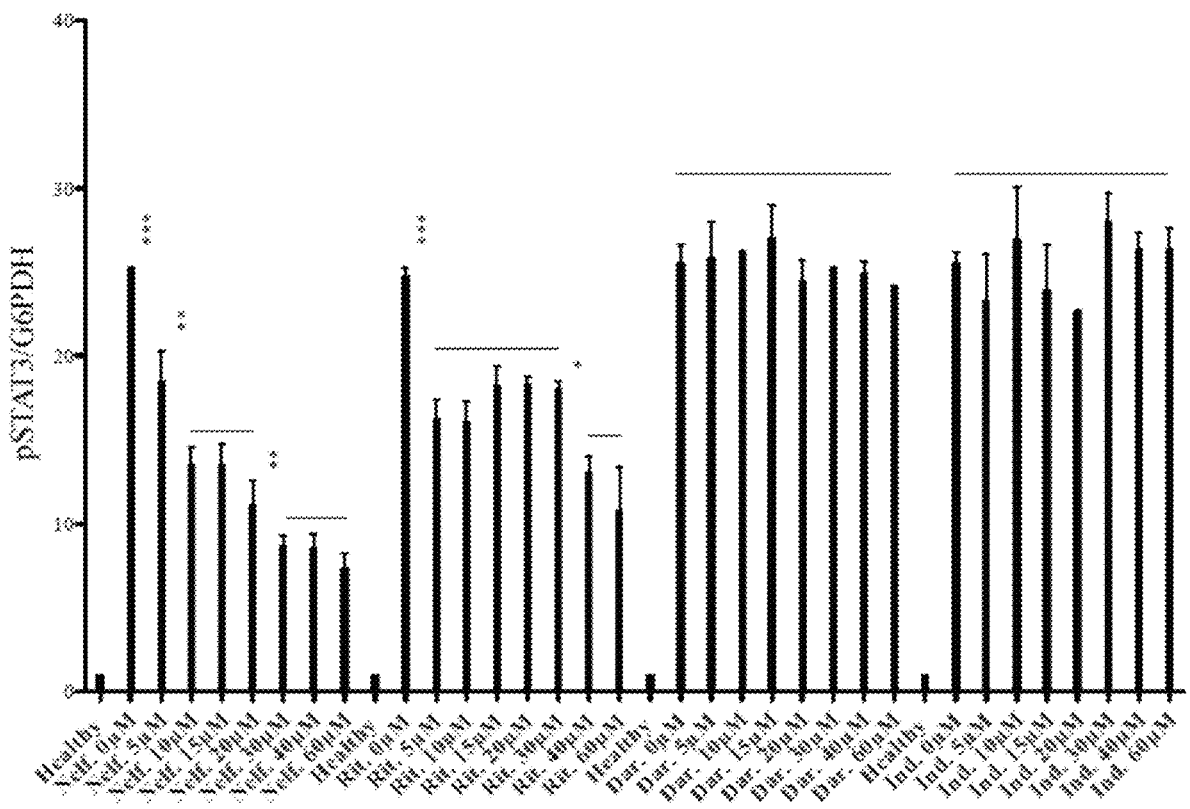
Figure 24C:
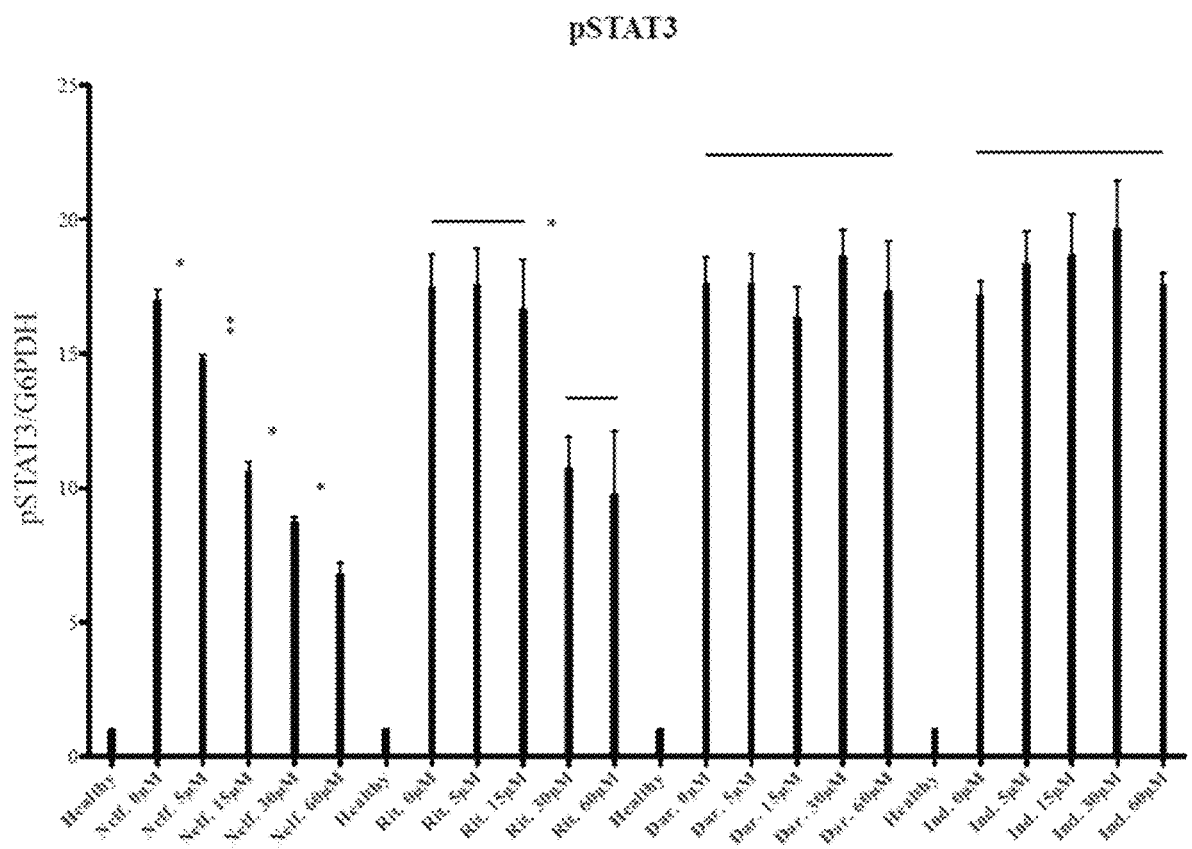

Previous research has shown the ability of PIs to inhibit pSTAT3 in multiple myeloma cell lines (Babitt, J. L. et al. Modulation of bone morphogenetic protein signaling in vivo regulates systemic iron balance. *J. Clin. Invest.* 117, 1933-1939 (2007)). Research has also shown PIs ability to induce IL-6 secretion in cultured adipocytes (1.8 to 2.0 fold). As described herein, pSTAT3 is inhibited in activated hepatocytes by nelfinavir in a dose dependent manner, showing significant average (27%) inhibition at 5 µM (p<0.001), and 46% inhibition at 15 µM (p<0.001) (FIGS. 24A-B). Ritonavir also displayed significant average pSTAT3 inhibition (27%) (p<0.001) at doses 5-30 µM, of which no significant difference is shown between concentrations (p>0.05). Both darunavir and indinavir exhibit no signs of pSTAT3 inhibition, regardless of dose (p>0.05). Similar results are observed and reported in HepG2 hepatocytes (FIG. 24C).

Figure 25A:
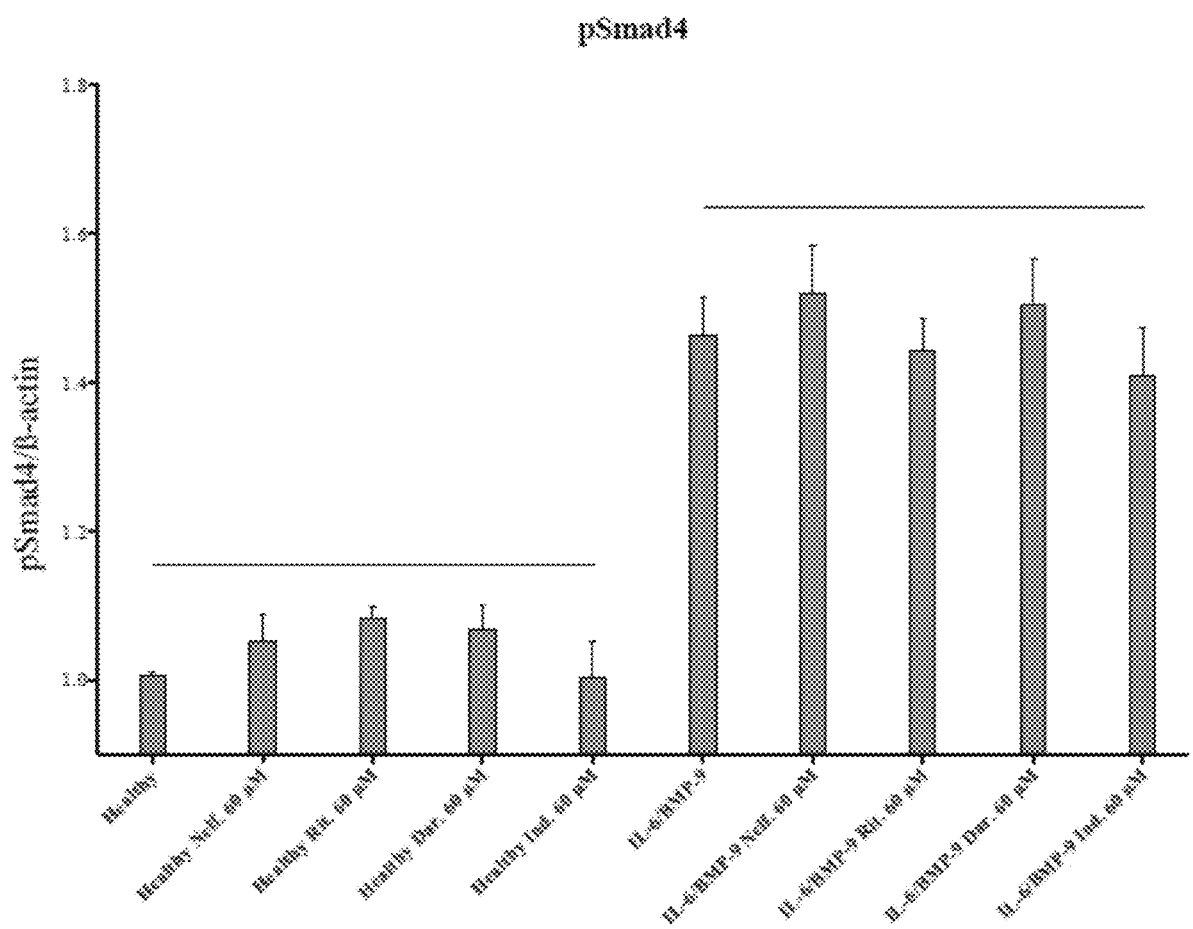
FIGS. 25A-D show the results of phosphorylation of Smad4 and Smadl/5 with induction of BMP-9 and treatment with PIs. Cells were incubated for 3 hrs with or without PIs (nelfinavir, ritonavir, darunavir, or indinavir) at (0, 15, 30, or 60 µM) prior to 30 min induction with 50 ng/mL BMP-9.
Figure 25B:
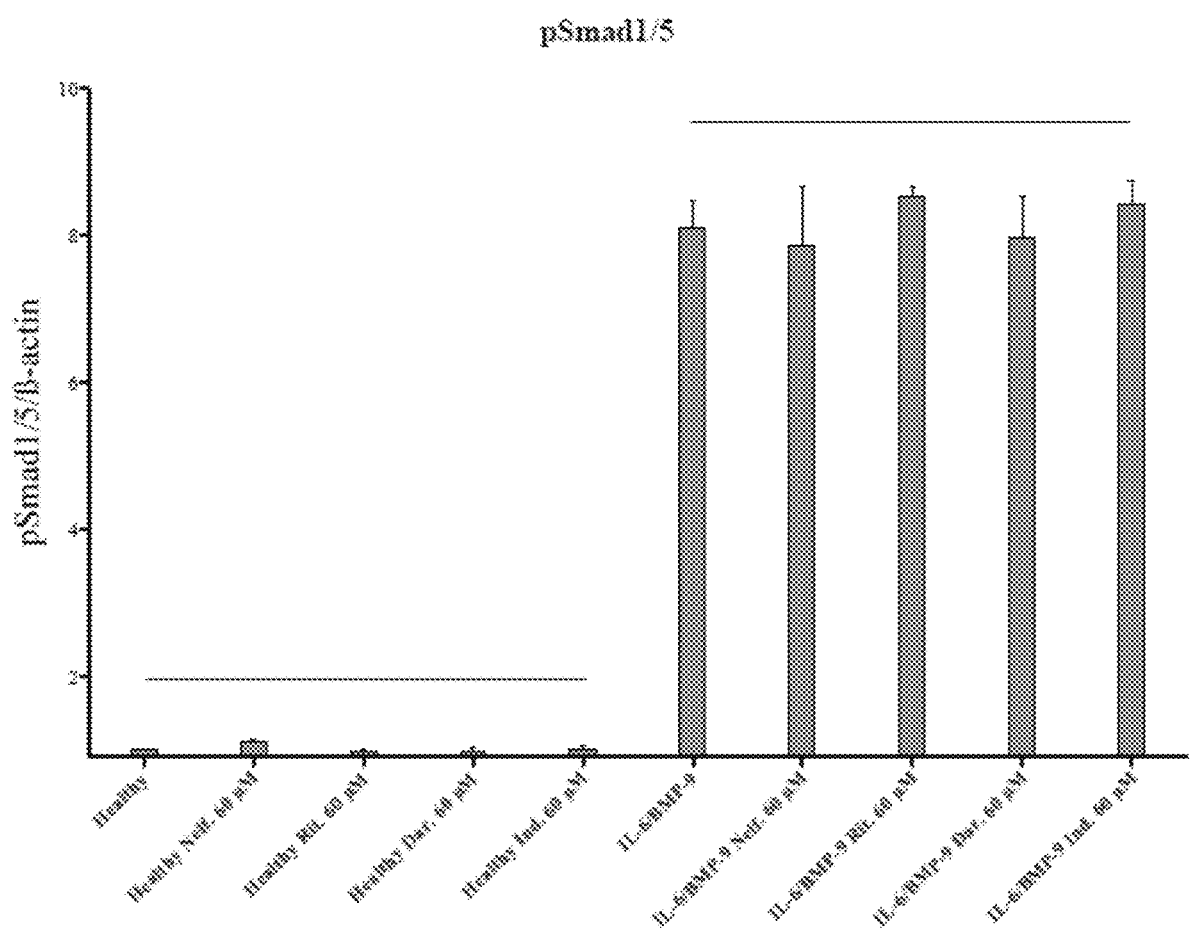
Figure 25C:
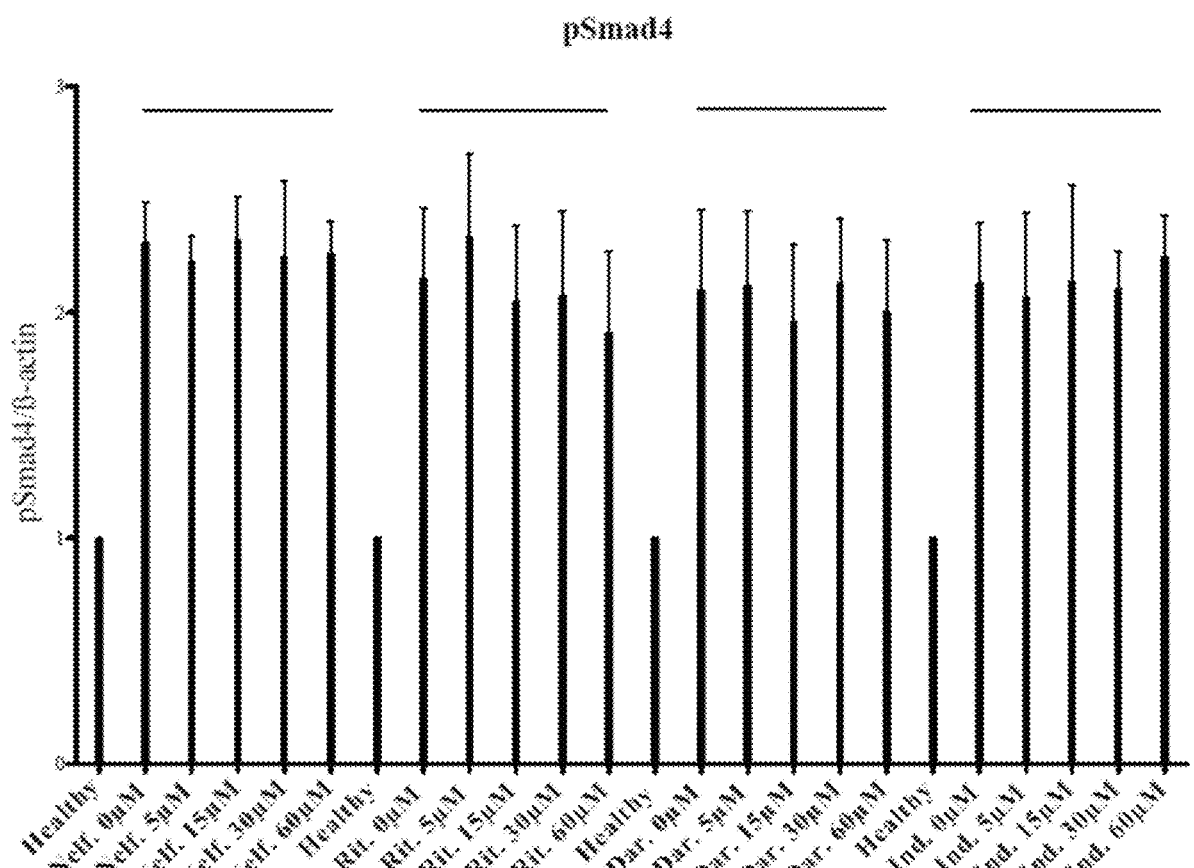
Figure 25D:
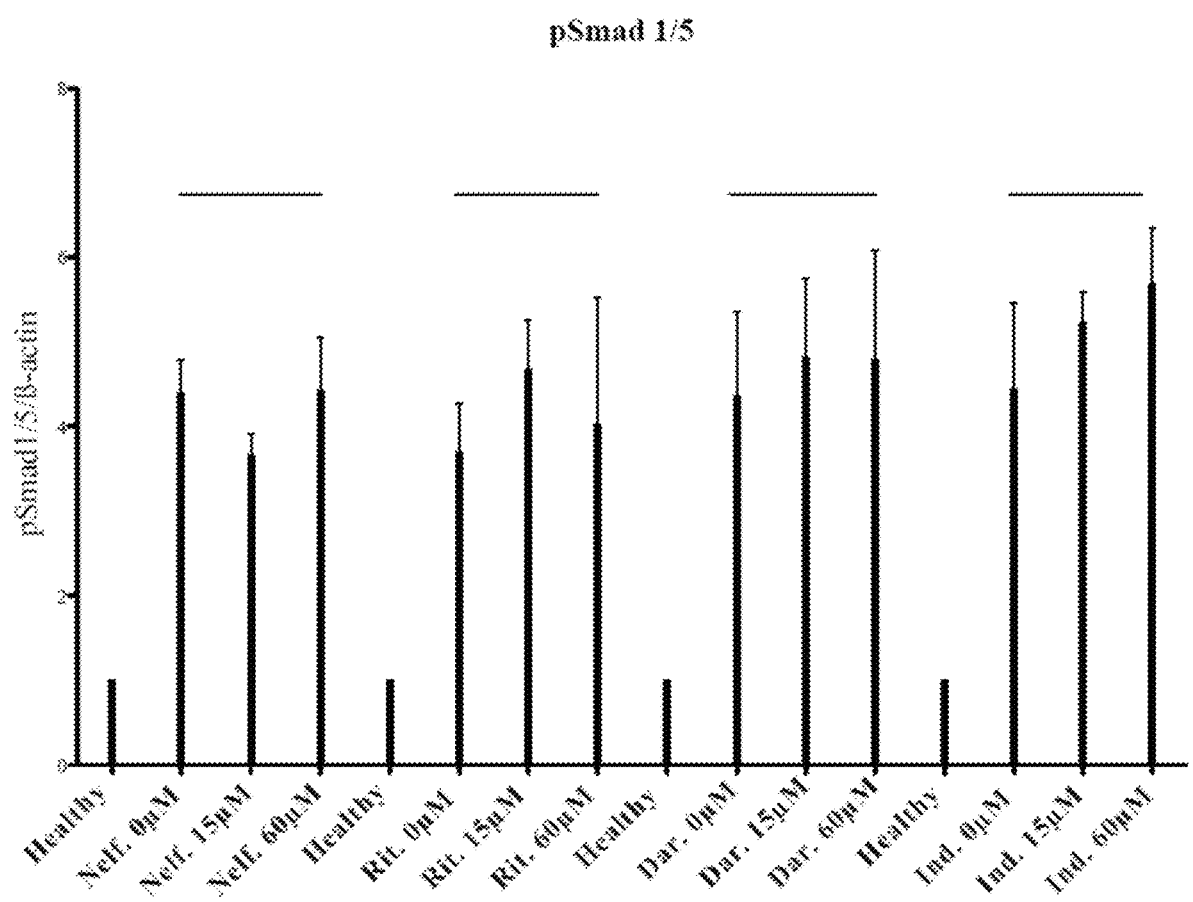

PIs were examined for their effects on phosphorylation of Smad4 (pSmad4) and Smadl/5 (pSmad1/5). Similar experiments were carried out as referred to above for EL-6/STAT3 inhibition. PIs (60 µM) were incubated with both Huh7 and HepG2 cell lines for 3 hours, before application of BMP-9 (50 ng/mL) for 30 minutes. Cells were then immediately lysed, and proteins harvested for Western blot. Untreated hepatocyte control cells are designated as healthy. Despite significant escalation in pSmad4 and pSmad1/5 in response to BMP-9 induction, co-induction of PI showed no significant effect (p>0.05) in comparison to controls in Huh7 (FIGS. 25A and 25B) and HepG2 cell lines (FIGS. 25C and 25D).

Figure 26A:
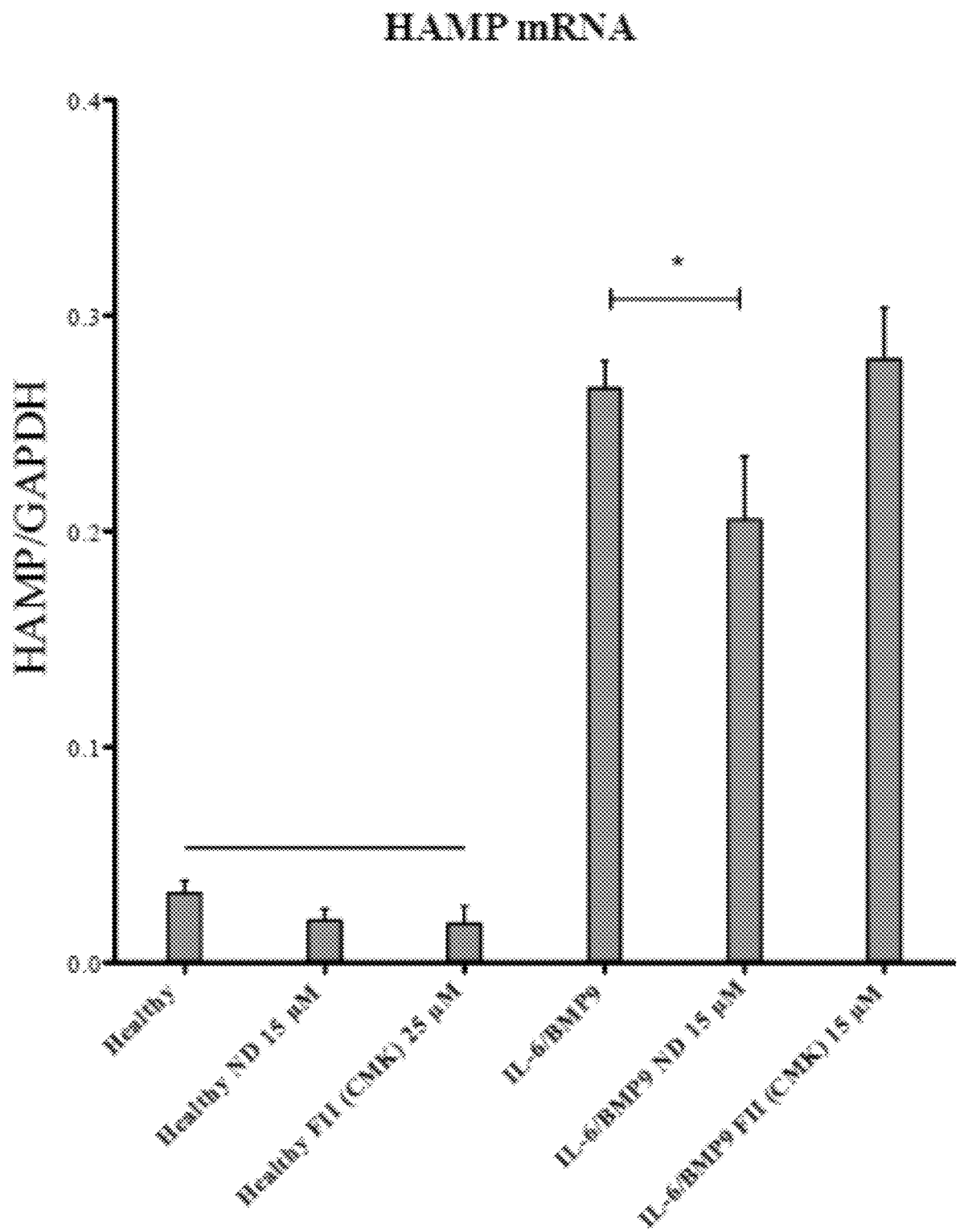
FIGS. 26A-C show the results of HAMP gene expression and prohepcidin secretion. Cells were co-treated with PIs nelfinavir (7.5 µM) and darunavir (7.5 µM) with and without cytokines EL-6 (10 ng/mL) and BMP-9 (10 ng/mL) for 18 hrs. Furin inhibitor II (FIT), CMK, was included as a known furin inhibitor at 25 µM.

Huh7 cells treated with combined nelfinavir/darunavir (ND) (15 µM) exhibited significant reduction in HAMP gene expression (FIG. 26A). This inhibition is due to the pSTAT3 inhibitory effect of nelfinavir, since darunavir did not show any inhibition of pSTAT3 phosphorylation, and also due to elevated prohepcidin levels. Previous studies have shown prohepcidin's ability to bind to the STAT3 HAMP promoter and autoregulate its own expression (Munoz, M., Garcia-Erce, J. A. & Remacha, À. F. Disorders of iron metabolism. Part II: iron deficiency and iron overload. *J. Clin. Pathol.* 64, 287-296 (2011)). Increased levels of prohepcidin reduce HAMP expression in WRL68 hepatocyte cell lines. As such, the rise in IL-6/BMP-9 ND treated prohepcidin also accounts for a lowered HAMP expression within the same group. However, with IL-6/BMP-9 CMK treatment, this phenomenon was not observed. Therefore, the reduction of HAMP gene expression with ND treatment in IL-6/BMP-9 induced cells is due to partial inhibition of pSTAT3 by nelfinavir.

Figure 26B:
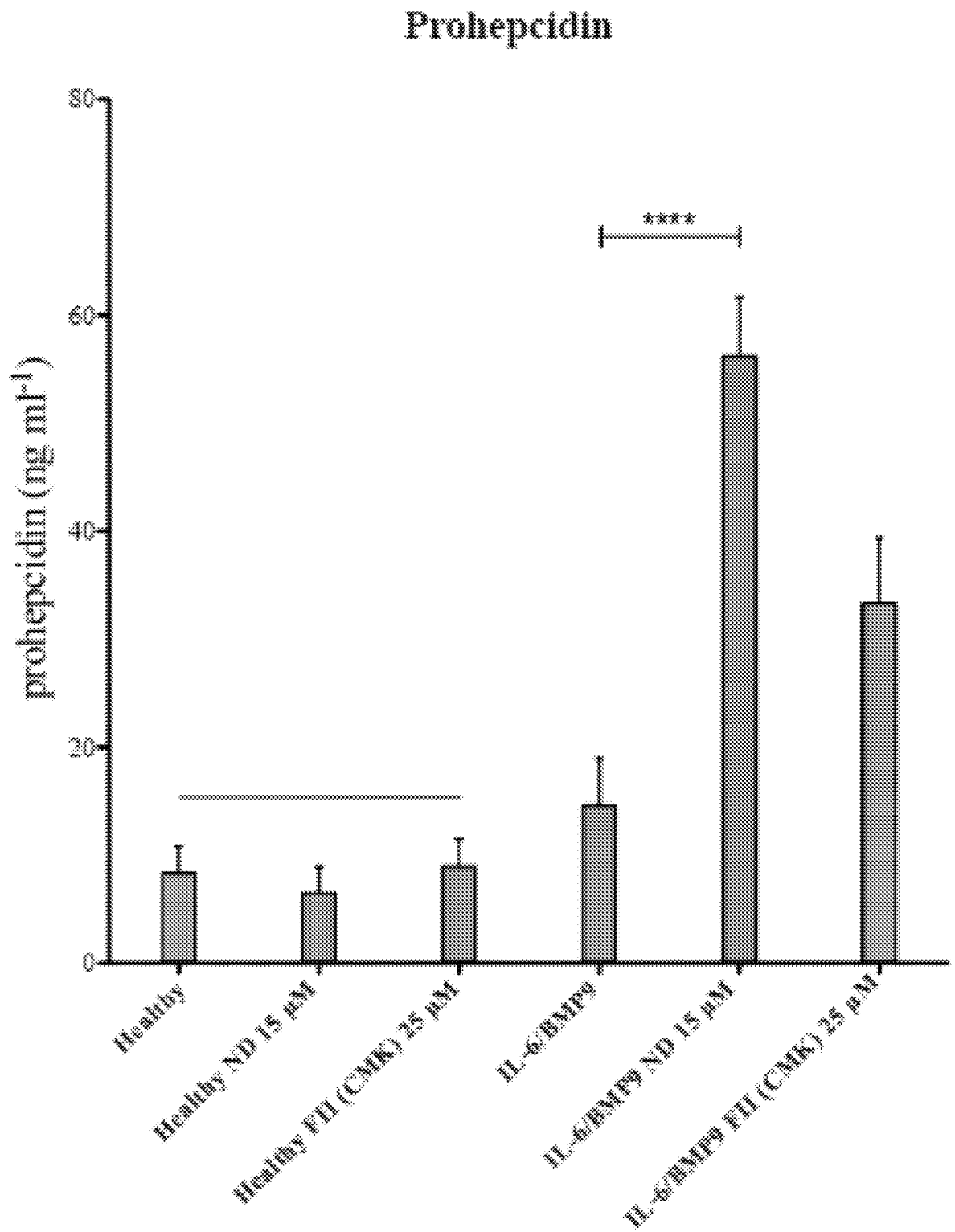

Upon induction of IL-6/BMP-9 to the hepatocytes, prohepcidin levels in media increased from 8.3±4.35 ng/mL to 17.7±7.6 ng/mL (FIG. 26B). Prohepcidin concentrations in IL-6/BMP-9 induced hepatocytes further increased with ND treatment to 56.1±9.7 ng/mL.

Figure 26C:
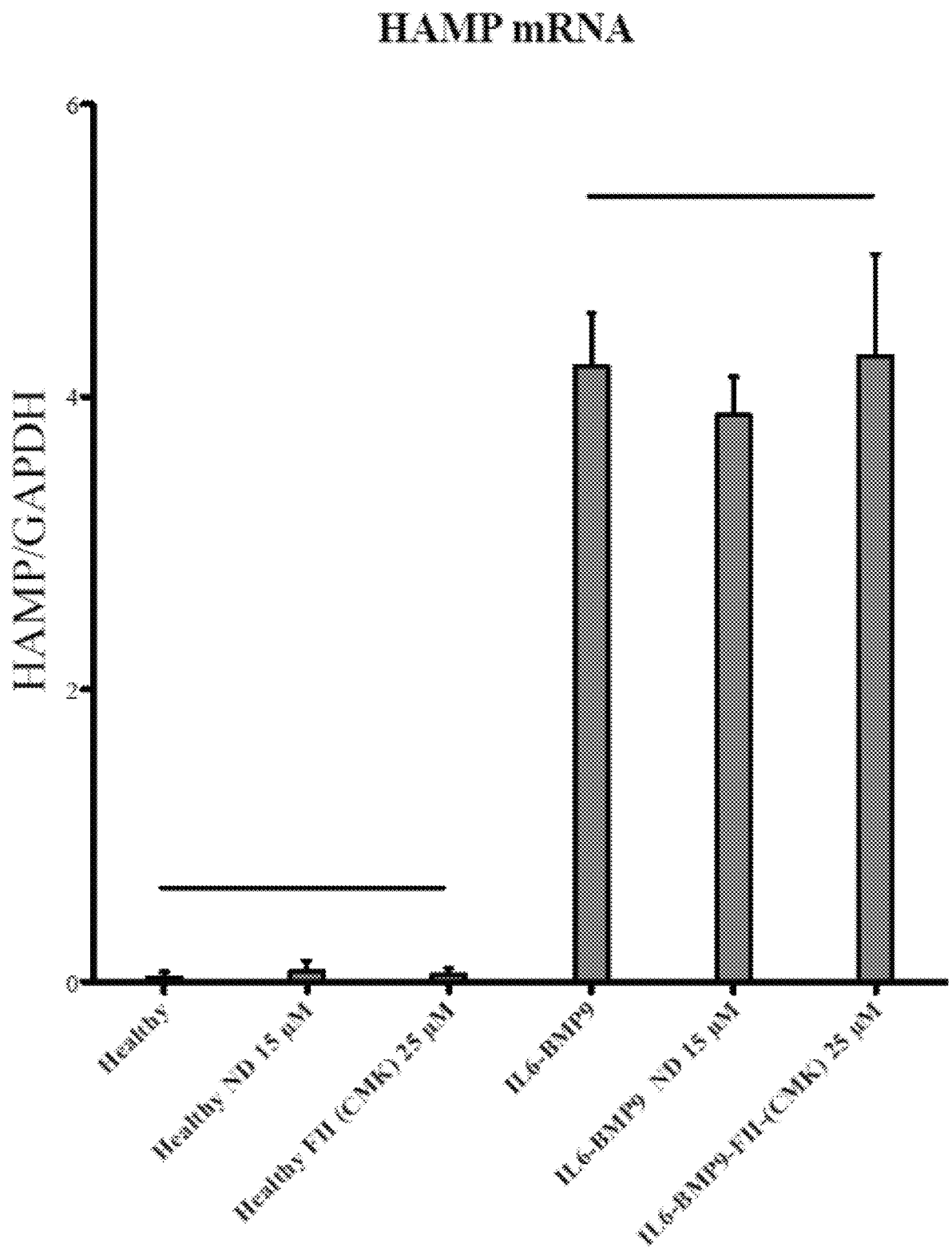

No significant difference in secreted prohepcidin concentration was observed within healthy cell groups with or without treatment of ND or CMK (p>0.05), as mean values ranged from 6.4 to 8.9 ng/mL. Similar results are reported with the HepG2 hepatocyte cell line (FIG. 26C).

Furin is upregulated with varying cancers and sarcomas (Nelfinavir. *DrugBank* (2013). at http://www.drugbank.ca/drugs/DB00220>; Arikawa, E. et al. Cross-platform comparison of SYBR® Green real-time PCR with TaqMan PCR, microarrays and other gene expression measurement technologies evaluated in the Micro Array Quality Control (MAQC) study. BMC Genomics 9, 328 (2008); Jankowska, E. A. et al. Iron deficiency: an ominous sign in patients with systolic chronic heart failure. *Eur. Heart J.* 31, 1872-1880 (2010)). Furin expression has previously been shown to increase in cultured adipocytes when treated with inducers of inflammation (Emans, M. E. et al. Red cell distribution width is associated with physical inactivity and heart failure, independent of established risk factors, inflammation or iron metabolism; the EPIC—Norfolk study, *Int. J. Cardiol.* 168, 3550-3555 (2013)), as well as in HeLa and HepG2 cell lines during iron deficiency and hypoxia (Thomas, G. Furin at the cutting edge: From protein traffic to embryogenesis and disease. *Nat. Rev. Mol. Cell Biol.* 3, 753-766 (2002)).

Figure 27A:
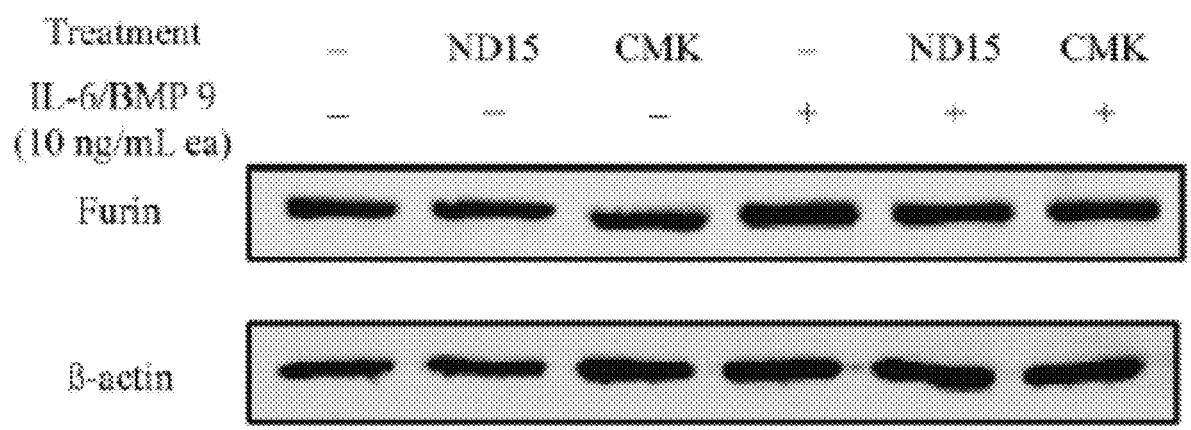
FIGS. 27A-E show that IL-6 and BMP-9 upregulate furin in Huh7 and HepgG2 hepatocytes.
Figure 27B:
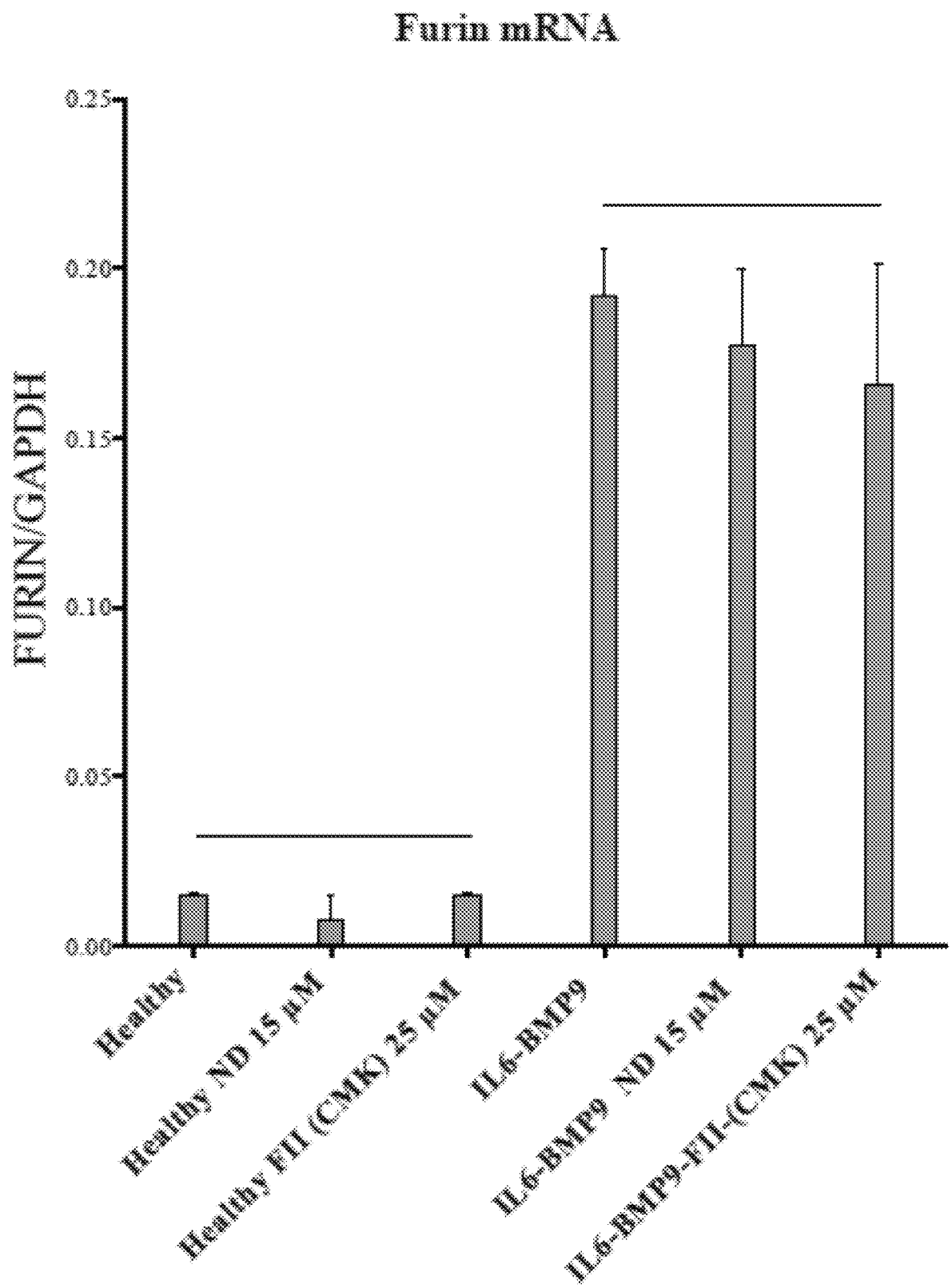
Figure 27C:
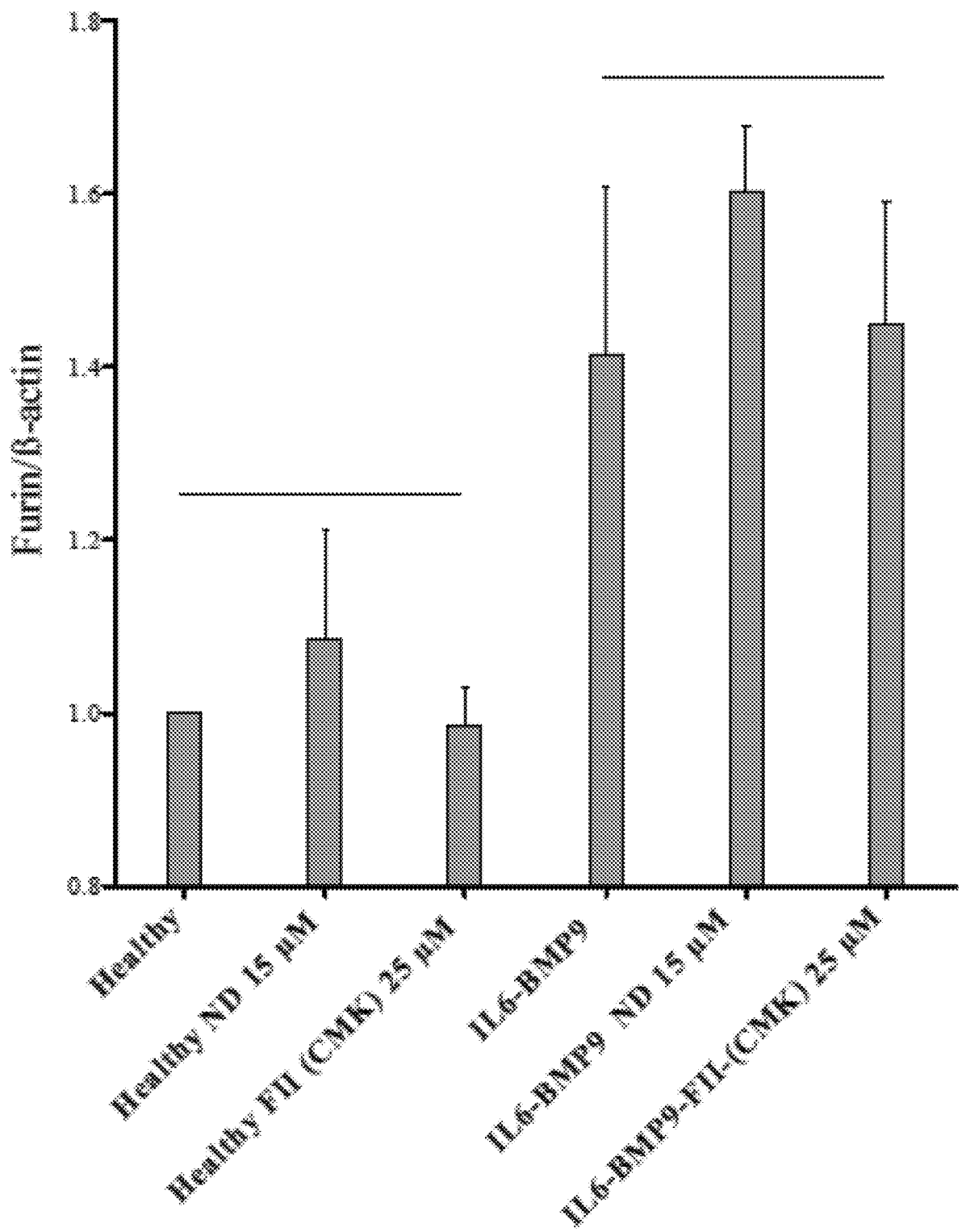
Figure 27D:
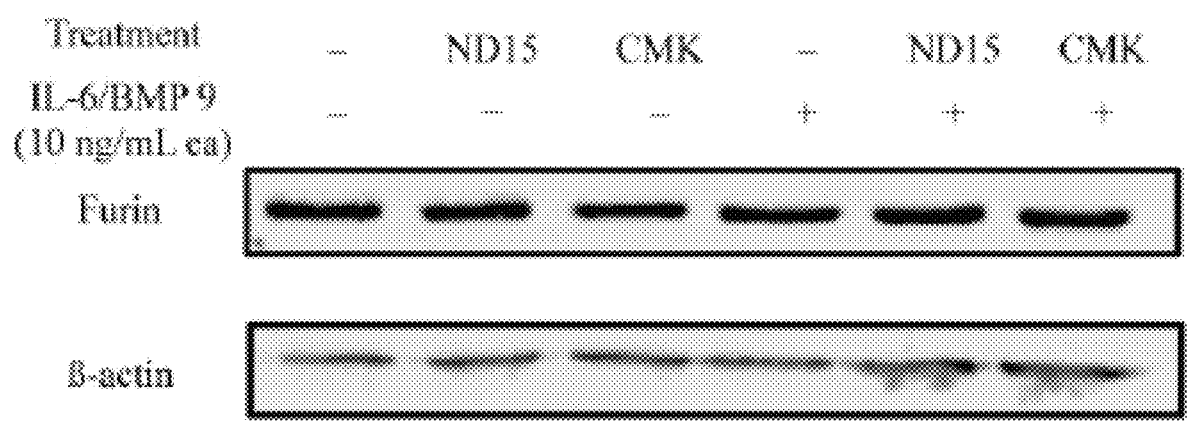
Figure 27E:
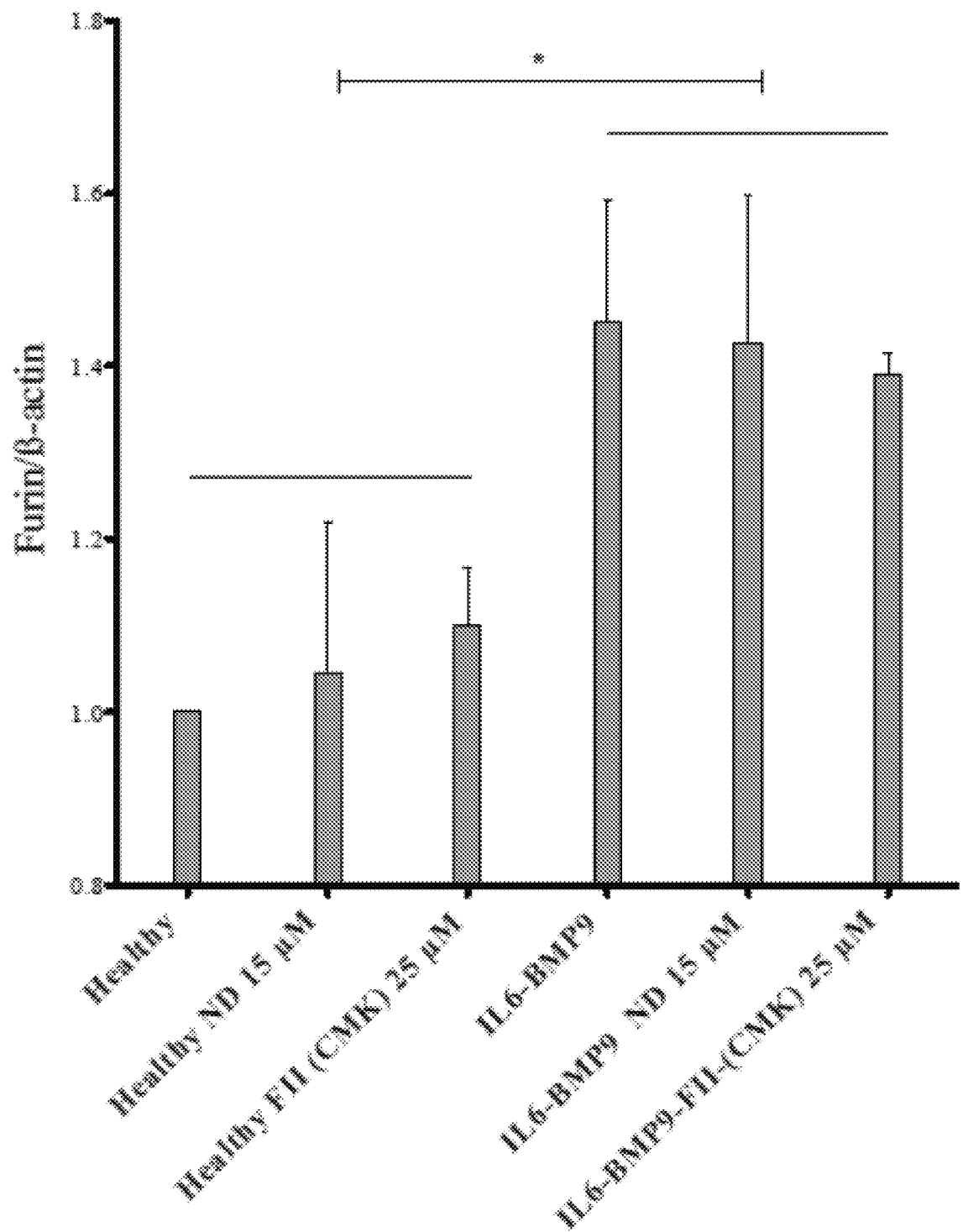

As described herein, the relative furin expression is also significantly increased with induction of IL-6 and BMP-9 inflammatory cytokines (p<0.01) in both Huh7 and HepG2 hepatocyte cell types (FIGS. 27A-E). Co-induction with PIs does not alter or inhibit the gene expression of furin (p>0.05) between healthy and cytokine induced groups (FIG. 27B), Complementary results are seen with furin western blotting (FIGS. 27A and 28C). Levels of Furin protein within both Huh" and HepG2 cell types increase in response to IL-6 and BMP-9 induction. PI treatment has no significant effect on the expression of furin in comparison to controls (p>0.05).

Figure 28A:
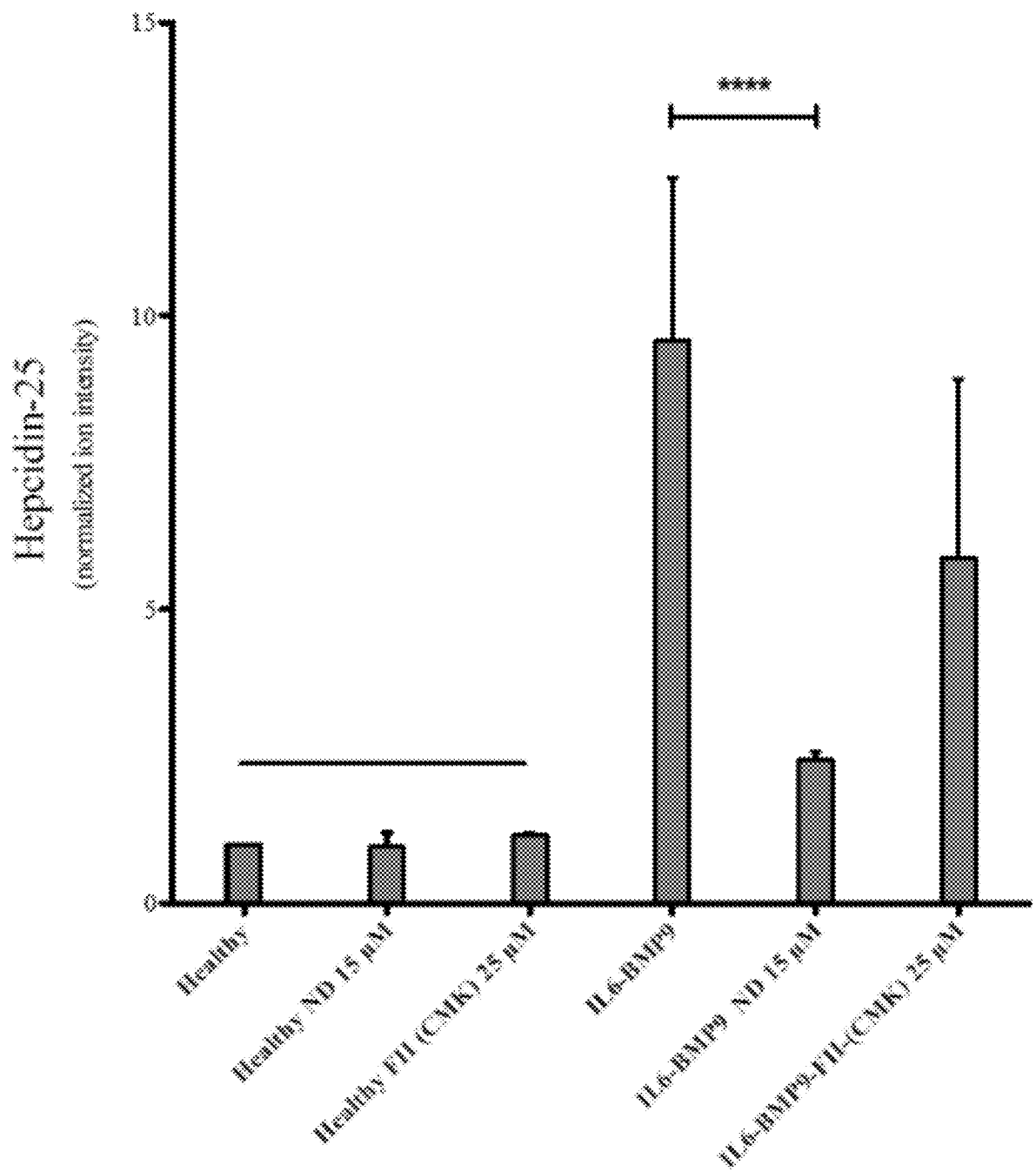
FIGS. 28A-B show that hepcidin production is inhibited with ND treatment in Huh7 and HepG2 hepatocyte cell media.
Figure 28B:
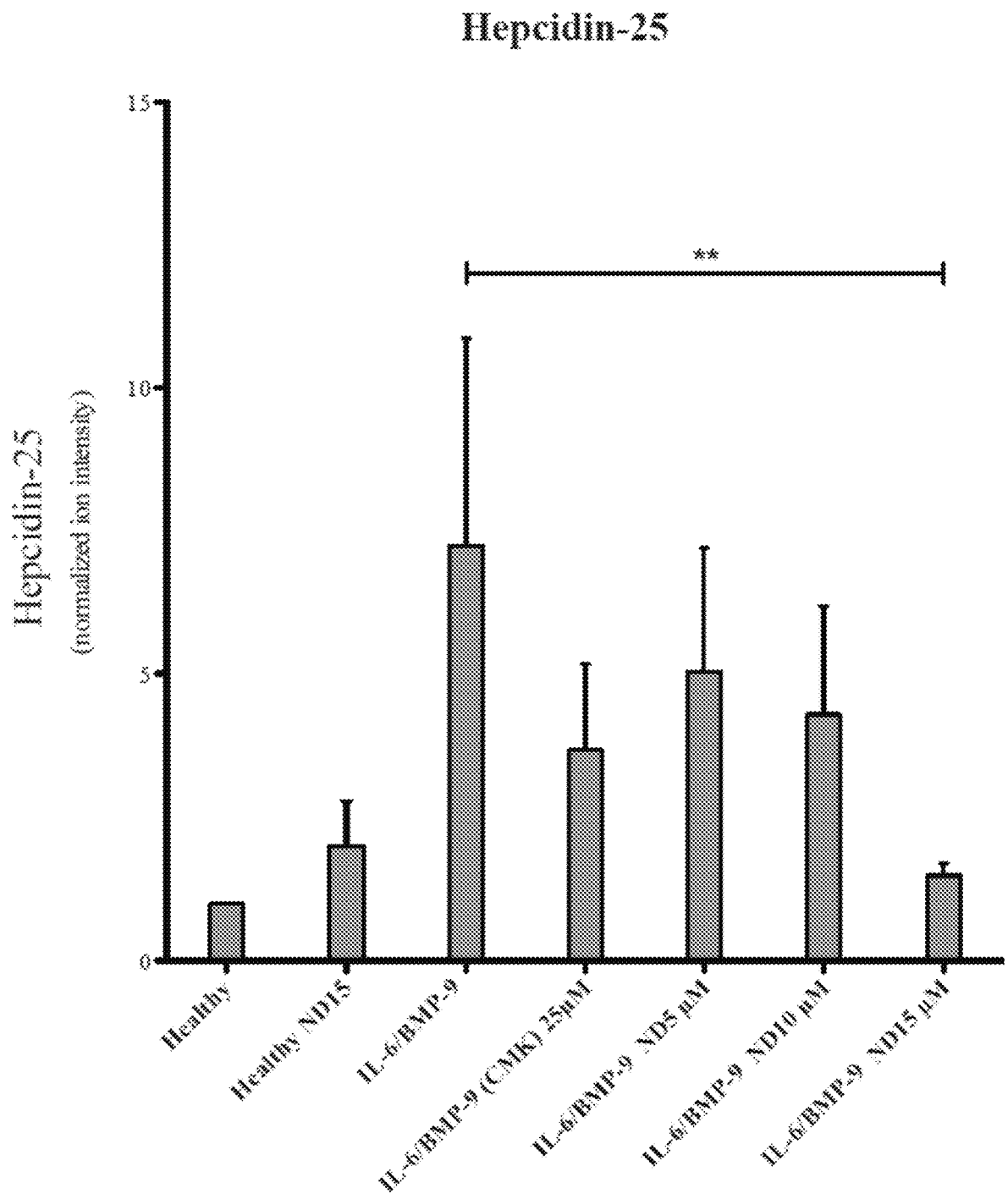

The effect of PIs on formation of mature hepcidin-25 in both Huh7 and HepG2 hepatocytes cell media were quantified using an HPLC-MS/MS method. Data was normalized to hepcidin-25 detected in healthy culture media for each data set. No significant difference is seen between healthy cell groups (p>0.05). As expected, induction with IL-6 and BMP-9 increase hepcidin-25 levels. A relative increase in hepcidin concentration within the media is nearly tenfold (FIG. 28A). When co-treated with ND, mean normalized hepcidin levels drop nearly 75% as compared to the cytokine-induced cell media. A statistically significant drop in mature hepcidin-25 is not observed with the PI CMK (p>0.05) in these data, however, a strong tendency of inhibition appears to be taking place. Similar effects were also observed with the HepG2 hepatocyte cell tissue media (FIG. 28B) with ND co-treatment. In FIG. 28B, hepcidin is shown to decrease in a dose-dependent manner, (5, 10, 15 μM) where significance occurs with ND at 15 μM (p<0.01).

Increased production of hepcidin leads to reduced expression of ferroportin, as hepcidin binds to ferroportin and consequently induces endocytosis. As described herein, cytokine-induced hepcidin production is inhibited with inhibition of furin, allowing unimpeded ferroportin activity.

Figure 29A:
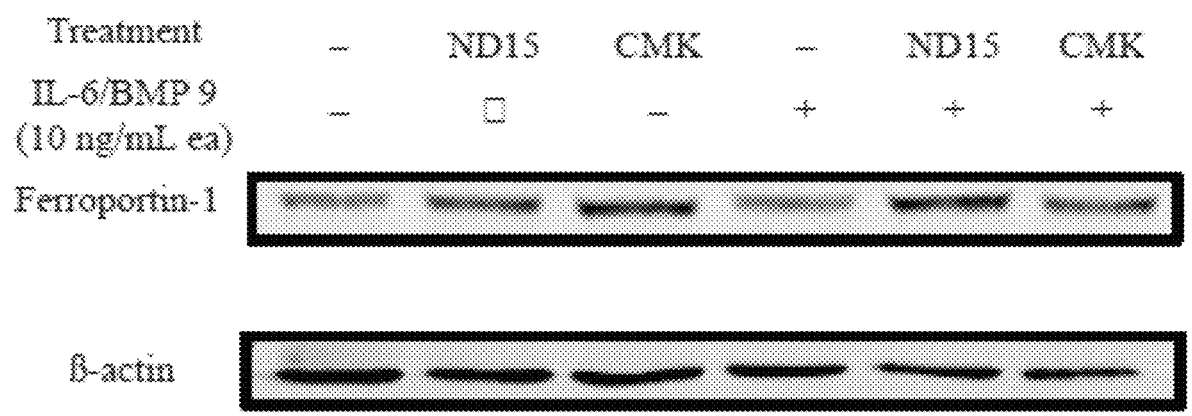
FIGS. 29A-D show the prevention of ferroportin degradation.
Figure 29B:
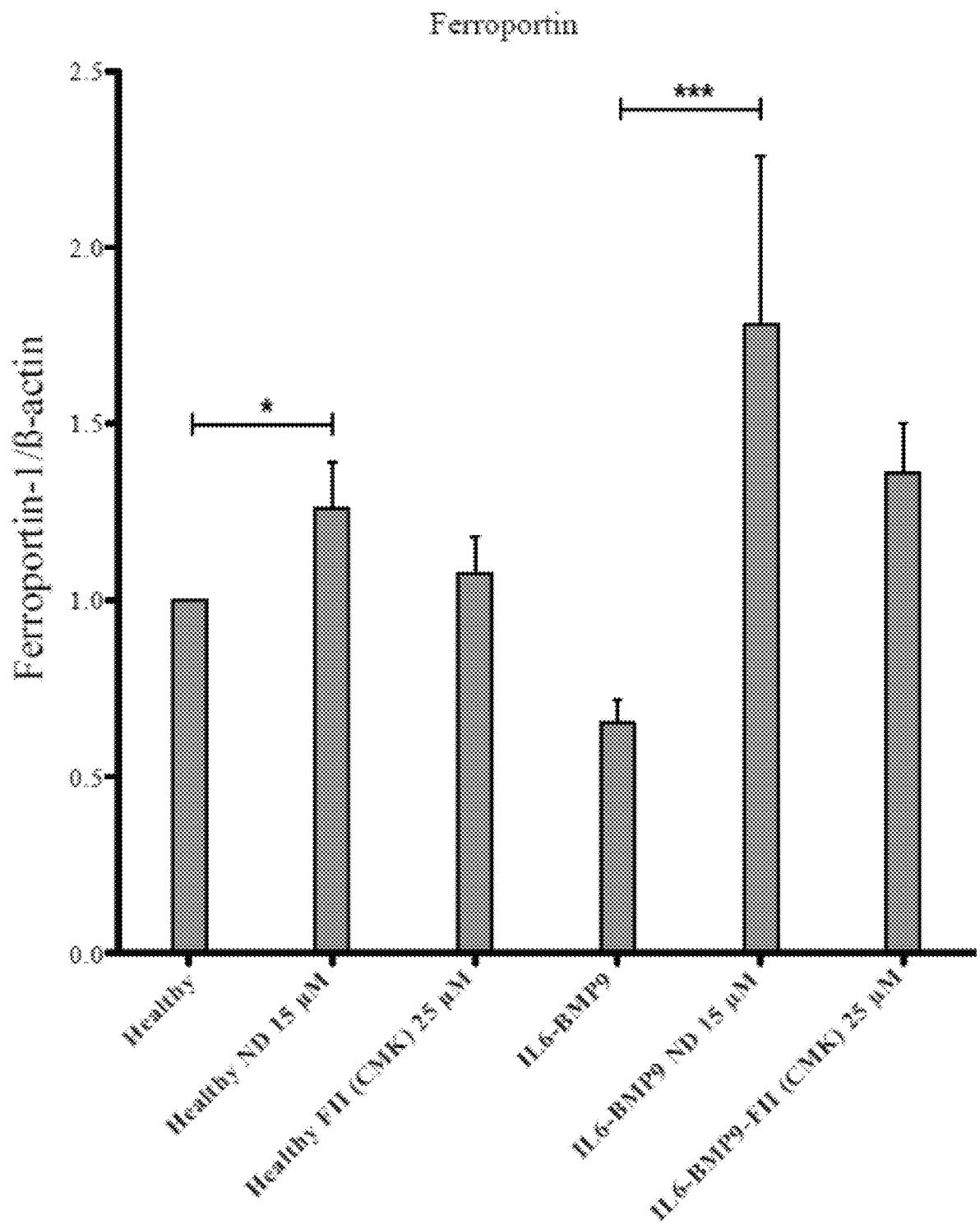
Figure 29C:
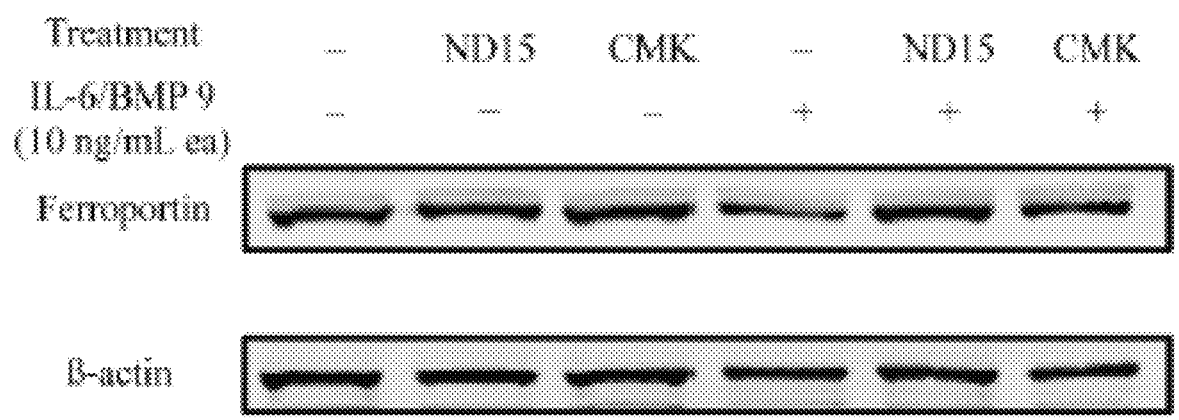
Figure 29D:
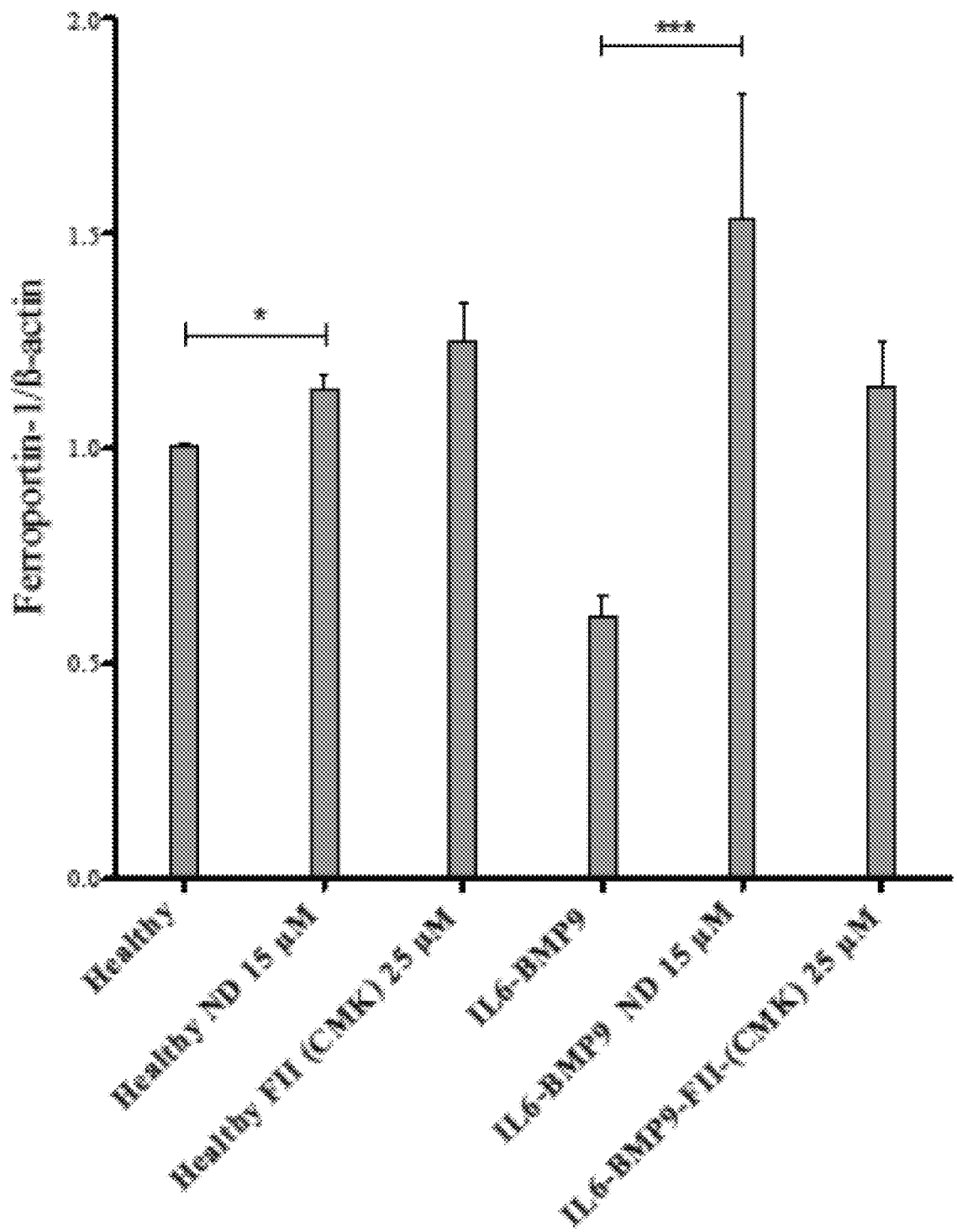

Ferroportin expression is increased significantly relative to control (p<0.001) with co-treatment of the PI combination ND at 15 μM in Huh7 hepatocytes (FIGS. 29A-D). As expected, relative ferroportin expression is decreased in IL-6/BMP-9 cells without PI treatment, as mature hepcidin is produced without hindrance. Ferroportin expression is significantly increased within healthy ND treated cell cultures (p<0.05) (FIGS. 29A and 29B). Additionally, these results are observed in the HepG2 hepatocyte cell line (FIGS. 29C and 29D).

This example shoves the ability of nelfinavir (7.5 μM) and darunavir (7.5 μM) to inhibit furin, and thereby impede cleavage of prohepcidin into its mature bioactive form.

Example 5

Inhibition of Furin to Restore Iron Redistribution in Animals

The following example demonstrates that the protease furin is an effective drug target for the prevention or amelioration of ACI As demonstrated in Examples 1 and 2, molecular modeling analysis and in vitro furin assays show that the protease inhibitor nelfinavir binds to and inhibits furin. This example verifies that nelfinavir inhibits furin in animal subjects. Furin inhibition prevents hepcidin activation, prevents ferroportin degradation, and allows normal iron delivery to the bloodstream and bone marrow.

An animal model of rheumatoid arthritis to induce anemia of chronic inflammation was used. Group A Streptococcal Peptidoglycan-Polysaccharide (PG-LPS) injection causes chronic activation of the immune system, increased production of cytokines, increased levels of hepcidin, and sustained anemia.

Figure 33A:
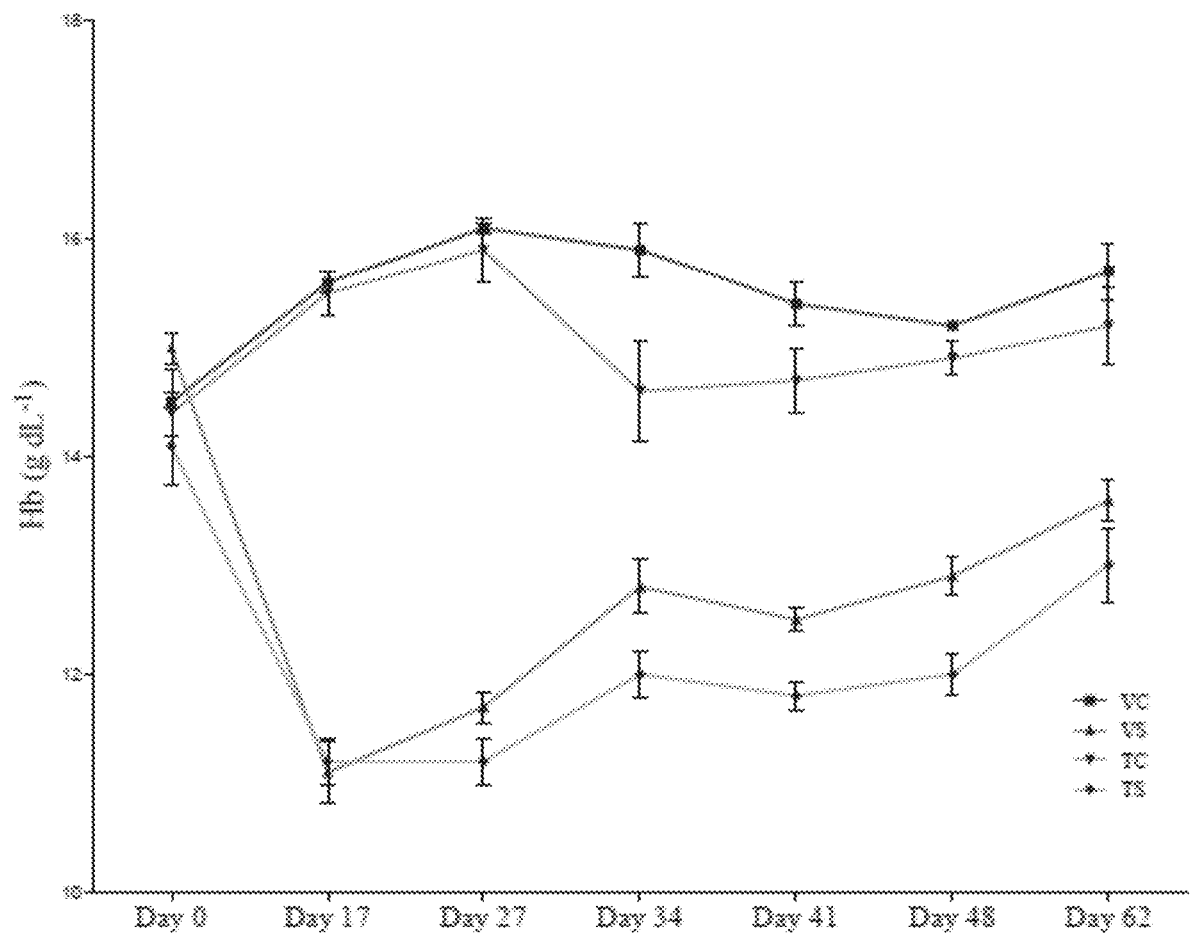
FIGS. 33A-B graphically depict hemoglobin and hematocrit time course. Complete blood counts (CBCs) for hemoglobin (FIG. 33A) and hematocrit (FIG. 33B) over the course of the study, VC=vehicle control; VS=vehicle PG-LPS; TC=treated control, and TS=Treated PG-LPS.
Figure 33B:
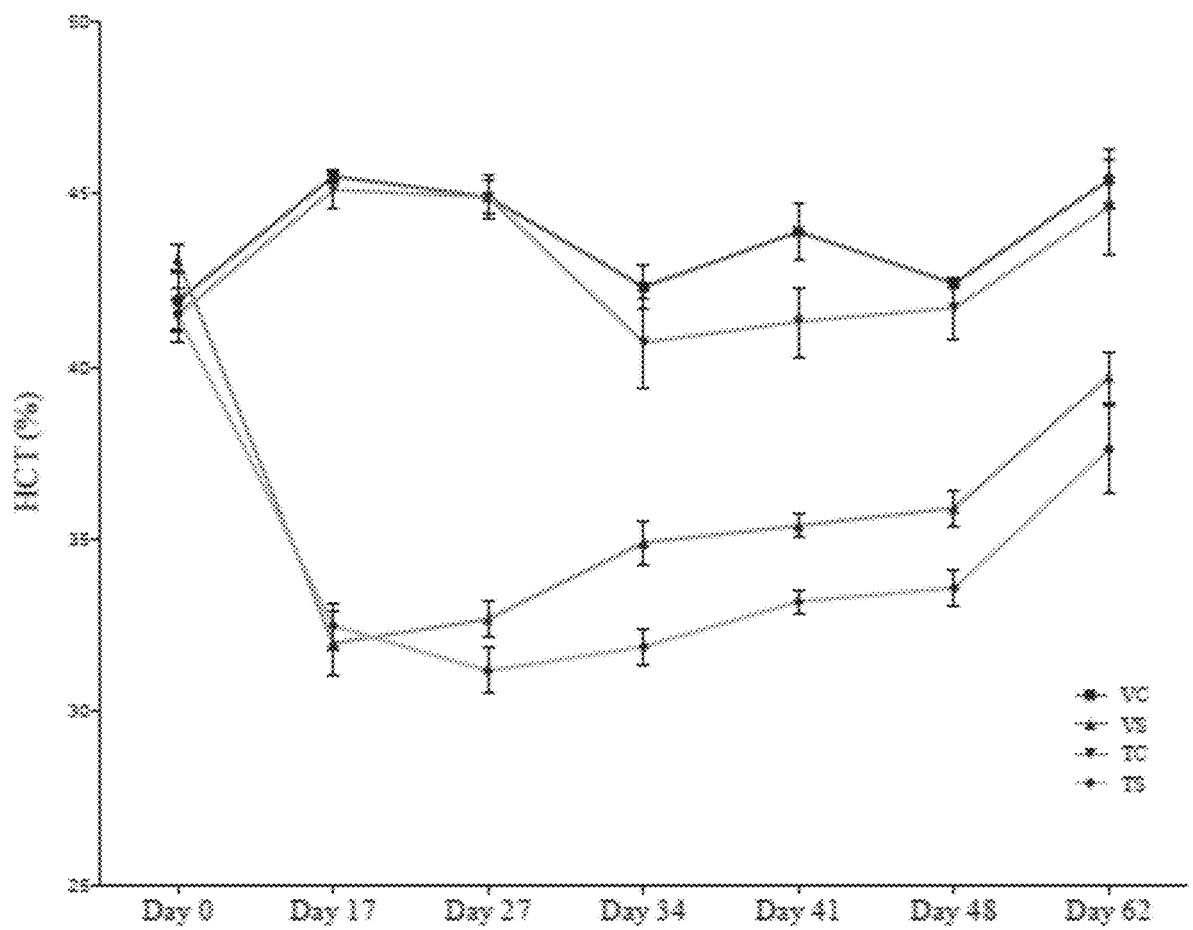
Figure 35:
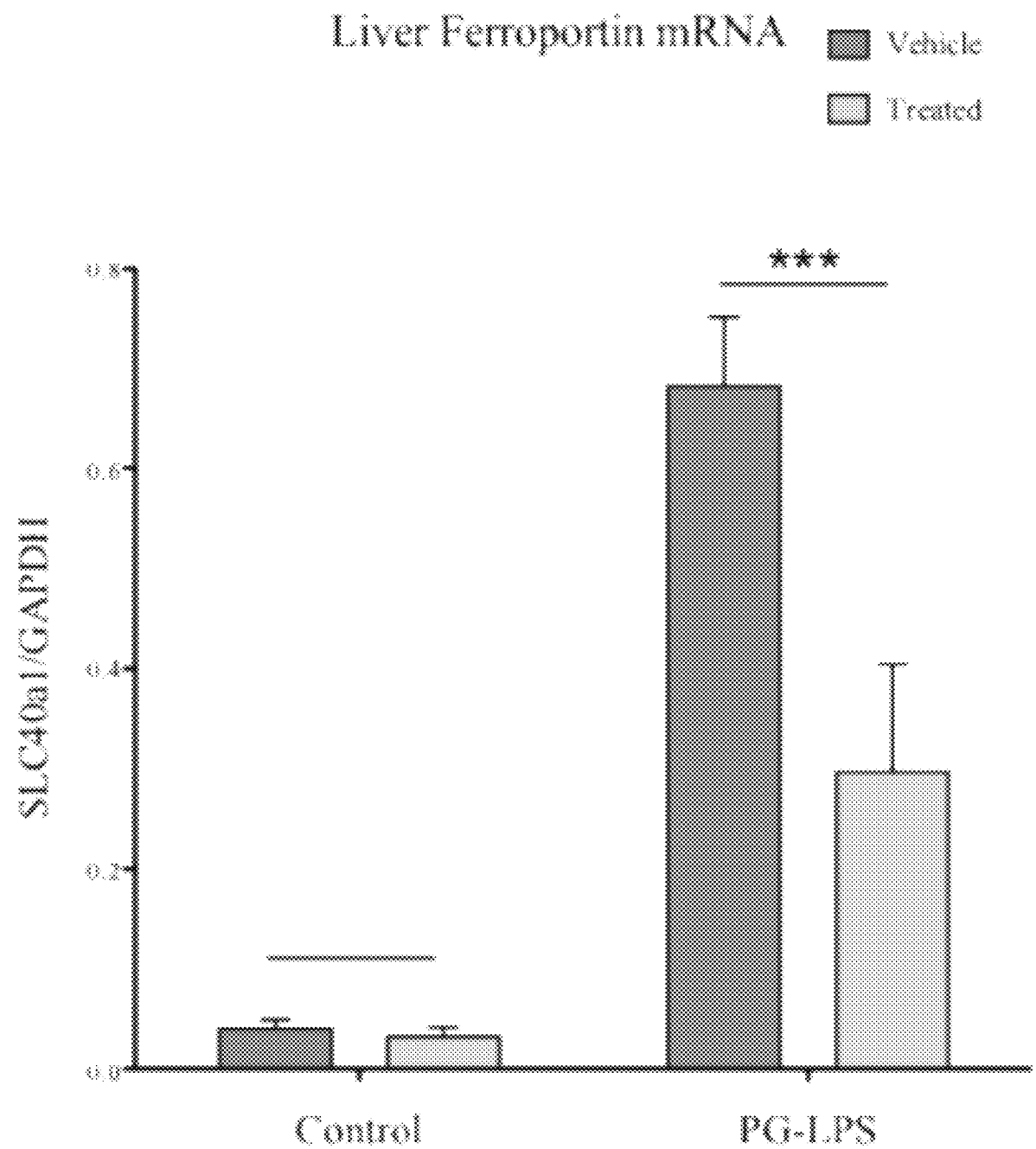
FIG. 35 shows liver ferroportin mRNA (S1c40a).

As described below, at a therapeutic serum concentration, nelfinavir (4 ng/mL) inhibited mature hepcidin production by 47% while increasing prohepcidin 148%. Ferroportin expression increased 2.5 fold in animal liver, while iron in serum and bone marrow increased significantly (p<0.01 and p<0.05 respectively). However, anemia persisted, as hemoglobin and hematocrit did not significantly recover (FIGS. 33A-B). Nelfinavir treatment successfully inhibited hepcidin production and increased liver ferroportin allowing for restoration of iron in the serum and bone marrow (FIG. 35).

Figure 30A:
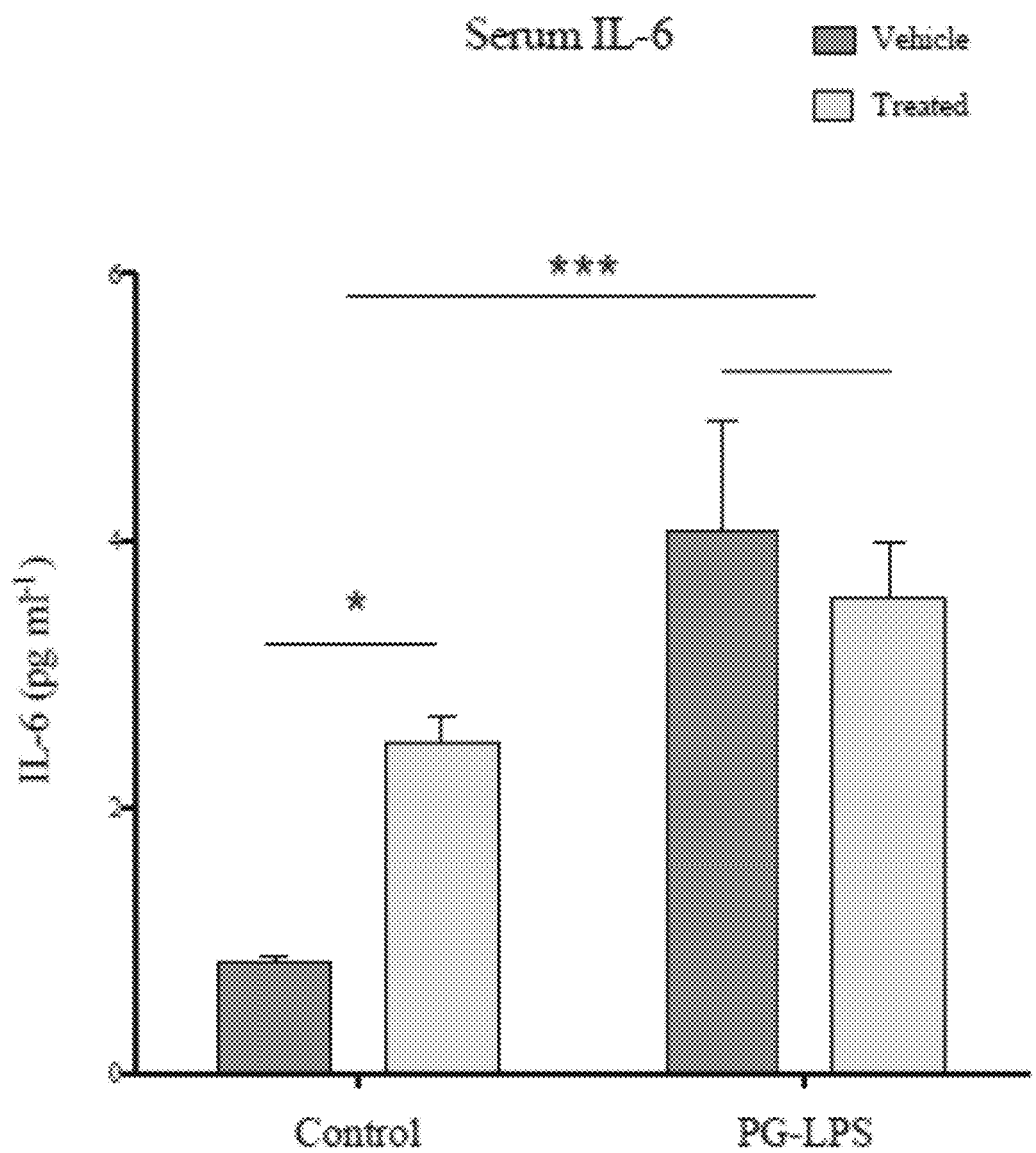
FIGS. 30A-C show' the cytokine and hormone levels present in serum 6 weeks post Streptococcal Peptidoglycan-Polysaccharide (PG-LPS) induction.
Figure 30B:
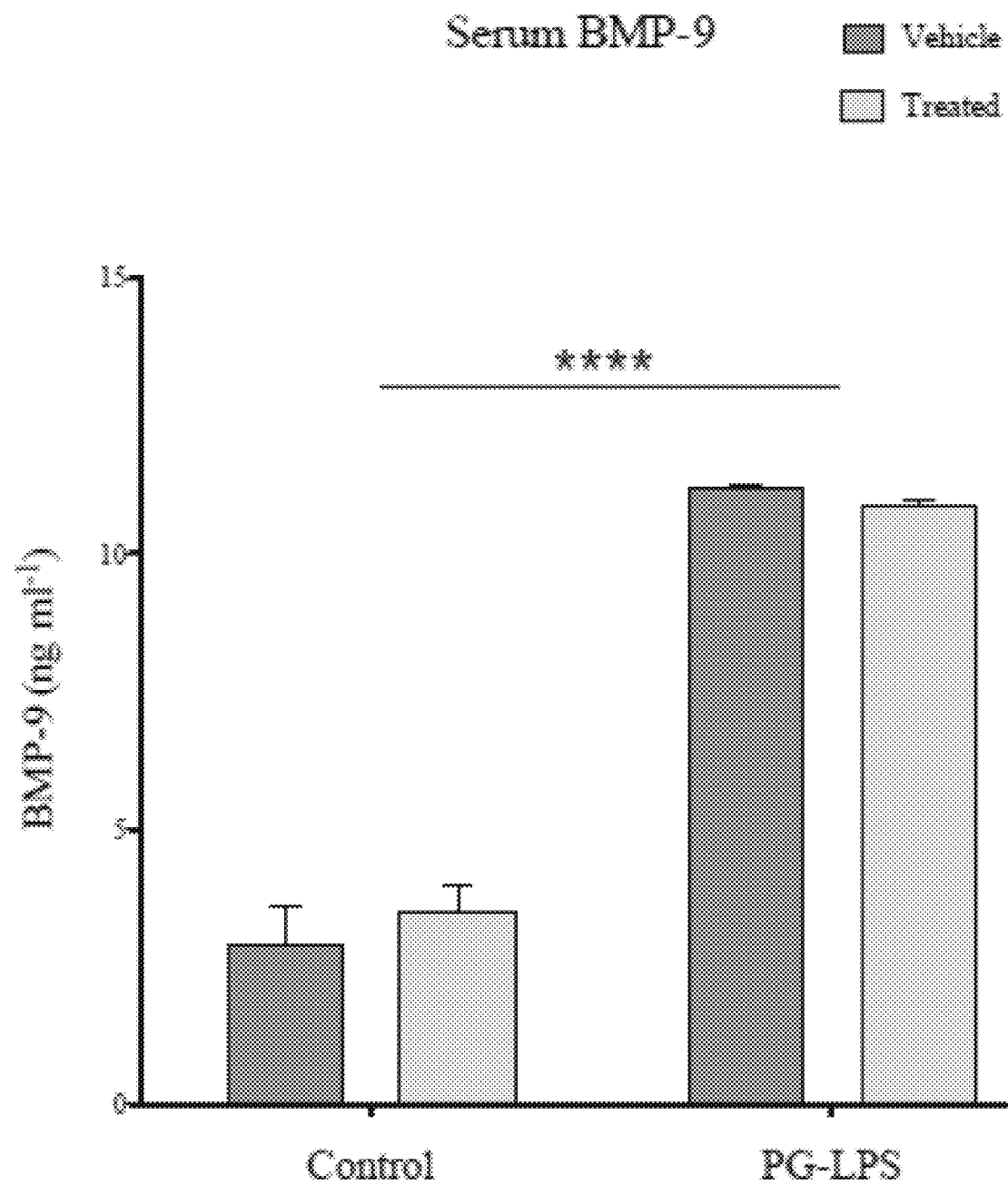

Chronic inflammation was induced in vivo using a well-established rat model of ACI Streptococcal Peptidoglycan-Polysaccharide (PG-LPS) injections resulting in a chronic inflammatory state where anemia is sustained for many weeks (Kurowski, M., Kaeser, B., Sawyer, A., Popescu, M. & Mrozikiewicz, A. Low-dose ritonavir moderately enhances nelfinavir exposure. *Clin. Pharmacol Ther.* 72, 123-132 (2002)). Inflammatory cytokines known to induce HAMP gene expression, interleukin-6 (IL-6) and bone morphogenic protein-9 (BMP-9), were significantly elevated in the serum of PG-LPS treated animals (FIGS. 30A and 30B). Additionally, serum erythropoietin (EPO) showed no statistically significant differences between groups, consistent with other studies of ACI (FIG. 30C) (Thomas, C. & Thomas, L. Anemia of Chronic Disease: Pathophysiology and Laboratory Diagnosis. *Lab. Hematol.* 11, 14-23 (2005)).

The inflammatory cytokines IL-6 and BMP-9, which were present in the serum of PG-LPS treated animals (FIGS. 30A and 30B) are known to activate transcription of the HAMP gene and the expression of hepcidin through STATS and SMAD pathways respectively. Protease inhibitors block the proteolytic cleavage of prohepcidin to form hepcidin by inhibiting furin, and therefore, there is no inhibition of HAMP mRNA production.

Quantitative PCR (qPCR) of liver tissue was used to compare the expression of the HAMP gene between groups. HAMP expression remained low in the absence of chronic inflammation caused by PG-LPS treatment (FIG. 31A), but PG-LPS treatment caused an approximate 6-fold increase in HAMP gene expression. Additionally, in PG-LPS treated animals, nelfinavir did not show any statistically significant changes in the transcription of HAMP mRNA indicating these drugs do not inhibit HAMP mRNA transcription.

Figure 31A:
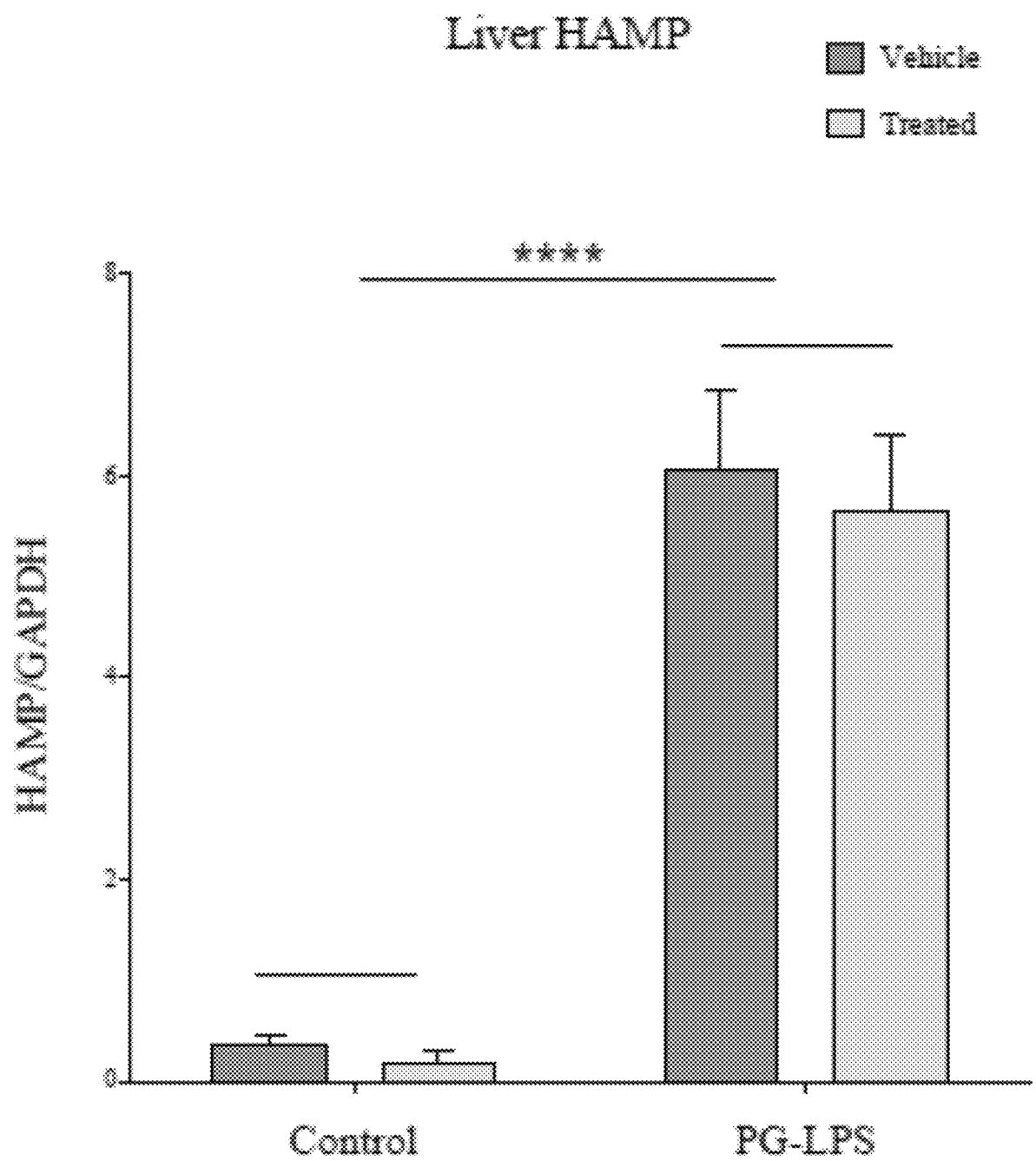
FIGS. 31A-E show that PIs block hepcidin secretion.
Figure 31B:
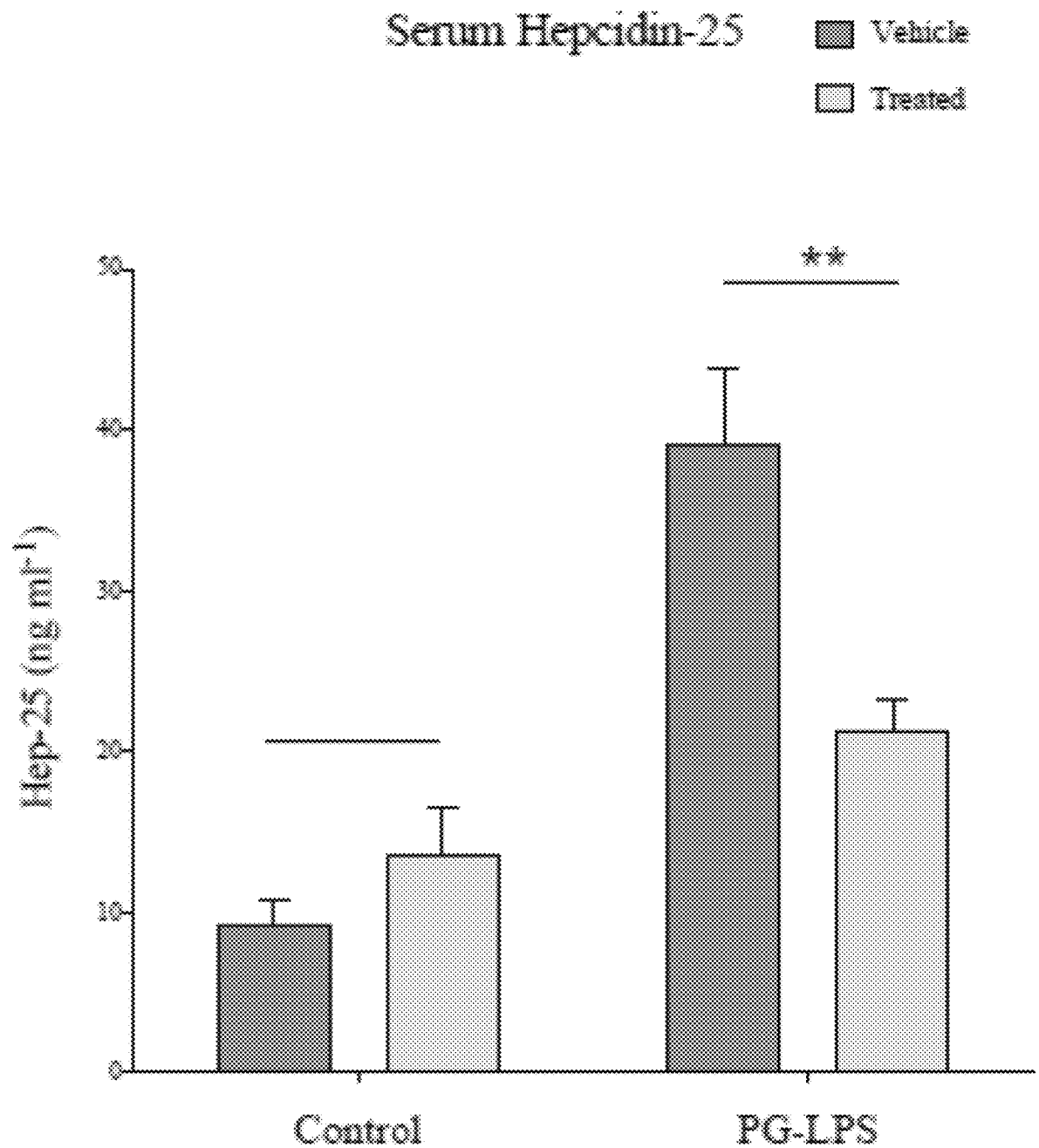
Figure 31C:
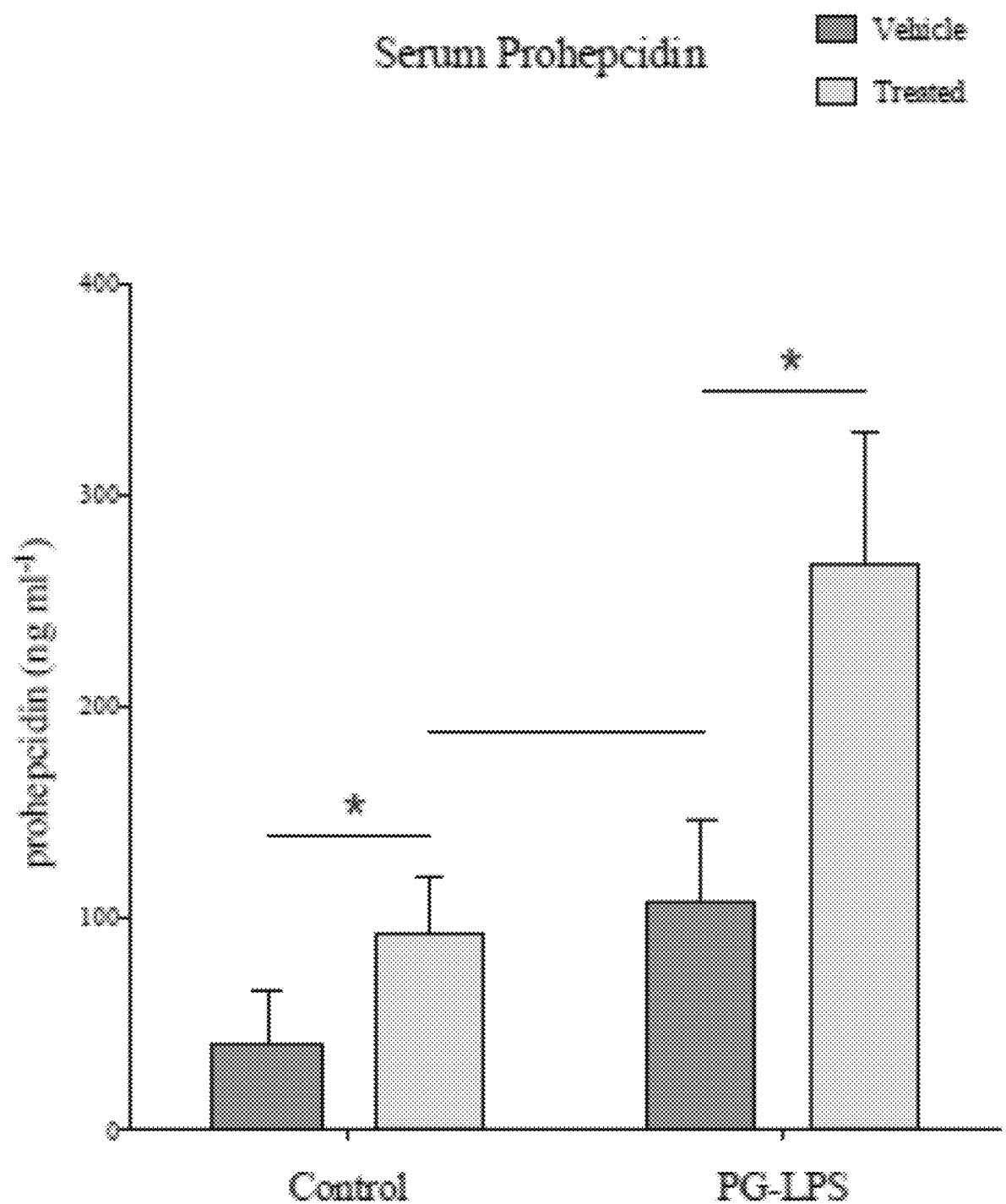
Figure 31D:
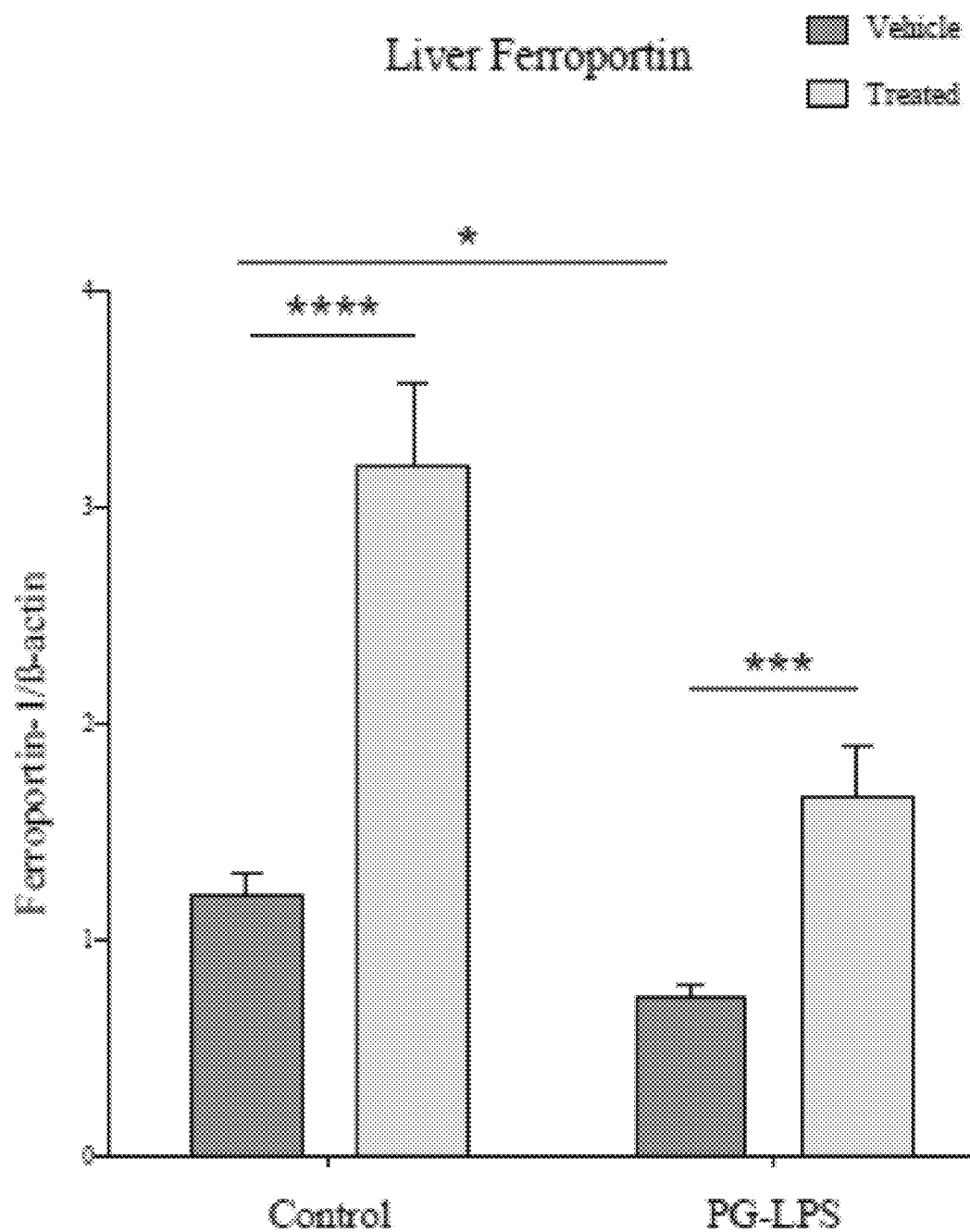
Figure 31E:
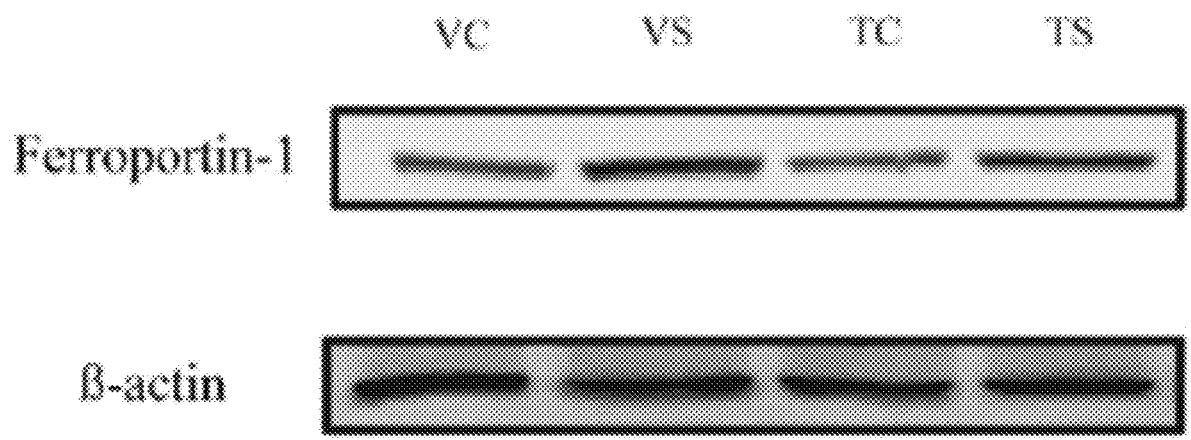

As expected by the elevated HAMP mRNA levels in PG-LPS treated rats, the serum hepcidin levels increased in PG-LPS treated rats (FIG. 31B). However, the serum hepcidin levels in PG-LPS and nelfinavir treated rats are approximately 2-fold lower than in PG-LPS rats indicating that nelfinavir inhibited furin from processing prohepcidin to hepcidin (FIG. 31B). In addition, FIG. 31C shows that serum prohepcidin is approximately 2.5-fold higher in PG-LPS treated rats treated with nelfinavir. Western blot analysis of ferroportin from liver tissue shows that ferroportin is significantly higher in PG-LPS treated rats receiving nelfinavir than PG-LPS treated rats without nelfinavir. These ferroportin results further confirm that lower serum hepcidin levels occur in nelfinavir treated rats, as hepcidin is known to bind and subsequently induce endocytosis and degradation of ferroportin (FIGS. 31D and 31E).

Nelfinavir treatment restores iron redistribution into serum and tissue. The treatment of PG-LPS treated rats with nelfinavir decreased serum hepcidin levels (FIG. 31B) and increased ferroportin levels (FIG. 31C), The increased level of ferroportin allows the restoration of normal iron export from iron rich tissue and increase the iron content in the serum and bone marrow.

These results in inflamed rats show that treatment with protease inhibitors, including, for example, nelfinavir combined with darunavir and/or ritonavir, were effective at inhibiting furin from cutting prohepcidin into hepcidin (FIGS. 31B and 31C). This dropped serum levels of hepcidin and increased ferroportin on the surface of liver cells (FIG. 31D). The lower levels of serum hepcidin and increased levels of liver ferroportin resulting in increased iron release from the liver (FIG. 32B), elevated serum iron levels (FIG.

Figure 30C:
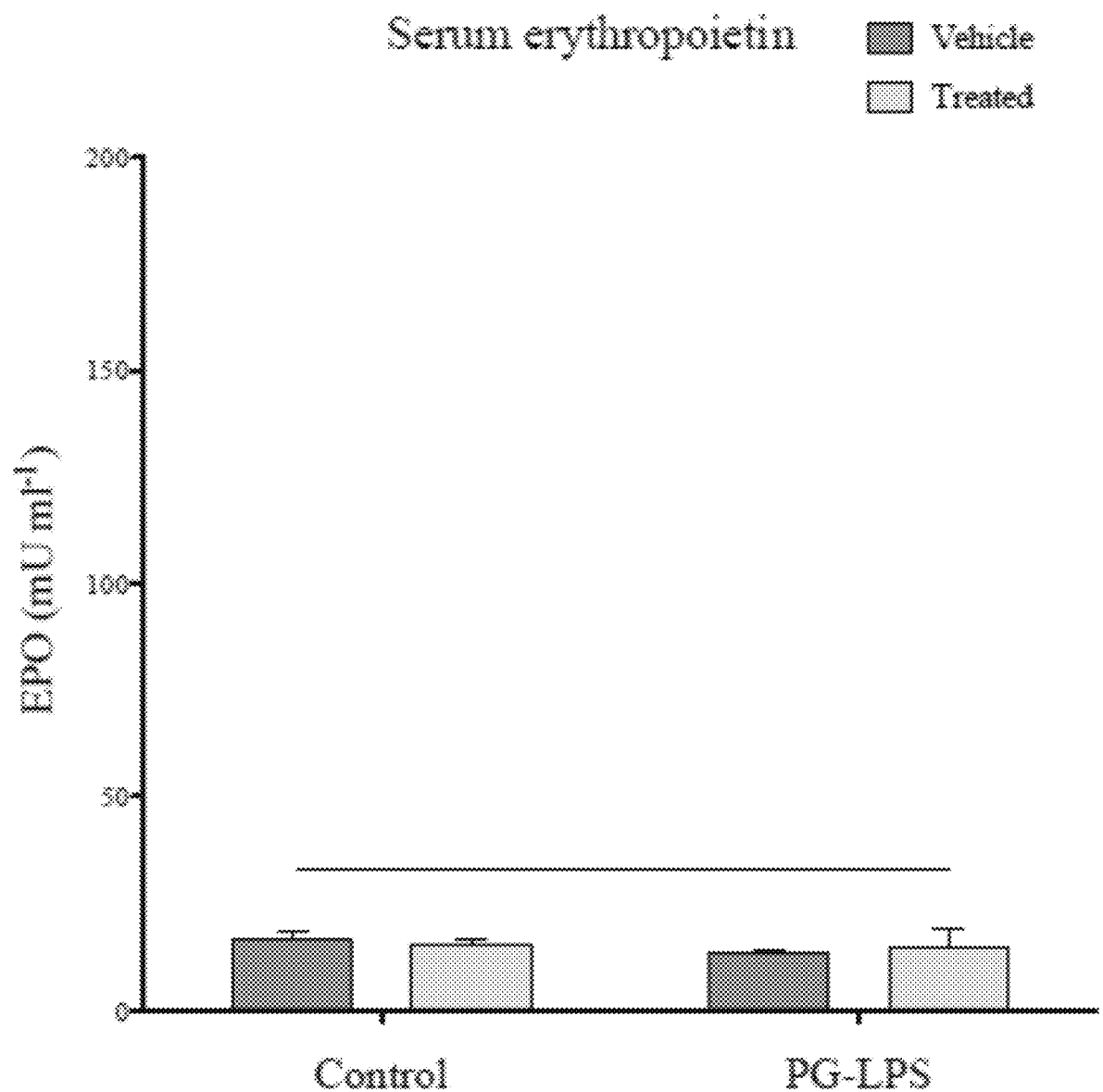

32A) and increased iron in the bone marrow (FIG. 32C), even with inflammation markers IL-6 and BMP-9 at high levels (FIGS. 30A and 30B). It was discovered that erythropoietin levels were low due to elevated BMP-9 levels (FIG. 30C).

Amgen performed a similar study (Blood, (2010) 115, (17) 3616-3624) with inflamed mice using an anti-hepcidin antibody to deplete serum of hepcidin. Their anti-hepcidin antibody treatment resulted in enhanced liver iron release, elevated serum iron and elevated bone marrow iron. Similar to the results shown herein, the elevated inflammatory biomarkers caused low EPO levels. Combining EPO treatment with their anti-hepcidin antibody restored hemoglobin and hematocrit levels in mice. This study is hereby incorporated by reference in its entirety.

Treating patients with chronic inflammation with EPO drugs alone is insufficient to restore hematocrit and hemoglobin levels due to the lack of iron in the bone marrow during inflammation. Based on these results, the co-administration or combination drug treatment that includes HIV protease inhibitors such as nelfinavir and darunavir and/or ritonavir co-injected with EPO allows nelfinavir and darunavir and/or ritonavir to restore iron redistribution from the liver to the bone marrow followed by stimulation of red blood cell synthesis by EPO. The co-administration of nelfinavir and darunavir and/or ritonavir with EPO treatment enhances the effectiveness of EPO for the treatment of anemia of chronic inflammation.

Some embodiments provided herein relate to the treatment of anemia in subjects suffering from cancer. Subjects suffering from cancer undergo treatments, including, for example chemotherapy. In some embodiments, chemotherapy causes anemia of chronic inflammation. In some embodiments, the inflammation caused by chemotherapy is so severe that EPO treatment is often ineffective and the patients require blood transfusions. In some embodiments, the co-administration of a chemotherapy drug combined with EPO and the HIV protease inhibitors nelfinavir and darunavir and/or ritonavir are used to treat the cancer and the anemia associated with the chemotherapy drug.

Figure 32A:
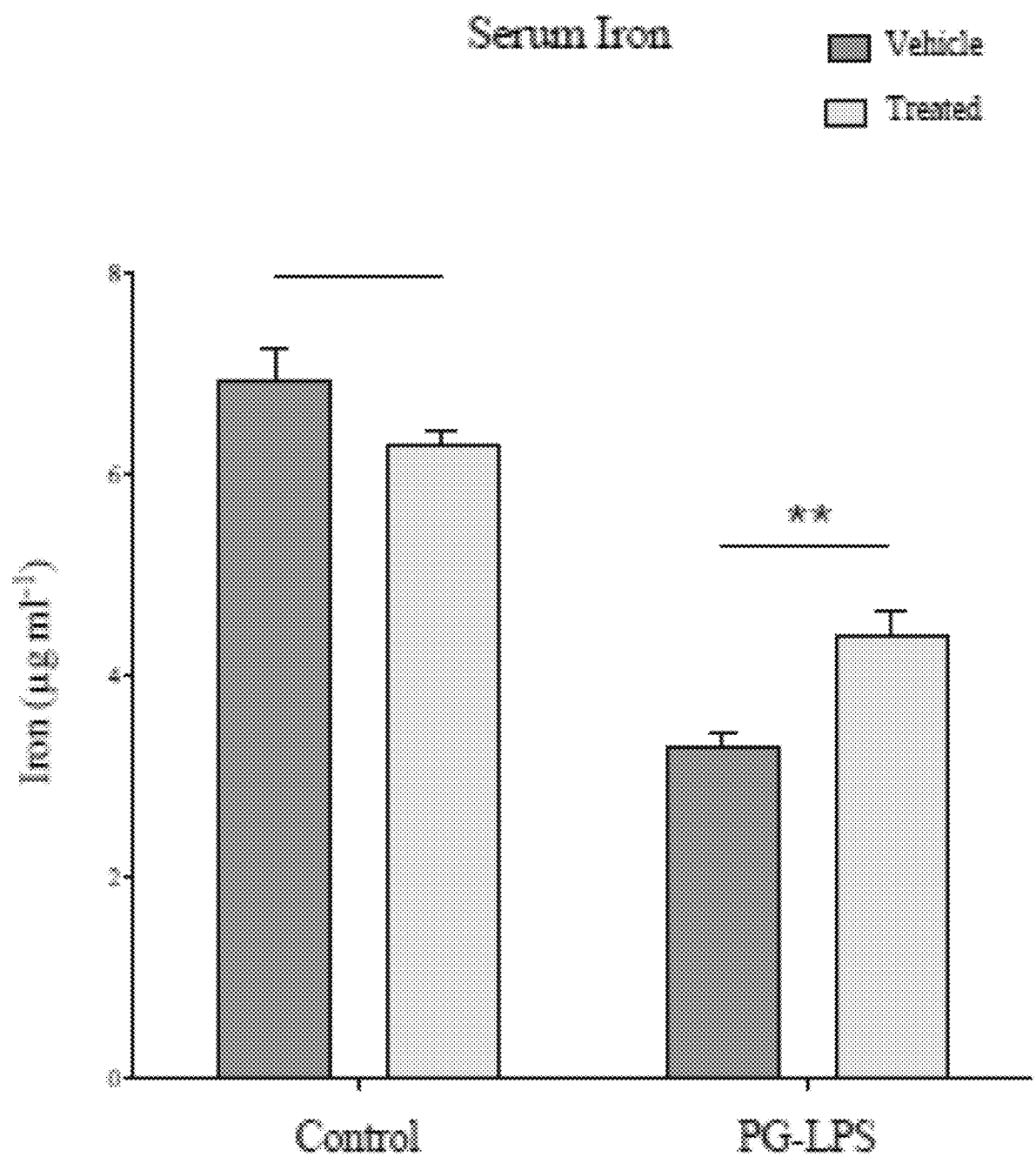
FIGS. 32A-C show iron analysis between healthy rats and rats treated with nelfinavir.
Figure 32B:
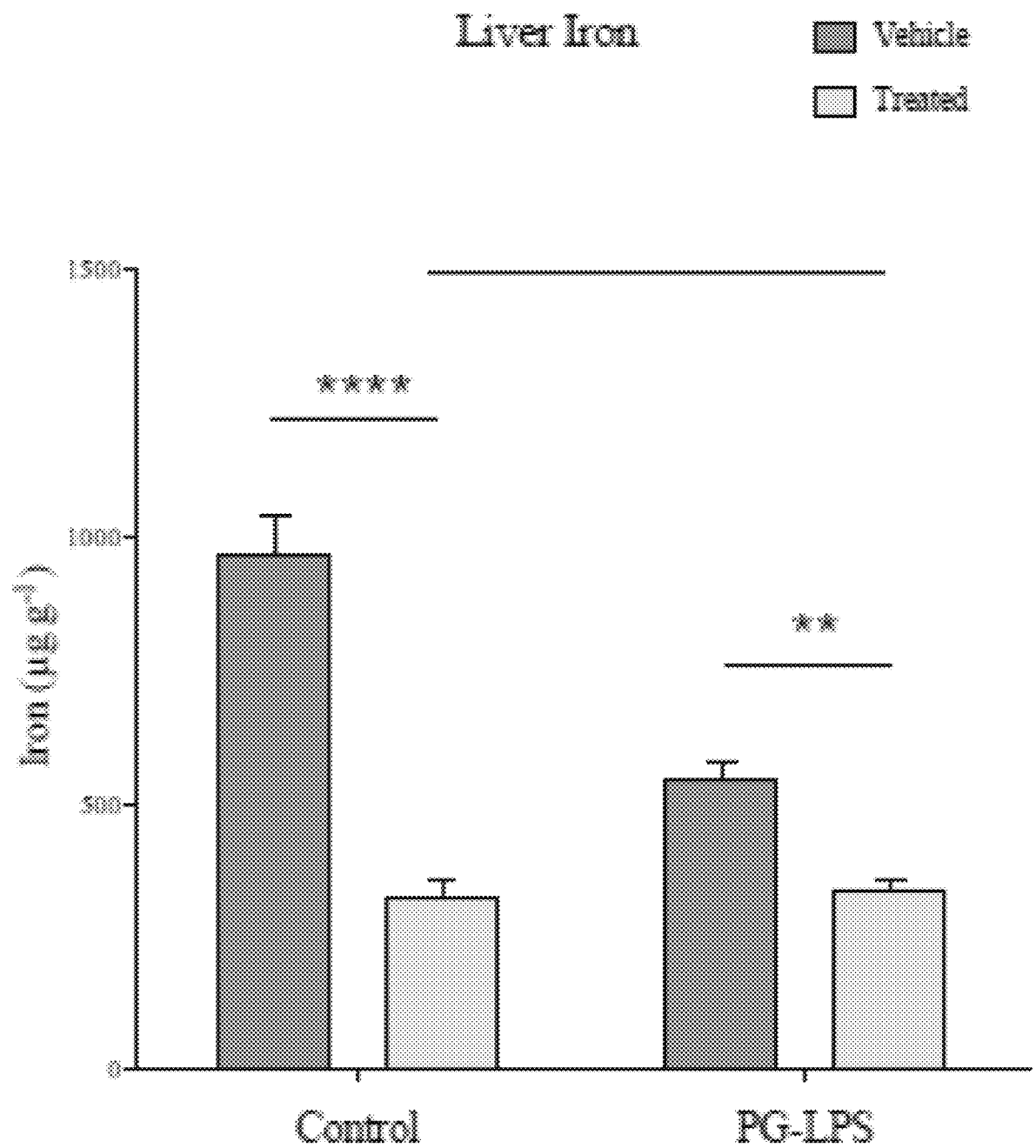
Figure 32C:
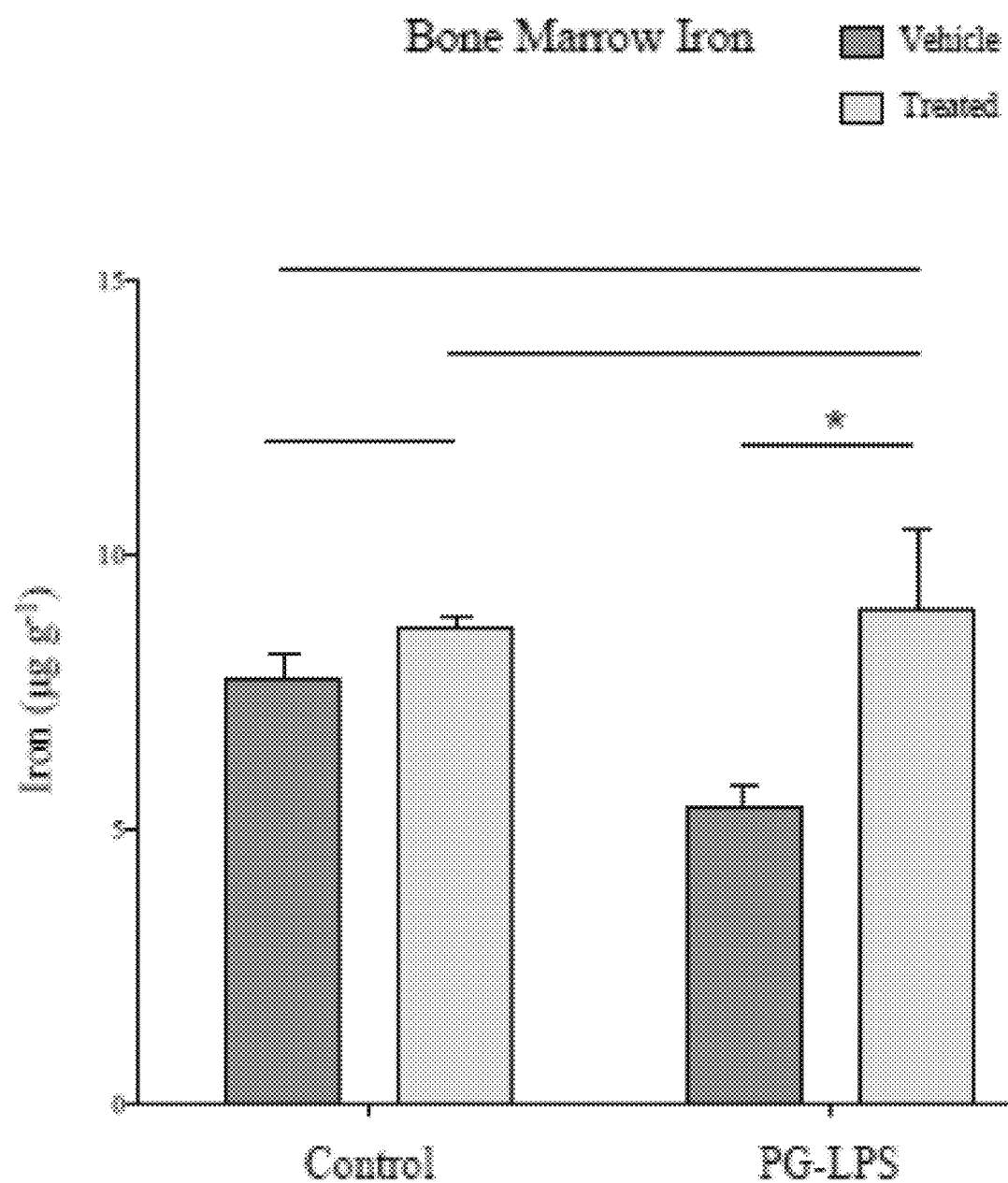

The data presented in FIGS. 32A-C confirms that iron levels are restored with nelfinavir treatment. Serum iron was not significantly different between healthy rats and healthy rats treated with nelfinavir (FIG. 32A). In contrast, the serum iron content of PG-LPS treated rats dropped to approximately half the iron content of healthy rats. PG-LPS treated rats that also received nelfinavir had ~25% more serum iron than the PG-LPS treated rats which was a significant increase in serum iron concentrations (FIG. 32A). This result is consistent with the lower hepcidin levels (FIG. 31B) and the elevated ferroportin levels (FIGS. 31D, 31E).

Liver iron content dropped significantly in healthy nelfinavir treated group as compared to the healthy animals (FIGS. 32A-C). This is easily explained by the approximate 3-fold increase in ferroportin in these rats (FIG. 31D).

Although the hepcidin levels are slightly higher in healthy nelfinavir treated rats than healthy rats (FIG. 31B), the prohepcidin levels are much higher than healthy rats (FIG. 31C) suggesting the PIs are blocking the action of hepcidin by inhibiting furin.

Figure 34A:
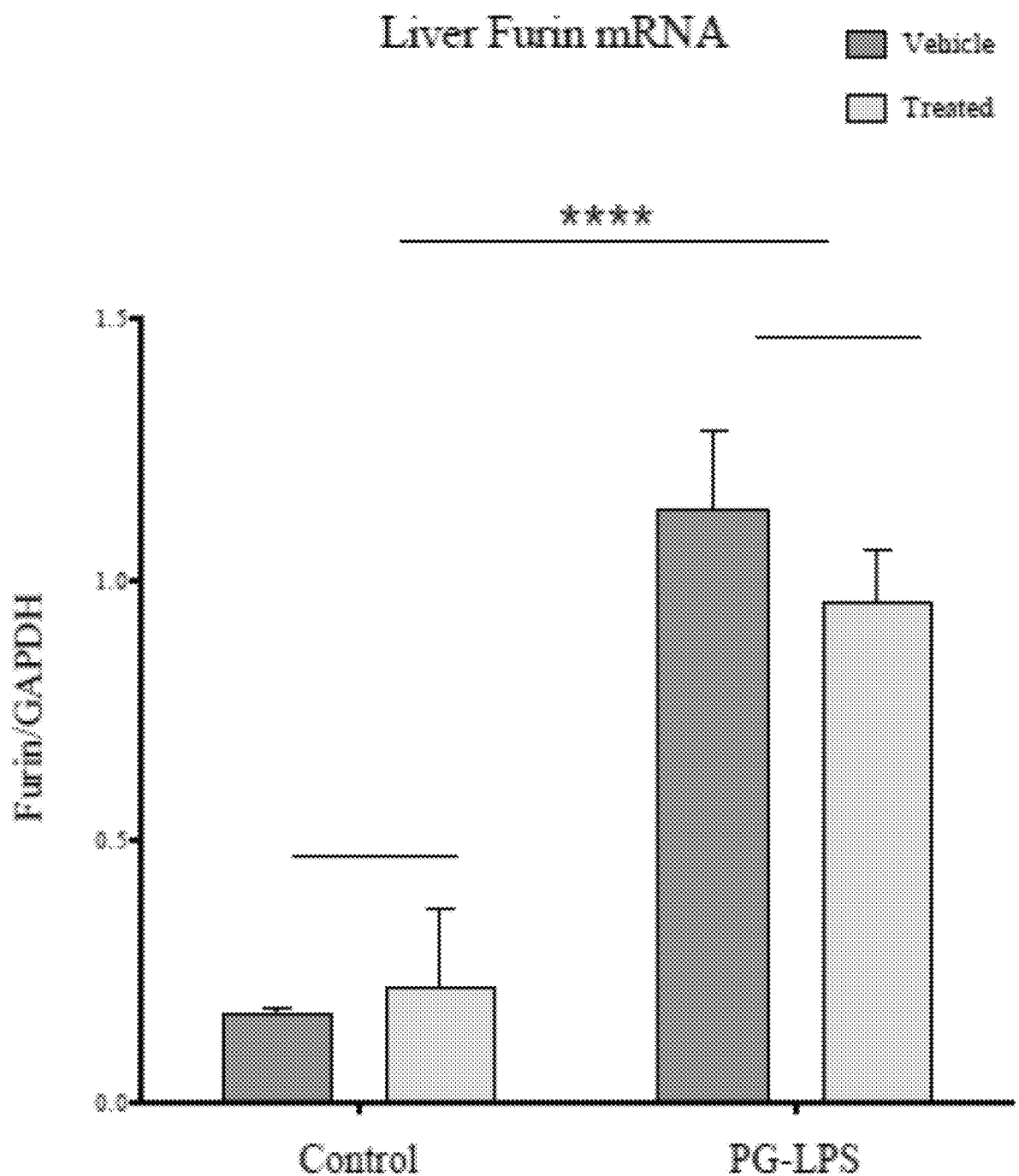
FIGS. 34A-C depict the furin expression in liver.
Figure 34B:
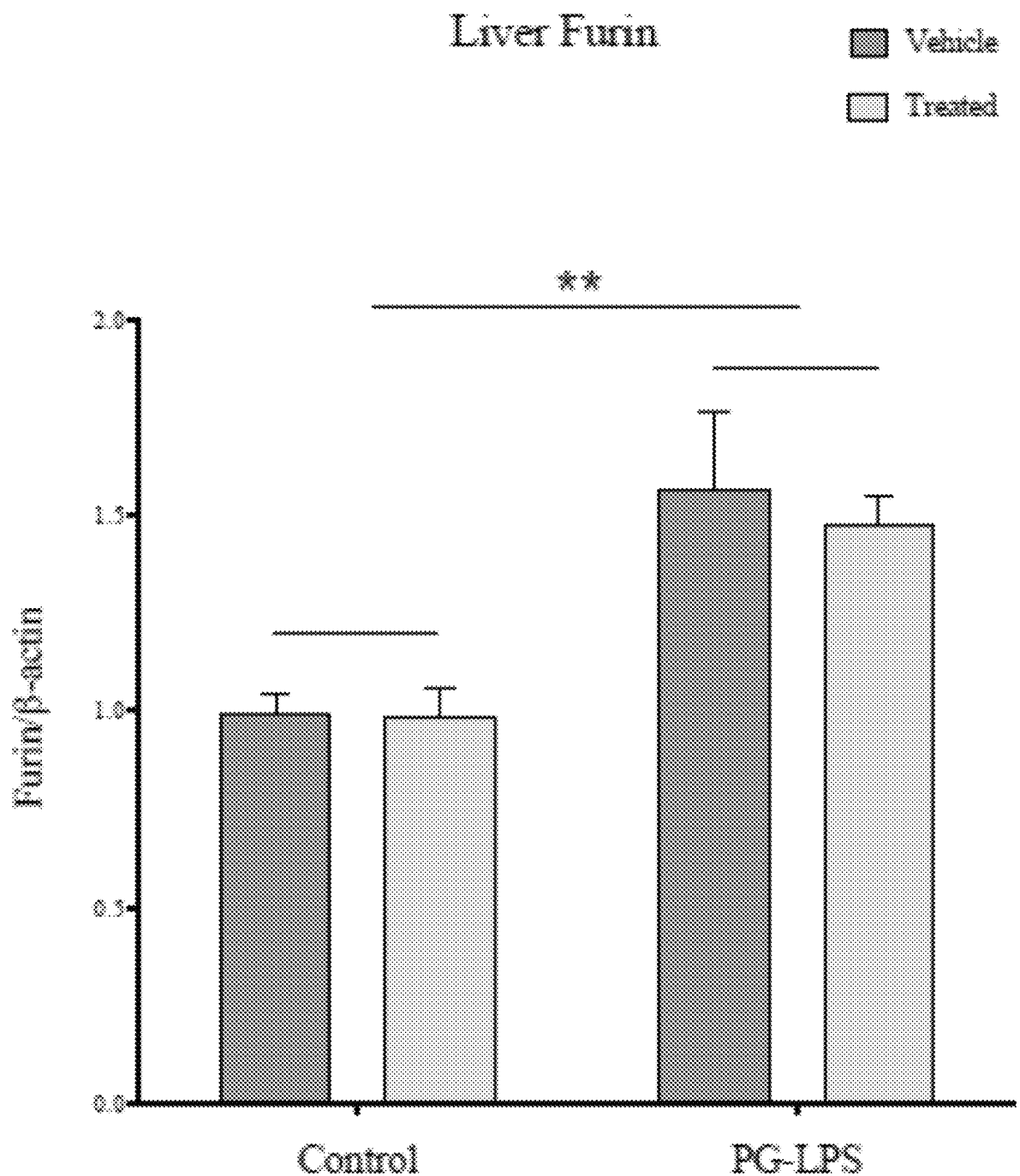
Figure 34C:
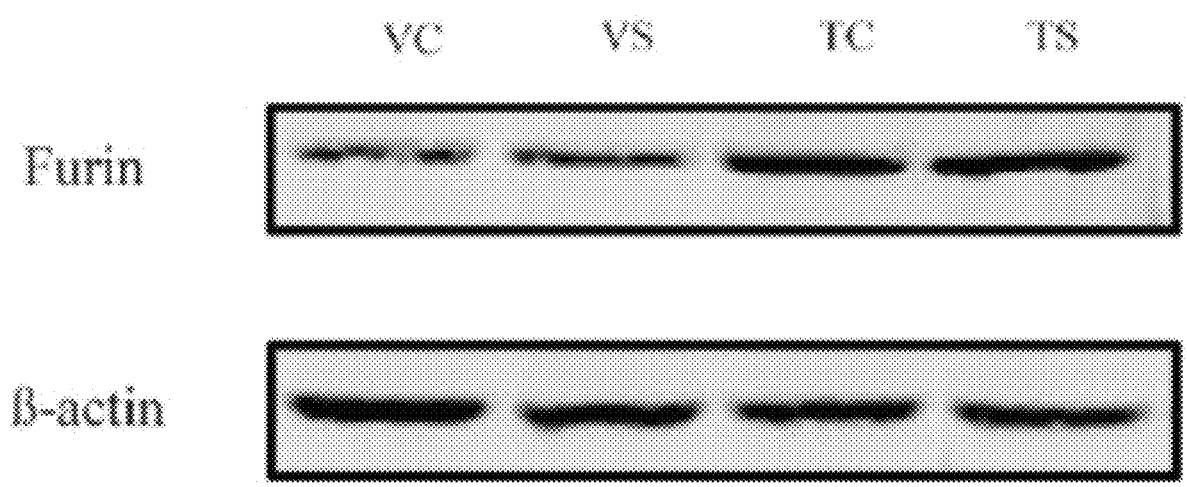

Furin is recognized as being upregulated with varying cancers and sarcomas. Furin expression is also known to increase under conditions of chronic immune activation. Using PG-LPS animals, furin is again characterized as being upregulated (FIGS. 34A-C). Despite this occurrence, furin activity is still significantly reduced as mature hepcidin-25 serum levels are shown to decrease, while prohepcidin levels increase.

It is also interesting to note that the serum iron content in healthy and healthy nelfinavir treated animals is maintained at a similar value even though the liver iron content decreases drastically in the nelfinavir treated animals (FIG. 31A). This likely represents optimal serum iron concentrations, as the highly elevated level of ferroportin is used to maintain serum iron concentrations in healthy nelfinavir treated animals (FIG. 32A). The release of iron from the liver of healthy animals treated with nelfinavir suggests that nelfinavir might be a potential treatment for hemochromatosis that will allow the liver to export excess iron. Combined treatment of nelfinavir with the $Fe^{3+}$ chelator desferal facilitates iron export from iron loaded cells and allow complexation of the iron by desferal for iron excretion.

PG-LPS animals have lower liver iron content than healthy animals (FIG. 32B). These results are likely due to the prolonged (6 weeks) inflammation incurred by the PG-LPS, as the average enterocyte life span ranges from only 4.7 to 10.2 days. Dietary iron is not absorbed during inflammatory situations with hepcidin present. Because of this, iron availability in liver steadily diminishes.

The elevated serum iron levels caused by PI treatment replenished iron stores in the bone marrow; as bone marrow iron content reached concentrations similar to that found in healthy rats (FIG. 32C). However, in the absence of nelfinavir, PG-LPS rats show the lowest bone marrow iron content (FIG. 32C). These results provide the proof of concept that furin inhibition that prevents the cleavage of prohepcidin to hepcidin can be used to restore normal iron delivery to the bone marrow.

PG-LPS animals showed significant signs of anemia within one week of induction. Mean Hb and Hematocrit levels fell from 15±0.4 and 14.1±1.1 g/dL to 13.6±0.5 13.0±1.1 g/dL with inoculation of PG-LPS. Hematocrit percentages also dropped from 43.1±1.1 and 41.5±2.4 to 39.7±2.1 and 37.6±3.9 within PG-LPS induced animals (FIG. 32, FIGS. 33A-B, FIGS. 39A-B, FIG. 40, and Table 4). These values illustrate the significant and prolonged anemia sustained within this model of ACI

TABLE 4

Summarized data of complete blood counts (CBC).

| Animal Group | Hb (g/dL) | | HCT (%) | | RDW (%) | | MCV (fl) | |
|---|---|---|---|---|---|---|---|---|
| | Day 0 | Day 62 | Day 0 | Day 62 | Day 0 | Day 62 | Day 0 | Day 62 |
| Vehicle Control | 14.5 ± 0.6 | 15.7 ± 0.5 | 41.9 ± 1.8 | 45.4 ± 1.7 | 12.6 ± 0.1 | 13.2 ± 0.3 | 55.7 ± 1.1 | 53.3 ± 0.9 |
| Treated Control | 14.4 ± 0.4 | 15.2 ± 0.2 | 41.5 ± 0.9 | 44.6 ± 2.7 | 12.6 ± 0.1 | 37.2 ± 0.7 | 55.3 ± 0.7 | 49.7 ± 0.5 |

TABLE 4-continued

Summarized data of complete blood counts (CBC).

| Animal Group | Hb (g/dL) | | HCT (%) | | RDW (%) | | MCV (fl) | |
|---|---|---|---|---|---|---|---|---|
| | Day 0 | Day 62 | Day 0 | Day 62 | Day 0 | Day 62 | Day 0 | Day 62 |
| Vehicle PG-LPS | 15 ± 0.4 | 13.6 ± 0.5 | 43.1 ± 1.1 | 39.7 ± 2.1 | 12.5 ± 0.3 | 42.3 ± 2.1 | 55.7 ± 0.8 | 47.6 ± 0.6 |
| Treated PG-LPS | 14.1 ± 1.1 | 13.0 ± 1.1 | 41.5 ± 2.4 | 37.6 ± 3.9 | 13.6 ± 2.5 | 42.8 ± 1.2 | 55.8 ± 1.5 | 46.7 ± 0.6 |

\* Values represent calculated mean of groups (Vehicle Control n = 4, Treated Control n = 4, Vehicle PG-LPS n = 8. Treated PG-LPS n = 7).

Figure 38:
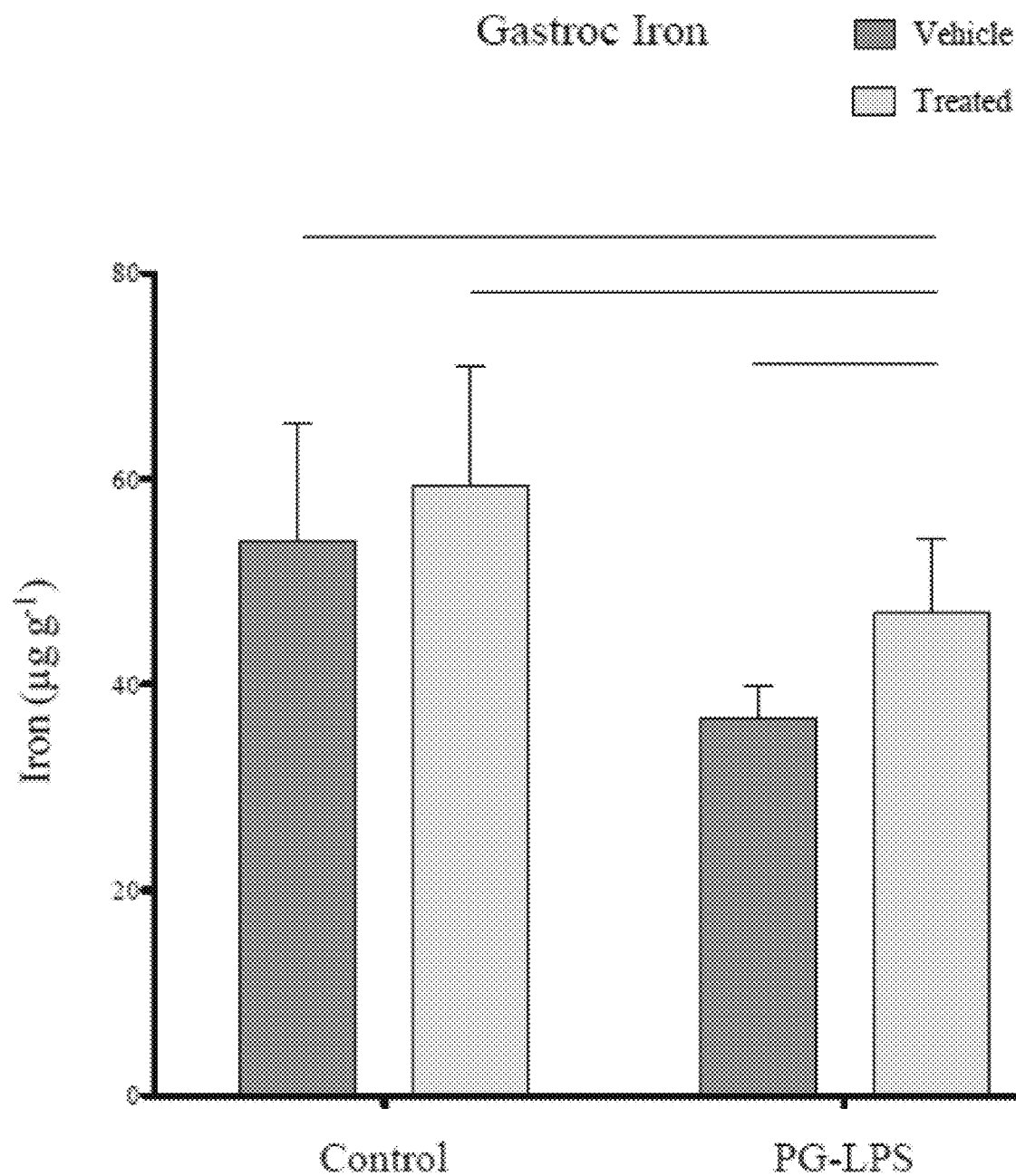
FIG. 38 shows muscle iron in the gastrocnemius.

Interpretation of low MCV values traditionally indicate onset of microcytic anemia, a symptom common of iron deficiency anemia. FIG. 38 shows low MCV in PG-LPS treated animal groups, along with a downtrend in treated controls. MCV values for PG-LPS animals decreases 14 days after inoculation, and continues on a downtrend for the remainder of the study.

Figure 36:
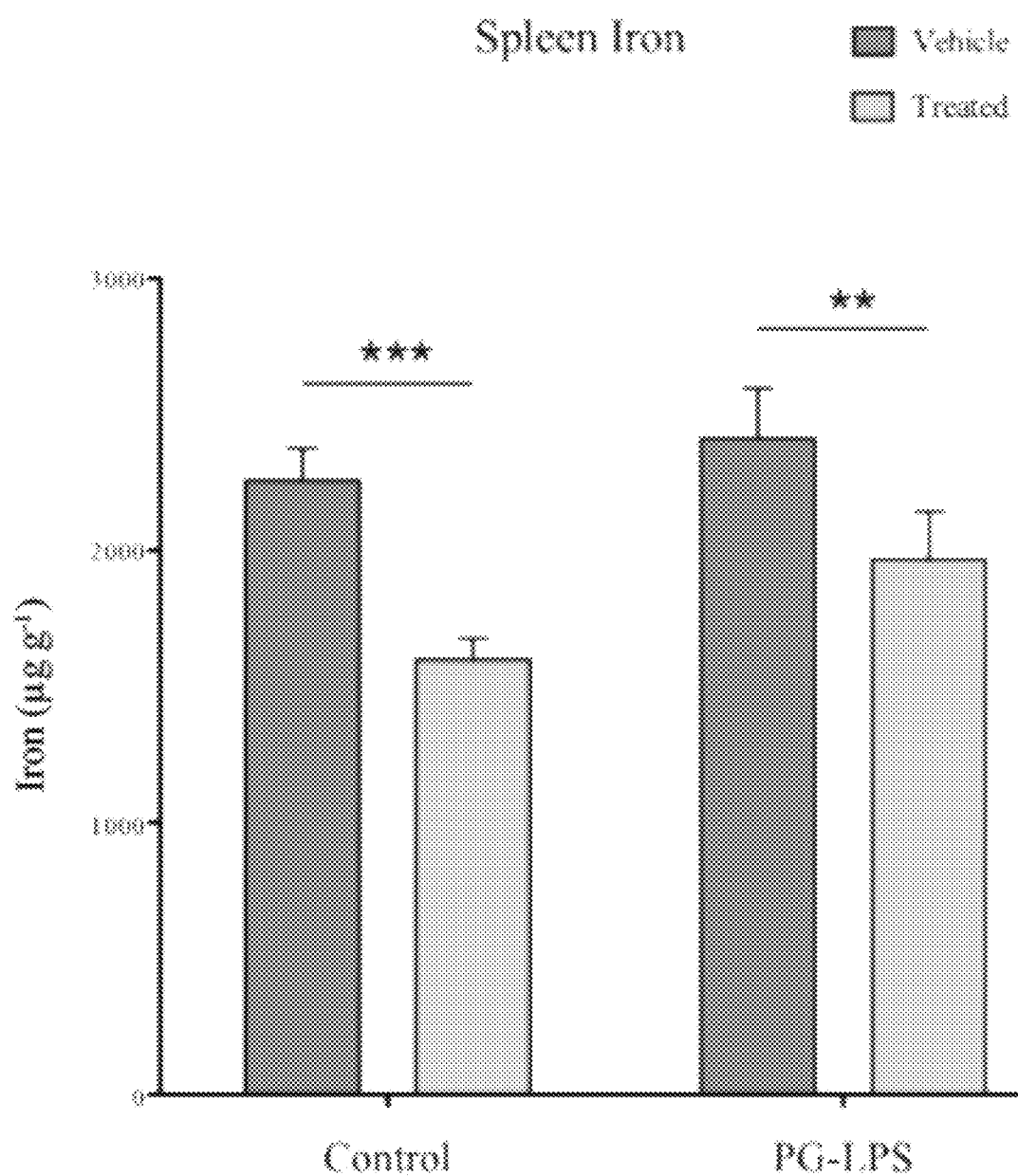
FIG. 36 shows spleen iron.
Figure 37:
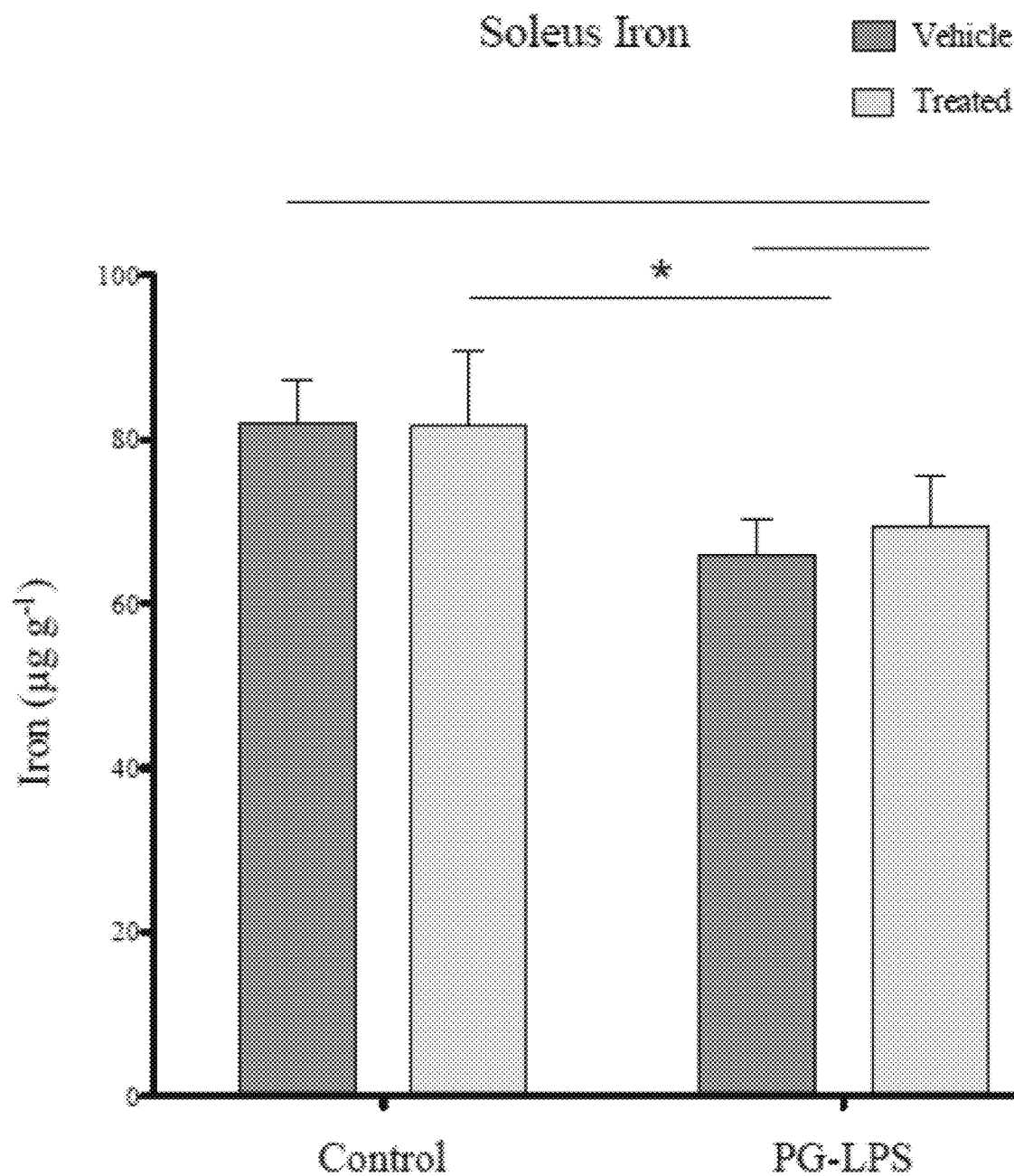
FIG. 37 shows muscle iron in the soleus.

High levels RDW % is observed in PG-LPS animal groups, whereas the vehicle control group remains steady throughout the study (FIG. 37). High RDW is commonly associated with iron deficiency when MCV values are also low. Treated control group RDW values increase over time to similar values. These data correlate with the loss in liver tissue iron with nelfinavir treated animals over time, concurrently representing a loss in tissue iron (FIG. 36).

Figure 39A:
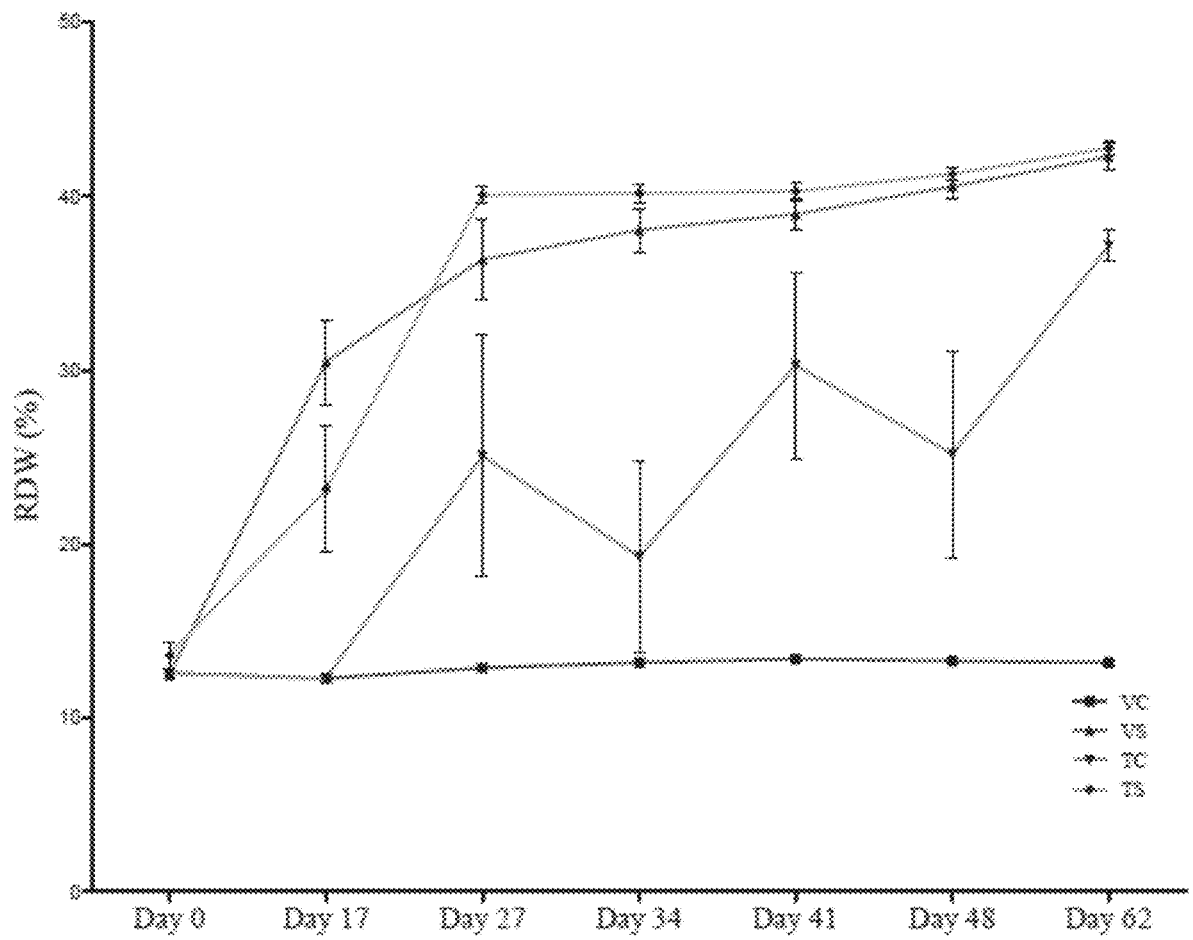
FIGS. 39A-B provide red blood cell indices.
Figure 39B:
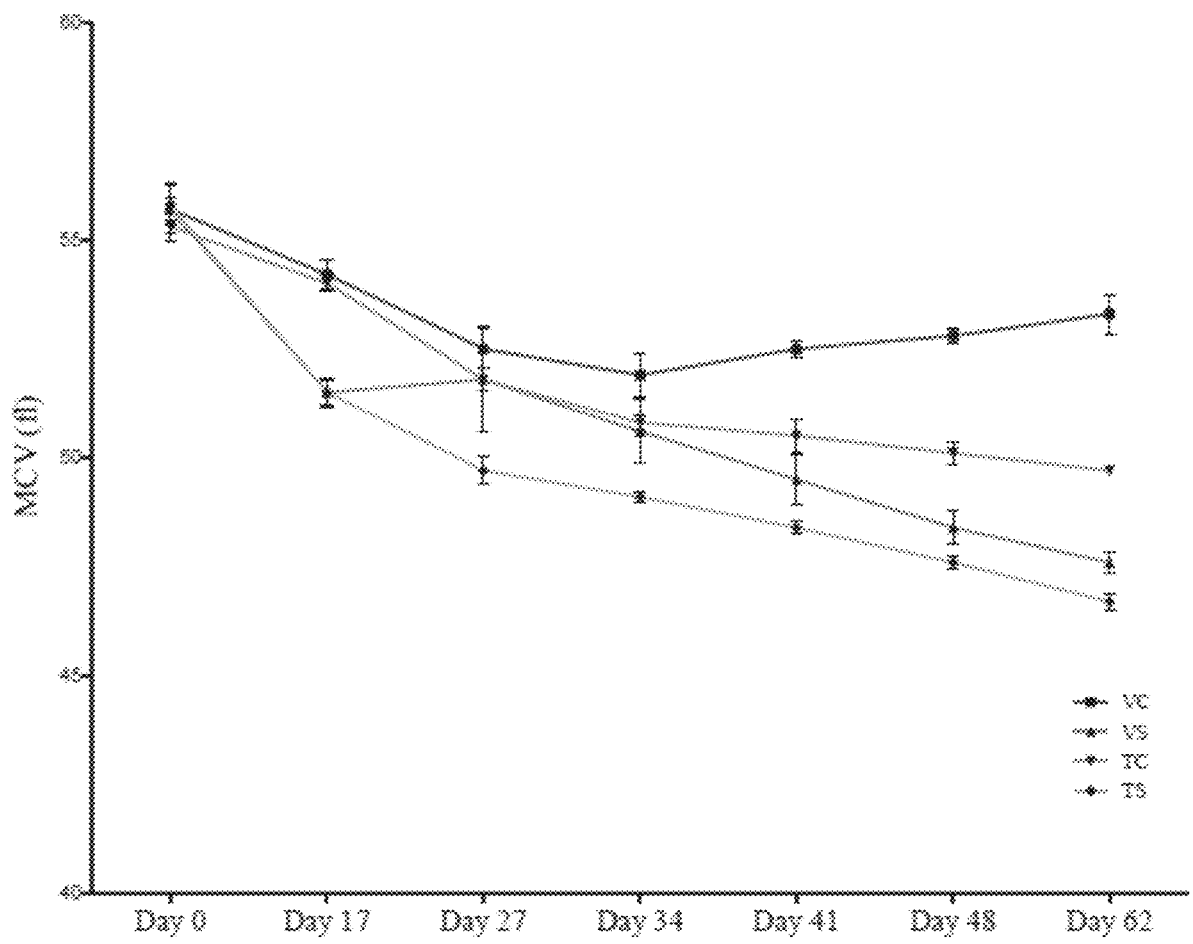
Figure 40:
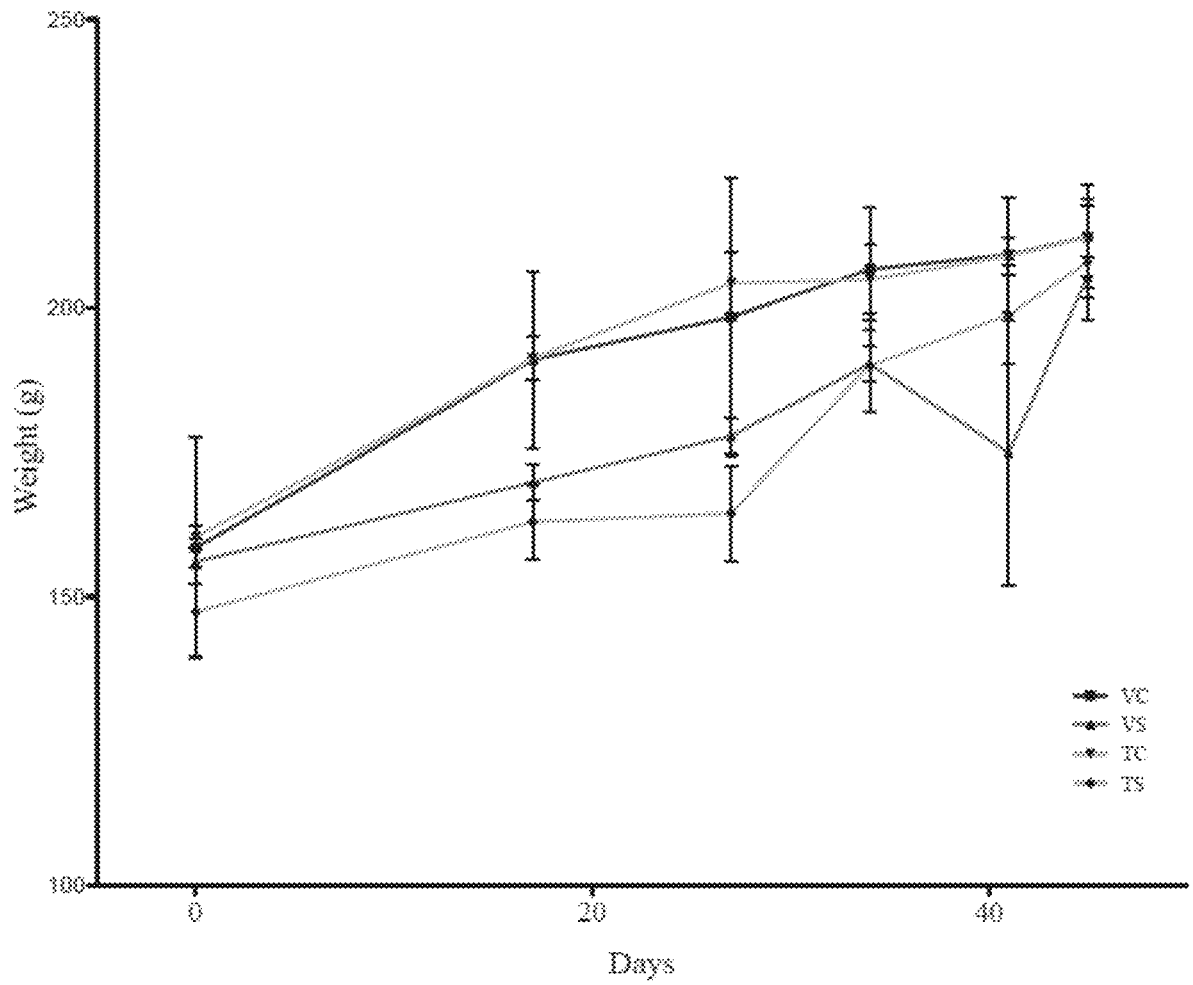
FIG. 40 shows the animal body weights measured during the course of treatment after PG-LPS inoculation.

Deficiencies in vitamin B12 or folate often produce large or increased RDW values, but are diagnosed as such only with increasing MCV values. High RDW values are shown with PG-LPS inoculation, and within the PI treated control group, representing the loss of iron available for sustained erythropoiesis within the animals, mimicking a clinical diagnosis of IDA (FIGS. 39A-B).

PG-LPS induced models of inflammation are known to induce hepcidin and cause hyporferremia within hours (Kemna, E. H. J. M. et al. Regulation of hepcidin: Insights from biochemical analyses on human serum samples. *Blood Cells. Mol. Dis.* 40, 339-346 (2008)). The sustained length (62 days) of this study outlasts initial hypoferremia symptoms, resulting in consequent tissue iron loss over time.

Figure 11A:
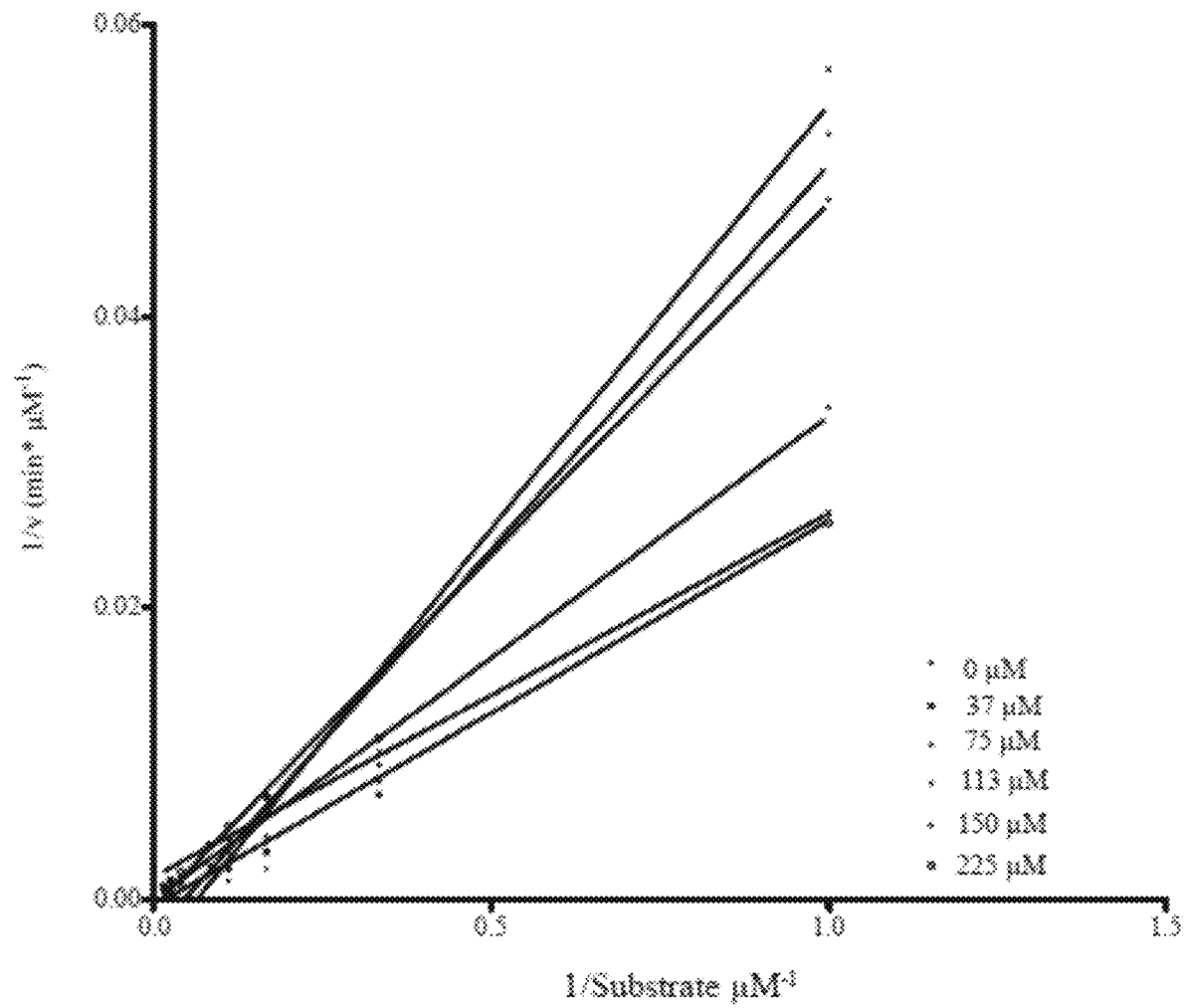
FIGS. 11A-B depict Lineweaver-Burk plots of nelfinavir and darunavir.
Figure 11B:
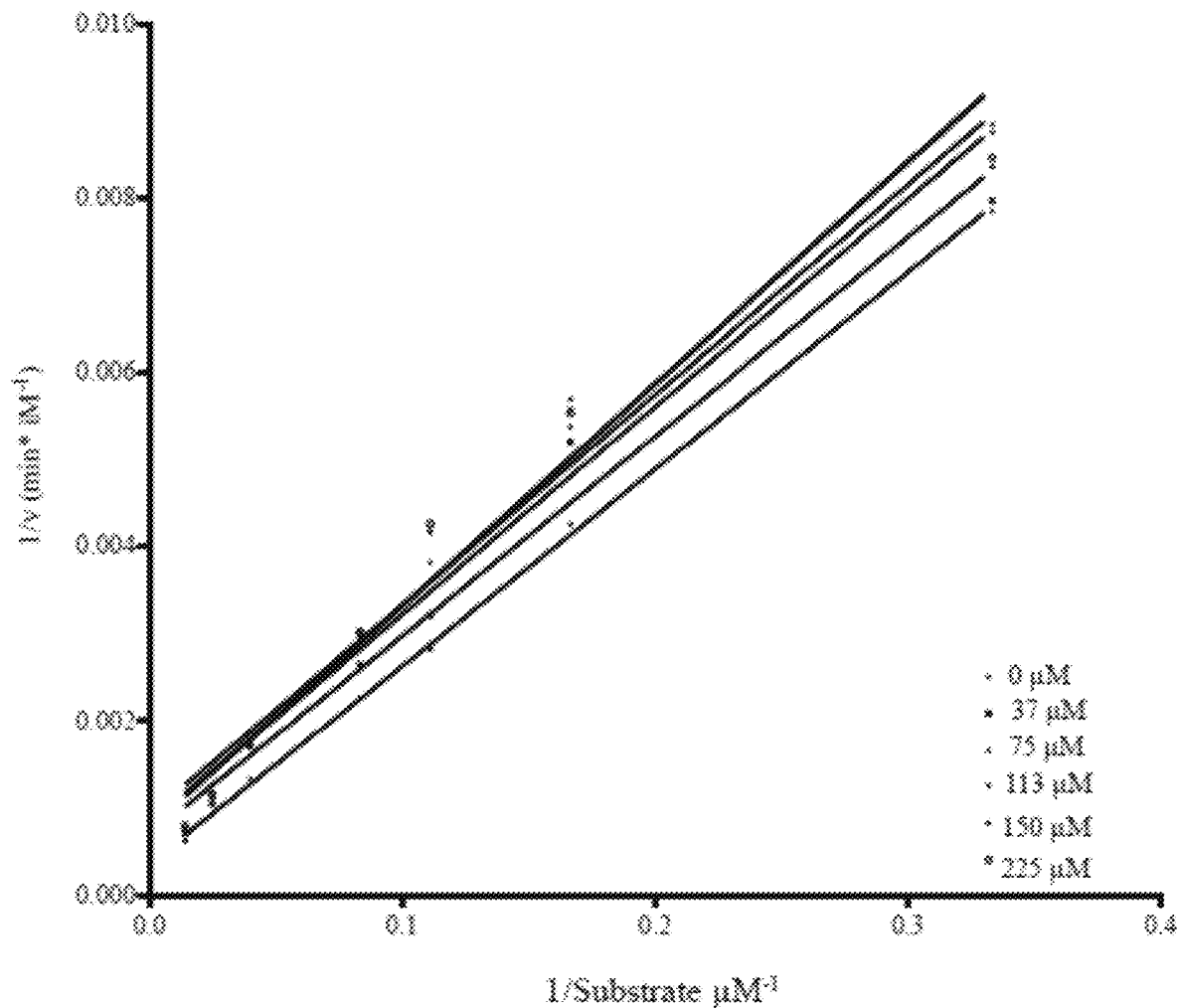

Molecular Docking studies were used to analyze the binding of known PIs to the proprotein convertase furin. These studies predicted that several of the PIs could bind tightly to the catalytic site of furin (FIGS. 7A and 7B). Additionally, several of the proposed ligands were predicted to bind to a putative allosteric site found between the catalytic domain and the P domain of furin (FIGS. 8A and 8B). Furin enzymatic assays confirmed that purified furin was inhibited by PIs, Additional analysis of the inhibition data showed that the PIs could be divided into two classes of inhibitors. The first class of PIs inhibited at the active site of furin and is represented by nelfinavir (FIGS. 7A, 8A and 11A). The second class of PIs inhibited at the allosteric site identified in the molecular docking and is represented by darunavir (FIGS. 7B, 8B and 11B). The addition of both catalytic site and allosteric site inhibitors (a combination of nelfinavir and darunavir) produced a synergistic effect causing significantly more inhibition than either drug alone (FIGS. 10A and 10B). Finally the inhibition of furin by HIV protease inhibitors was confirmed in cells using a model of ACI. The secretion of hepcidin, a hormone that is cut and activated by furin, was significantly decreased in the presence of the protease inhibitors nelfinavir and darunavir (FIG. 12).

In order to place the binding of PIs by furin and the associated inhibition data into context, the binding of PIs such as nelfinavir is compared to other protease enzymes. Nelfinavir was synthesized and engineered to bind to the HIV protease and calculations show an affinity of nelfinavir binding to HIV protease with a delta G ranging between −7 to −14 kcal/mol. The affinity of nelfinavir for binding to the aspartyl protease renin was determined to have a calculated affinity of −10.2 kcal/mol. Therefore the observation that nelfinavir bound to furin with affinities of −9.18 kcal/mol demonstrates only a slightly weaker binding for furin than its original target or for another aspartyl protease. Additionally, the affinity of nelfinavir binding to furin was very close to the known inhibitor CMK with a ΔG of −11.07 kcal/mol.

Other HIV PIs showed comparable binding affinities between HIV protease, renin and furin. Darunavir showed the following affinities calculated by molecular docking: ΔG——9.58 for HIV protease, −10.33 for renin and −8.18 for the allosteric site of furin. Similar results were observed for the HIV protease inhibitors ritonavir and indinavir.

The surprising identification of an allosteric site on furin allows for the fine tuning of the inhibition of furin. The cleft at the interface of the P domain and the catalytic domain provides a new target to regulate the activity of furin.

Additionally, the allosteric site provides a mechanism to further inhibit furin through a synergistic inhibition. The combination of catalytic site and allosteric site inhibitors produces a new and potentially potent method to inhibit furin activity (FIG. 10B). This combination allows treatments designed to have a potent inhibitory effect at high concentrations or may allow' an attenuation of furin activity when the combination of both classes of inhibitors is used at much lower concentrations. These studies have all been performed in a 1:1 ratio. It is possible that holding the inhibitor to one site constant and varying the concentration of the inhibitor to the other site might also provide the ability to fine tune the effect on furin inhibition. Another benefit is that the lower doses of the combination therapy might minimize any side effects caused by the individual drugs used at higher concentrations.

One of skill in the art will readily recognize that the methods described herein can be applied to the screening and testing of small molecules as potential inhibitors of proteases. Once a crystal structure is obtained, the methods described herein can be applied for inhibition. Additionally, the impact on the field of protease field is significant because it can be used to explain many of the side effects related to HIV protease inhibitors. Such screens can be used to identify and understand off target inhibition of the PIs.

In addition, embodiments described herein provide a new approach to furin inhibition. Inhibition of furin at the catalytic, allosteric or both sites can now be used as a method to treat a subject at risk of or having diseases including ACI, as well as the treatment of underlying disease, such as those described herein, including an infectious disease, an inflammatory disease, heart disease, kidney disease, cancer, Alzheimer's disease, Parkinson's disease, Human Immunodeficiency Virus (HIV), Hepatitis-C virus (HCV), cytomegalovirus (CMV), Dengue virus, Ebola virus, Lassa virus, West Nile virus, rheumatoid arthritis, vasculitis, sarcoid, inflammatory' bowel disease, multiple sclerosis, atherosclerosis, diabetes, congestive heart failure, or combinations of any of the aforementioned diseases.

As provided herein, nelfinavir inhibits the phosphorylation of STAT3 in a concentration dependent manner (FIGS. 24A and 24B). However, this inhibition appeared to only have a small inhibitory effect on HAMP production when compared to the known furin inhibitor CMK (FIG. 26A), Ritonavir also showed inhibition of STAT3 phosphorylation, but this effect was not concentration dependent, and seemed to cause about a 25% inhibition at all concentrations tested. In contrast darunavir and indinavir did not show any statistically significant inhibition of pSTAT3.

Treatment of cells with IL-6 and BMP-9 increased the overall concentrations of pSmad4 and pSmad1/5 but the addition of the protease inhibitors showed no statistically significant changes to the phosphorylation states of these proteins when comparing to inflammatory or non-inflammatory conditions. Together, these data suggest that when using the nelfinavir and darunavir combination, a slight pSTAT3 inhibition occurs due to the presence of nelfinavir but not darunavir, without effect to the SMAD signaling pathway.

Measurements of HAMP mRNA demonstrate that the inflammatory cytokines are activating the HAMP gene. Analysis of secreted hepcidin and prohepcidin in the presence and absence of PIs allows us to evaluate the relative effectiveness of furin inhibition by nelfinavir and darunavir. Prohepcidin levels increase significantly when nelfinavir and darunavir are added to cells treated with IL-6 and BMP-9 indicating that furin was inhibited and prohepcidin could not be processed to hepcidin (FIG. 26B). In contrast the opposite observation is made for hepcidin. Hepcidin secretion is high in IL-6/BMP-9 treated cells (FIG. 28A) but the presence of nelfinavir and darunavir drops hepcidin levels back to the basal level of secretion seen in healthy cells while the prohepcidin secretion increases drastically (FIG. 26B) indicating that furin was unable to cut prohepcidin to hepcidin. The decreased level of hepcidin secreted was not due to a decrease in total furin protein. In fact, FIG. 27B demonstrates that inflammation increases the transcription of furin mRNA, and that protein expression is approximately 50% higher than in healthy cells (FIG. 27C), further indicating that nelfinavir and darunavir treatment is inhibiting furin.

Finally, a key indicator for treating ACI is the restoration and stabilization of ferroportin on the surface of cells to allow iron export into the bloodstream. Inhibition of hepcidin, as provided herein, results in stable ferroportin expression and normal iron release from cells as a pathway for future treatment of anemia. Ferroportin levels increase dramatically when hepcidin secretion is inhibited (FIG. 29D). The dual treatment of nelfinavir and darunavir at 15 µM had a much stronger effect on increasing ferroportin levels than the known furin inhibitor CMK at 25 µM concentrations.

This is a further testament that nelfinavir and darunavir have a synergistic effect for furin inhibition. Nelfinavir is a catalytic site inhibitor and darunavir is an allosteric site inhibitor. The combination of these two drugs for inhibiting furin and the pSTAT3 inhibition capability of nelfinavir to inhibit HAMP transcription combine to provide a significant inhibitory effect to prevent hepcidin secretion. As provided herein, nelfinavir is a dual inhibitor of hepcidin production, acting as both a transcriptional inhibitor and an activation inhibitor.

The transcription of the HAMP gene in PG-LPS treated animals was similar even with nelfinavir treatment indicating that nelfinavir did not provide significant inhibition of the IL-6/STAT3 or BMP/SMAD pathways. Nelfinavir inhibition of HAMP transcription was not apparent in this study, due to elevated levels of both IL-6 and BMP-9 in these animals. The BMP/SMAD pathway appears to be a more potent activator of HAMP and also influences the IL-6 activation of HAMP where the IL-6 pathway does not influence the BMP/SMAD pathway. Therefore the similar expression of HAMP even with nelfinavir treatment remains elevated.

Nelfinavir treatment decreased serum hepcidin levels (~2-fold) and increased serum prohepcidin levels (~2.5 fold) in PG-LPS treated animals. This supports the hypothesis that nelfinavir inhibits furin and prevents prohepcidin cleavage. In addition, lower hepcidin levels allowed increased expression of ferroportin on the surface of liver tissue. The decrease in hepcidin levels and increase in ferroportin levels allow iron export from iron-rich tissue.

Nelfinavir treated PG-LPS treated animals did not demonstrate a recovery of hematocrit or hemoglobin levels, even with the recovery of serum iron and bone marrow iron. Presumably the BMP concentrations that are inhibited by LDN-193198 and HJV-fc treatment are not affected by nelfinavir treatment. The BMP cytokines influence pathways related to inhibiting the proliferation and differentiation of erythroid progenitor cells and also impair EPO production and response to EPO. Therefore, even though nelfinavir restores normal iron mobilization, the low levels of EPO in the PG-LPS model prevent erythropoiesis. The lack of EPO prevented the recovery of anemia until ESAs were co-administered with the anti-hepcidin antibody. The use of ESAs with nelfinavir allows the recovery of anemia in this model.

In summary, the protease inhibitor nelfinavir inhibits furin and prevents the processing of prohepcidin to hepcidin. This allows for the stable expression of ferroportin on the surface of iron-rich cells during ACI and restores iron mobilization allowing normal iron levels in serum and bone marrow. As provided herein, pharmaceutical compositions, including at least on protease inhibitor. In some embodiments, the at least one protease inhibitor is nelfinavir, darunavir, or both can be used in combination with ESAs to treat ACI.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. Further, with respect to each of the studies and publications mentioned herein, each is hereby expressly incorporated by reference in its entirety.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least, one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for modulating iron metabolism in a subject, comprising: determining an amount of serum hepcidin in a subject suffering from or at risk of developing anemia; and administering to the subject a pharmaceutical composition comprising one or more protease inhibitors when the amount of serum hepcidin is above normal levels, wherein the one or more protease inhibitors inhibit furin activity.

2. The method of claim 1, wherein the anemia is anemia of chronic inflammation.

3. The method of claim 1, wherein the amount of serum hepcidin in a subject is determined to be greater than about 50 ng/ml.

4. The method of claim 1, wherein modulating iron metabolism in a subject comprises any one of: increasing serum iron levels, increasing bone marrow iron levels, increasing red blood cell counts, and increasing hemoglobin levels, and combinations thereof.

5. The method of claim 1, wherein the pharmaceutical composition comprises nelfinavir, darunavir, or ritonavir, and any combination thereof.

6. The method of claim 1, wherein the one or more protease inhibitor is present in an amount of about 1-2500 mg.

7. The method of claim 1, wherein the pharmaceutical composition comprises ritonavir present in an amount of about 1 mg, nelfinavir present in an amount of about 10 mg, and/or darunavir present in an amount of about 5 mg.

8. The method of claim 1, wherein the pharmaceutical composition is administered to the subject once daily.

9. The method of claim 7, wherein the pharmaceutical composition is administered to the subject once daily.

10. The method of claim 1, wherein the pharmaceutical composition comprises darunavir and ritonavir.

11. The method of claim 10, wherein the pharmaceutical composition is administered to the subject twice daily.

12. The method of claim 1, wherein the pharmaceutical composition further comprises an iron compound, erythropoietin, a chemotherapy drug, or a combination thereof.

13. The method of claim 12, wherein the iron compound is selected from the group consisting of ferrous sulfate, ferrous fumarate, ferric pyrophosphate, iron gluconate, iron sucrose, iron dextran, intravenous iron treatments, and combinations thereof.

14. The method of claim 1, wherein the pharmaceutical composition comprises one or more protease inhibitors as the sole active ingredient.

15. The method of claim 1, wherein the pharmaceutical composition does not comprise an antibody.

16. The method of claim 1, wherein the one or more protease inhibitors is an HIV protease inhibitor that is selected from nelfinavir, darunavir, ritonavir, tipranavir, and any combination thereof.

17. The method of claim 1, wherein the one or more protease inhibitors is an HIV protease inhibitor that is selected from nelfinavir, darunavir, ritonavir, and any combination thereof.

18. The method of claim 1, wherein the one or more protease inhibitors are at least two HIV protease inhibitors that are administered to the subject.

19. The method of claim 18, wherein the at least two HIV protease inhibitors are nelfinavir and ritonavir.

20. The method of claim 1, wherein the subject is undergoing dialysis.

21. The method of claim 1, wherein the subject is diagnosed with inflammatory bowel disease (IBD).

* * * * *